(12) United States Patent
Bremer et al.

(10) Patent No.: US 7,807,068 B2
(45) Date of Patent: Oct. 5, 2010

(54) POLYMERIZABLE COMPOUNDS

(75) Inventors: Matthias Bremer, Darmstadt (DE);
Achim Goetz, Alsbach-Haehnlein (DE);
Stephan Derow, Griesheim (DE)

(73) Assignee: Merck Patent Gesellschaft, Darmstadt (DE)

( * ) Notice: Subject to any disclaimer, the term of this patent is extended or adjusted under 35 U.S.C. 154(b) by 0 days.

(21) Appl. No.: 12/275,652

(22) Filed: Nov. 21, 2008

(65) Prior Publication Data

US 2009/0141215 A1 Jun. 4, 2009

(30) Foreign Application Priority Data

Nov. 30, 2007 (DE) ................. 10 2007 057 680

(51) Int. Cl.
*C09K 19/00* (2006.01)
*C09K 19/06* (2006.01)
*C09K 19/52* (2006.01)
*G02F 1/03* (2006.01)

(52) U.S. Cl. ............... 252/299.01; 252/299.1; 252/299.6; 430/20; 428/1.1; 428/1.3

(58) Field of Classification Search ............ 252/299.01, 252/299.1, 299.6; 428/1.1, 1.3; 430/20, 430/270.1
See application file for complete search history.

(56) References Cited

U.S. PATENT DOCUMENTS 5,645,760 A 7/1997 Yamada et al.
6,177,972 B1 1/2001 Held et al.

OTHER PUBLICATIONS

M. Escuti et al., "Enhanced Dynamic Response of the In-Plane Switching Liquid Crystal Display Mode Through Polymer Stabilization", Applied Physics Letters, vol. 75, No. 21 (Nov. 22, 1999) pp. 3264-3266.

Y. Lu et al., "Variable Optical Attenuator Based on Polymer Stabilized Twisted Nematic Liquid Crystal", Optics Express, vol. 12, No. 7 (Apr. 5, 2004) pp. 1221-1227.

*Primary Examiner*—Geraldina Visconti
(74) *Attorney, Agent, or Firm*—Millen, White, Zelano, Branigan, P.C.

(57) ABSTRACT

The present invention relates to novel polymerizable compounds, to processes and intermediates for the preparation thereof, and to the use thereof for optical, electro-optical and electronic purposes, in particular in liquid-crystal (LC) media and LC displays, especially in LC displays of the PS (polymer-stabilized) and PSA (polymer-sustained alignment) type.

26 Claims, No Drawings

POLYMERIZABLE COMPOUNDS

The present invention relates to novel polymerizable compounds, to processes and intermediates for the preparation thereof, and to the use thereof for optical, electro-optical and electronic purposes, in particular in liquid-crystal (LC) media and LC displays, especially in LC displays of the PS (polymer-stabilized) and PSA (polymer-sustained alignment) type.

The liquid-crystal displays (LC displays) used at present are usually those of the TN (twisted nematic) type. However, these have the disadvantage of a strong viewing-angle dependence of the contrast. In addition, so-called VA (vertical alignment) displays are known which have a broader viewing angle. The LC cell of a VA display contains a layer of an LC medium between two transparent electrodes, where the LC medium usually has a negative value of the dielectric (DC) anisotropy. In the switched-off state, the molecules of the LC layer are aligned perpendicular to the electrode surfaces (homeotropically) or have a tilted homeotropic alignment. On application of an electrical voltage to the electrodes, a realignment of the LC molecules parallel to the electrode surfaces takes place. Furthermore, OCB (optically compensated bend) displays are known which are based on a birefringence effect and have an LC layer with a so-called "bend" alignment and usually positive (DC) anisotropy. On application of an electrical voltage, a realignment of the LC molecules perpendicular to the electrode surfaces takes place. In addition, OCB displays normally contain one or more birefringent optical retardation films in order to prevent undesired transparency to light of the bend cell in the dark state. OCB displays have a broader viewing angle and shorter response times compared with TN displays. Also known are IPS (in-plane switching) displays, which contain an LC layer between two substrates, only one of which has an electrode layer, usually with a comb-shaped structure. On application of a voltage, an electric field which has a significant component parallel to the LC layer is thereby generated. This causes realignment of the LC molecules in the layer plane. Furthermore, so-called FFS (fringe-field switching) displays have been proposed (see, inter alia, S. H. Jung et al., Jpn. J. Appl. Phys., Volume 43, No. 3, 2004, 1028), which likewise contain two electrodes on the same substrate, but, in contrast to IPS displays, only one of these is in the form of a structured (comb-shaped) electrode, and the other electrode is unstructured. A strong, so-called "fringe field" is thereby generated, i.e. a strong electric field close to the edge of the electrodes, and, throughout the cell, an electric field which has both a strong vertical component and also a strong horizontal component. Both IPS displays and also FFS displays have a low viewing-angle dependence of the contrast.

In VA displays of the more recent type, uniform alignment of the LC molecules is restricted to a plurality of relatively small domains within the LC cell. Disclinations may exist between these domains, also known as tilt domains. VA displays having tilt domains have, compared with conventional VA displays, a greater viewing-angle independence of the contrast and the grey shades. In addition, displays of this type are simpler to produce since additional treatment of the electrode surface for uniform alignment of the molecules in the switched-on state, such as, for example, by rubbing, is no longer necessary. Instead, the preferential direction of the tilt or pretilt angle is controlled by a special design of the electrodes. In so-called MVA (multidomain vertical alignment) displays, this is usually achieved by the electrodes having protrusions which cause a local pretilt. As a consequence, the LC molecules are aligned parallel to the electrode surfaces in different directions in different, defined regions of the cell on application of a voltage. "Controlled" switching is thereby achieved, and the formation of interfering disclination lines is prevented. Although this arrangement improves the viewing angle of the display, it results, however, in a reduction in its transparency to light. A further development of MVA uses protrusions on only one electrode side, while the opposite electrode has slits, which improves the transparency to light. The slitted electrodes generate an inhomogeneous electric field in the LC cell on application of a voltage, meaning that controlled switching is still achieved. For further improvement of the transparency to light, the separations between the slits and protrusions can be increased, but this in turn results in a lengthening of the response times. In the so-called PVA (patterned VA), protrusions are rendered completely superfluous in that both electrodes are structured by means of slits on the opposite sides, which results in increased contrast and improved transparency to light, but is technologically difficult and makes the display more sensitive to mechanical influences (tapping, etc.). For many applications, such as, for example, monitors and especially TV screens, however, a shortening of the response times and an improvement in the contrast and luminance (transmission) of the display are required.

A further development are the so-called PS (polymer-stabilized) displays, which are also known under the term "PSA" (polymer-sustained alignment). In these, a small amount (for example 0.3% by weight, typically <1% by weight) of a polymerizable compound is added to the LC medium and, after introduction into the LC cell, is polymerized or cross-linked in situ, usually by UV photopolymerization, with an electrical voltage applied between the electrodes. The addition of polymerizable mesogenic or liquid-crystalline compounds, also known as "reactive mesogens" (RMs), to the LC mixture has proven particularly suitable.

In the meantime, the PS(A) principle is being used in diverse classical LC displays. Thus, for example, PSA-VA, PSA-OCB, PS-IPS and PS-TN displays are known. As can be demonstrated in test cells, the PSA method results in a pretilt in the cell. In the case of PSA-OCB displays, it is therefore possible for the bend structure to be stabilized so that an offset voltage is unnecessary or can be reduced. In the case of PSA-VA displays, this pretilt has a positive effect on response times. For PSA-VA displays, a standard MVA or PVA pixel and electrode layout can be used. In addition, however, it is possible, for example, to manage with only one structured electrode side and no protrusions, which significantly simplifies production and at the same time results in very good contrast at the same time as very good transparency to light.

PSA-VA displays are described, for example, in JP 10-036847 A, EP 1 170 626 A2, EP 1 378 557 A1, EP 1 498 468 A1, US 2004/0191428 A1, US 2006/0066793 A1 and US 2006/0103804 A1. PSA-OCB displays are described, for example, in T.-J- Chen et al., Jpn. J. Appl. Phys. 45, 2006, 2702-2704 and S. H. Kim, L.-C- Chien, Jpn. J. Appl. Phys. 43, 2004, 7643-7647. PS-IPS displays are described, for example, in U.S. Pat. No. 6,177,972 and Appl. Phys. Lett. 1999, 75(21), 3264. PS-TN displays are described, for example, in Optics Express 2004, 12(7), 1221.

In particular for monitor and especially TV applications, optimization of the response times, but also of the contrast and luminance (thus also transmission) of the LC display continues to be demanded. The PSA method can provide crucial advantages here. In particular in the case of PSA-VA, a shortening of the response times, which correlate with a measurable pretilt in test cells, can be achieved without significant adverse effects on other parameters.

However, it has been found that the LC mixtures and RMs known from the prior art still have some disadvantages on use in PS(A) displays. Thus, not every desired soluble RM by far is suitable for use in PS(A) displays, and it is often difficult to find more suitable selection criteria than the direct PSA experiment with pretilt measurement. The choice becomes even smaller if polymerization by means of UV light without the addition of photoinitiators is desired, which may be advantageous for certain applications. In addition, the LC mixture (also referred to as "LC host mixture" below)+polymerizable component "material system" selected should have the lowest possible rotational viscosity and the best possible electrical properties, with the emphasis here on the so-called "voltage holding ratio" (HR or VHR). In connection with PSA-VA, a high HR after irradiation with (UV) light is, in particular, of central importance since this is an indispensible part of the process, but naturally also occurs as "normal" exposure in the finished display. However, the problem arises that not all LC mixture+polymerizable component combinations by far are suitable for PS(A) displays since, for example, no tilt or an inadequate tilt arises or since, for example, the HR is inadequate for TFT display applications.

Thus, there continues to be a great demand for PS(A) displays, in particular of the VA and OCB type, and LC media and polymerizable compounds for use in such displays which do not exhibit the disadvantages described above or only do so to a small extent and have improved properties. In particular, there is a great demand for PS(A) displays and materials having high specific resistance at the same time as a large working-temperature range, short response times, even at low temperatures, and low threshold voltage which facilitate a multiplicity of grey shades, high contrast and a broad viewing angle, and have high values of the "voltage holding ratio" (HR) after UV exposure.

Thus, in accordance with the invention, there are provided novel suitable materials, in particular polymerizable compounds and LC media comprising the latter, for use in PS(A) displays which do not have the disadvantages indicated above or only do so to a reduced extent, enable a pretilt angle to be established and preferably simultaneously have very high specific resistance values, low threshold voltages and short response times.

In accordance with an aspect of the invention, there are provided novel polymerizable mesogenic compounds (reactive mesogens, "RMs"), in particular for optical, electro-optical, electronic, decorative and cosmetic applications, and of suitable processes and intermediates for the preparation thereof.

In particular, it has been found, surprisingly, that polymerizable compounds according to the invention enable the desired tilt angles to be established on use in PS(A) displays. This has been demonstrated in combination with an LC medium by means of pretilt measurements. In particular, it has been possible to achieve a pretilt without the addition of photoinitiator.

The invention thus relates to compounds of the formula I

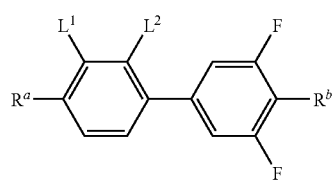

I in which the individual radicals have the following meanings:

$R^a$ and $R^b$ denote P-Sp-, H, F, Cl, Br, I, —CN, —NCO, —NCS, —OCN, —SCN, $SF_5$ or straight-chain or branched alkyl having 1 to 25 C atoms, in which, in addition, one or more non-adjacent $CH_2$ groups may each be replaced, independently of one another, by —C($R^{00}$)=C($R^{000}$)—, —C≡C—, —N($R^{00}$)—, —O—, —S—, —CO—, —CO—O—, —O—CO—, —O—CO—O— in such a way that O and/or S atoms are not linked directly to one another, and in which, in addition, one or more H atoms may be replaced by F, Cl, Br, I, CN or P-Sp-, where at least one of the radicals $R^a$ and $R^b$ denotes or contains a group P-Sp-, P on each occurrence, identically or differently, denotes a polymerizable group, Sp on each occurrence, identically or differently, denotes a spacer group or a single bond, $R^{00}$ and $R^{000}$ each, independently of one another, denote H or alkyl having 1 to 12 C atoms, $L^1$ and $L^2$ each, independently of one another, denote H or F.

The invention furthermore relates to novel processes for the preparation of compounds of the formula I and to intermediates obtained or used therein, in particular compounds of the formula Ia

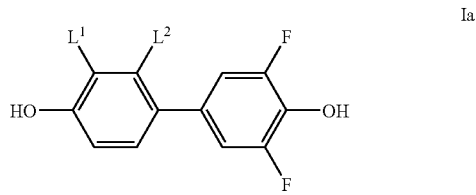

Ia in which $L^1$ and $L^2$ have the meanings indicated in formula I.

The invention furthermore relates to an LC medium comprising one or more polymerizable compounds of the formula I and one or more additional compounds, which may also be mesogenic, liquid-crystalline and/or polymerisable.

The invention furthermore relates to an LC medium comprising
  a polymerizable component A) comprising one or more polymerizable compounds of the formula I, and
  a liquid-crystalline component B), also referred to below as "LC host mixture", comprising one or more, preferably two or more, low-molecular-weight (i.e. monomeric or unpolymerized) compounds as described above and below.

The LC media according to the invention preferably comprises <5% by weight, particularly preferably <1% by weight, very particularly preferably <0.5% by weight, of polymerizable component A, based on the total amount polymerizable compounds and low-molecular-weight (i.e., monomeric or unpolymerized) liquid-crystalline compounds in the LC medium. Additionally, the LC media according to the invention preferably comprises <95% by weight, particularly preferably <99% by weight, very particularly preferably <99.5% by weight, of liquid-crystalline component B, based on the total amount polymerizable compounds and low-molecular-weight (i.e. monomeric or unpolymerized) liquid-crystalline compounds in the LC medium.

The invention furthermore relates to a polymer obtainable by polymerization of one or more compounds of the formula I or of an LC medium according to the invention.

The invention furthermore relates to a polymer film obtainable by polymerization of a layer comprising one or more compounds of the formula I or an LC medium according to the invention, in the uniformly aligned state in the LC phase, preferably in the nematic or cholesteric phase.

The invention furthermore relates to the use of compounds of the formula I, LC media, polymers and polymer films according to the invention in electro-optical displays, LC displays, optical films, polarizers, compensators, beam splitters, reflective polarizers, alignment layers, colored filters, holographic elements, heat-sealing films, adhesion films, optical data storage media, in nonlinear optics, effect pigments, decorative elements, security elements, security markings, electrical semiconductors, organic field-effect transistors (OFETs), integrated circuits (ICs), thin-film transistors (TFTs), radio frequency identification elements (RFIDs), organic light-emitting diodes (OLEDs), electroluminescent displays, illumination elements, photovoltaic devices, optical sensors, photoconductors, electro-photographic applications, or cosmetic formulations or applications.

The invention furthermore relates to the use of compounds of the formula I, LC media and polymers according to the invention in PS and PSA displays. The invention furthermore relates to an LC display containing one or more compounds of the formula I or an LC medium according to the invention, in particular a PS or PSA display, particularly preferably a PSA-VA, PSA-OCB, PS-IPS, PS-FFS or PS-TN display.

The invention furthermore relates to a PS or PSA display containing an LC cell comprising two substrates, where at least one substrate transmits light and at least one substrate has an electrode layer, and a layer of an LC medium comprising a polymerized component and a low-molecular-weight component which is located between the substrates, where the polymerized component is obtainable by polymerization of one or more polymerizable compounds between the substrates of the LC cell in the LC medium with application of an electrical voltage, characterized in that it contains one or more compounds of the formula I or an LC medium according to the invention.

Particularly preferred compounds of the formula I are those in which $R^a$ and $R^b$ denote identical or different radicals P-Sp-, $R^a$ and $R^b$ denote identical or different radicals P-Sp- in which one or both radicals Sp denote a single bond, one of the radicals $R^a$ and $R^b$ denotes or contains a P-Sp- group, and the other denotes an unpolymerizable group, preferably selected from straight-chain or branched alkyl having 1 to 25 C atoms, in which, in addition, one or more non-adjacent $CH_2$ groups may each be replaced, independently of one another, by —C($R^{00}$)=C($R^{00}$)—, —C≡C—, —N($R^{00}$)—, —O—, —S—, —CO—, —CO—O—, —O—CO—, —O—CO—O— in such a way that O and/or S atoms are not linked directly to one another, and in which, in addition, one or more H atoms may be replaced by F, Cl, Br, I or CN, $R^a$ denotes P-Sp-, $R^b$ denotes P-Sp-, Sp denotes a single bond.

Particularly preferred compounds of the formulae I and Ia are those in which at least one of the radicals $L^1$ and $L^2$ denotes F, in particular in which one of the radicals $L^1$ and $L^2$ denotes F and the other denotes H, $L^1$ denotes F and L2 denotes H, $L^1$ denotes H and L2 denotes F, $L^1$ and $L^2$ denote F.

Particularly preferred compounds of the formula I are selected from the following sub-formulae:

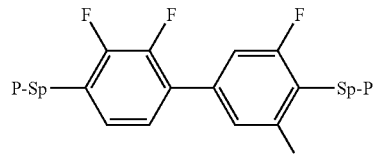

I1

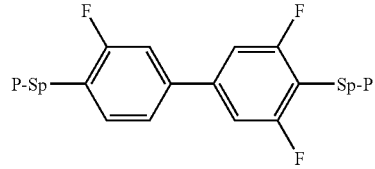

I2

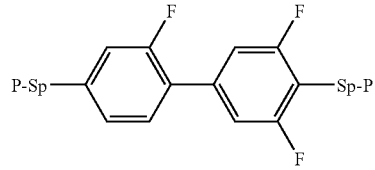

I3

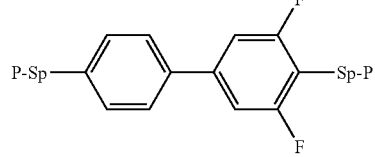

I4 in which P and Sp each, independently of one another, have one of the meanings indicated above and below.

Particularly preferred compounds of the formula Ia are selected from the following sub-formulae:

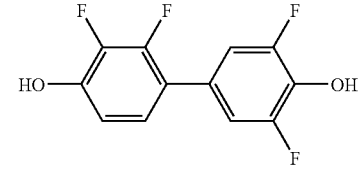

Ia1

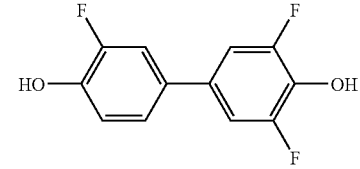

Ia2

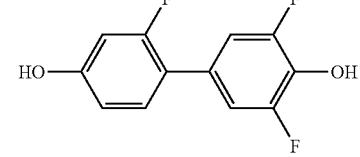

Ia3

-continued

Ia4

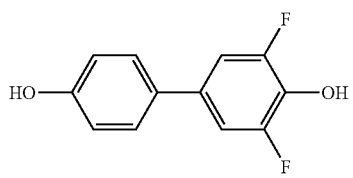

Above and below, the following meanings apply:

Unless indicated otherwise, the term "PSA" is used to represent PS displays and PSA displays.

The term "mesogenic group" is known to the person skilled in the art and is described in the literature, and denotes a group which, due to the anisotropy of its attracting and repelling interactions, essentially contributes to causing a liquid-crystal (LC) phase in low-molecular-weight or polymeric substances. Compounds containing mesogenic groups (mesogenic compounds) do not necessarily have to have an LC phase themselves. It is also possible for mesogenic compounds to exhibit LC phase behavior only after mixing with other compounds and/or after polymerization. Typical mesogenic groups are, for example, rigid rod- or disc-shaped units. An overview of the terms and definitions used in connection with mesogenic or LC compounds is given in Pure Appl. Chem. 73(5), 888 (2001) and C. Tschierske, G. Pelzl, S. Diele, Angew. Chem. 2004, 116, 6340-6368.

The term "spacer group", also referred to as "Sp" above and below, is known to the person skilled in the art and is described in the literature, see, for example, Pure Appl. Chem. 73(5), 888 (2001) and C. Tschierske, G. Pelzl, S. Diele, Angew. Chem. 2004, 116, 6340-6368. Unless indicated otherwise, the term "spacer group" or "spacer" above and below denotes a flexible group which connects the mesogenic group and the polymerizable group(s) to one another in a polymerizable mesogenic compound ("RM").

Preferred radicals $R^a$ and $R^b$ are optionally substituted alkyl, alkenyl, alkynyl, alkoxy, alkylcarbonyl, alkoxycarbonyl, alkylcarbonyloxy and alkoxycarbonyloxy having up to 20, preferably up to 12, C atoms.

Preferred alkyl groups are, for example, methyl, ethyl, n-propyl, isopropyl, n-butyl, isobutyl, s-butyl, t-butyl, 2-methylbutyl, n-pentyl, s-pentyl, cyclopentyl, n-hexyl, cyclohexyl, 2-ethylhexyl, n-heptyl, cycloheptyl, n-octyl, cyclooctyl, n-nonyl, n-decyl, n-undecyl, n-dodecyl, dodecanyl, trifluoromethyl, perfluoro-n-butyl, 2,2,2-trifluoroethyl, perfluorooctyl, perfluorohexyl, etc.

Preferred alkenyl groups are, for example, ethenyl, propenyl, butenyl, pentenyl, cyclopentenyl, hexenyl, cyclohexenyl, heptenyl, cycloheptenyl, octenyl, cyclooctenyl, etc.

Preferred alkynyl groups are, for example, ethynyl, propynyl, butynyl, pentynyl, hexynyl, octynyl, etc.

Preferred alkoxy groups are, for example, methoxy, ethoxy, 2-methoxy-ethoxy, n-propoxy, i-propoxy, n-butoxy, i-butoxy, s-butoxy, t-butoxy, 2-methylbutoxy, n-pentoxy, n-hexoxy, n-heptyloxy, n-octyloxy, n-nonyloxy, n-decyloxy, n-undecyloxy, n-dodecyloxy, etc.

The polymerizable group P is a group which is suitable for a polymerization reaction, such as, for example, free-radical or ionic chain polymerization, polyaddition or polycondensation, or for a polymer-analogous reaction, for example addition or condensation onto a main polymer chain. Particular preference is given to groups for chain polymerization, in particular those containing a C=C double bond or C≡C triple bond, and groups which are suitable for polymerization with ring opening, such as, for example, oxetane or epoxide groups.

Preferred groups P are selected from $CH_2=CW^1-COO-$, $CH_2=CW^1-CO-$,

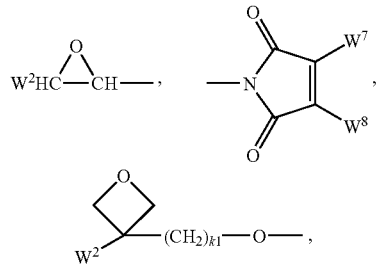

$CH_2=CW^2-(O)_{k3}-$, $CH_3-CH=CH-O-$, $(CH_2=CH)_2CH-OCO-$, $(CH_2=CH-CH_2)_2CH-OCO-$, $(CH_2=CH)_2CH-O-$, $(CH_2=CH-CH_2)_2N-$, $(CH_2=CH-CH_2)_2N-CO-$, $HO-CW^2W^3-$, $HS-CW^2W^3-$, $HW^2N-$, $HO-CW^2W^3-NH-$, $CH_2=CW^1-CO-NH-$, $CH_2=CH-(COO)_{k1}-Phe-(O)_{k2}-$, $CH_2=CH-(CO)_{k1}-Phe-(O)_{k2}-$, $Phe-CH=CH-$, $HOOC-$, $OCN-$ and $W^4W^5W^6Si-$, in which $W^1$ denotes H, F, Cl, CN, $CF_3$, phenyl or alkyl having 1 to 5 C atoms, in particular H, F, Cl or $CH_3$, $W^2$ and $W^3$ each, independently of one another, denote H or alkyl having 1 to 5 C atoms, in particular H, methyl, ethyl or n-propyl, $W^4$, $W^5$ and $W^6$ each, independently of one another, denote Cl, oxaalkyl or oxacarbonylalkyl having up to 5 C atoms, $W^7$ and $W^8$ each, independently of one another, denote H, Cl or alkyl having 1 to 5 C atoms, Phe denotes 1,4-phenylene, which is optionally substituted by one or more radicals L as defined below, and $k_1$, $k_2$ and $k_3$ each, independently of one another, denote 0 or 1, $k_3$ preferably denotes 1.

L is F, Cl, Br, I, $-CN$, $-NO_2$, $-NCO$, $-NCS$, $-OCN$, $-SCN$, $-C(=O)N(R^{00})_2$, $-C(=O)R^{00}$, $-N(R^{00})_2$, optionally substituted silyl, optionally substituted aryl having 6 to 20 C atoms, or straight-chain or branched alkyl, alkoxy, alkylcarbonyl, alkoxycarbonyl, alkylcarbonyloxy or alkoxycarbonyloxy having up to 25 C atoms, in which, in addition, one or more H atoms may be replaced by F or Cl, and $R^{00}$ is H or alkyl having 1 to 12 C atoms.

Particularly preferred groups P are $CH_2=CW^1-COO-$, in particular $CH_2=CH-COO-$, $CH_2=C(CH_3)-COO-$ and $CH_2=CF-COO-$, furthermore $CH_2=CH-O-$, $(CH_2=CH)_2CH-OCO-$, $(CH_2=CH)_2CH-O-$,

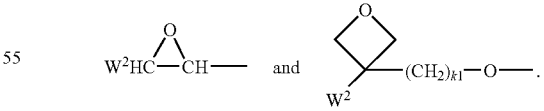

Very particularly preferred groups P are vinyloxy, acrylate, methacrylate, fluoroacrylate, chloroacrylate, oxetane and epoxide.

Preferred spacer groups Sp are selected from the formula Sp'-X', so that the radical P-Sp- corresponds to the formula P-Sp'-X'—, where Sp' denotes alkylene having 1 to 20, preferably 1 to 12, C atoms, which is optionally mono- or polysubstituted by F, Cl, Br, I or CN and in which, in addition, one or more non-adjacent CH$_2$ groups may each be replaced, independently of one another, by —O—, —S—, —NH—, —NR$^{00}$—, —SiR$^{00}$R$^{000}$—, —CO—, —COO—, —OCO—, —OCO—O—, —S—CO—, —CO—S—, —NR$^{00}$—CO—O—, —O—CO—NR$^{00}$—, —NR$^{00}$—CO—NR$^{00}$—, —CH=CH— or —C≡C— in such a way that O and/or S atoms are not linked directly to one another, X' denotes —O—, —S—, —CO—, —COO—, —OCO—, —O—COO—, —CO—NR$^{00}$—, —NR$^{00}$—CO—, —NR$^{00}$—CO—NR$^{00}$—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH=N—, —N=OH—, —N=N—, —CH=CR$^{00}$—, —CY$^2$=CY$^3$—, —C≡C—, —CH=CH—COO—, —OCO—CH=CH— or a single bond, R$^{00}$ and R$^{000}$ each, independently of one another, denote H or alkyl having 1 to 12 C atoms, and Y$^2$ and Y$^3$ each, independently of one another, denote H, F, Cl or CN.

X' is preferably —O—, —S—, —CO—, —COO—, —OCO—, —O—COO—, —CO—NR$^{00}$—, —NR$^{00}$—CO—, —NR$^{00}$—CO—NR$^{00}$— or a single bond.

Typical spacer groups Sp' are, for example, —(CH$_2$)$_{p1}$—, —(CH$_2$CH$_2$O)$_{q1}$—CH$_2$CH$_2$—, —CH$_2$CH$_2$—S—CH$_2$CH$_2$—, —CH$_2$CH$_2$—NH—CH$_2$CH$_2$— or —(SiR$^{00}$R$^{000}$—O)$_{p1}$—, in which p1 is an integer from 1 to 12, q1 is an integer from 1 to 3, and R$^{00}$ and R$^{000}$ have the above-mentioned meanings.

Particularly preferred groups —X'-Sp'- are —(CH$_2$)$_{p1}$—, —O—(CH$_2$)$_{p1}$—, —OCO—(CH$_2$)$_{p1}$—, —OCOO—(CH$_2$)$_{p1}$—.

Particularly preferred groups Sp' are, for example, in each case straight-chain ethylene, propylene, butylene, pentylene, hexylene, heptylene, octylene, nonylene, decylene, undecylene, dodecylene, octadecylene, ethyleneoxyethylene, methyleneoxybutylene, ethylenethioethylene, ethylene-N-methyliminoethylene, 1-methylalkylene, ethenylene, propenylene and butenylene.

In a further preferred embodiment of the invention, R$^a$ and/or R$^b$ in formula I denote a radical containing two or more polymerizable groups (multifunctional polymerizable radicals). Suitable radicals of this type, and polymerizable compounds containing them and the preparation thereof, are described, for example, in U.S. Pat. No. 7,060,200 B1 or US 2006/0172090 A1. Particular preference is given to multifunctional polymerizable radicals selected from the following formulae:

| | |
|---|---|
| —X-alkyl-CHP$^1$—CH$_2$—CH$_2$P$^2$ | I*a |
| —X-alkyl-C(CH$_2$P$^1$)(CH$_2$P$^2$)—CH$_2$P$^3$ | I*b |
| —X-alkyl-CHP$^1$CHP$^2$—CH$_2$P$^3$ | I*c |
| —X-alkyl-C(CH$_2$P$^1$)(CH$_2$P$^2$)—C$_{aa}$H$_{2aa+1}$ | I*d |
| —X-alkyl-CHP$^1$—CH$_2$P$^2$ | I*e |
| —X-alkyl-CHP$^1$P$^2$ | I*f |
| —X-alkyl-CP$^1$P$^2$—C$_{aa}$H$_{2aa+1}$ | I*g |
| —X-alkyl-C(CH$_2$P$^1$)(CH$_2$P$^2$)—CH$_2$OCH$_2$—C(CH$_2$P$^3$)(CH$_2$P$^4$)CH$_2$P$^5$ | I*h |
| —X-alkyl-CH((CH$_2$)$_{aa}$P$^1$)((CH$_2$)$_{bb}$P$^2$) | I*i |
| —X-alkyl-CHP$^1$CHP$^2$—C$_{aa}$H$_{2aa+1}$ | I*k |
| —X'-alkyl-C(CH$_3$)(CH$_2$P$^1$)(CH$_2$P$^2$) | I*m | in which alkyl denotes a single bond or straight-chain or branched alkylene having 1 to 12 C atoms, in which one or more non-adjacent CH$_2$ groups may each be replaced, independently of one another, by —C(R$^{00}$)=C(R$^{000}$)—, —C≡C—, —N(R$^{00}$)—, —O—, —S—, —CO—, —CO—O—, —O—CO—, —O—CO—O— in such a way that O and/or S atoms are not linked directly to one another, and in which, in addition, one or more H atoms may be replaced by F, Cl or CN, where R$^{00}$ and R$^{000}$ have the meaning indicated above, aa and bb each, independently of one another, denote 0, 1, 2, 3, 4, 5 or 6, X has one of the meanings indicated for X', and P$^{1-5}$ each, independently of one another, have one of the meanings indicated for P.

The compounds of the formulae I and Ia can be prepared analogously to processes known to the person skilled in the art and described in standard works of organic chemistry, such as, for example, in Houben-Weyl, Methoden der organischen Chemie [Methods of Organic Chemistry], Thieme-Verlag, Stuttgart. The synthesis of polymerizable compounds of the formula I in which P denotes an acrylate group or an acrylate derivative (such as, for example, methacrylate) can be carried out analogously to the methods described in U.S. Pat. No. 5,723,066. Preferred methods are given in the examples. For example, the synthesis of compounds of the formula I is carried out by esterification or etherification of diols of the formula Ia, such as, for example, 2,3,3',5'-tetrafluoro-4,4'-dihydroxybiphenyl, using corresponding acids, acid derivatives, or halogenated compounds containing a group P, such as, for example, (meth)acryloyl chloride or (meth)acrylic acid, in the presence of a dehydrating reagent, such as, for example, DCC (dicyclohexylcarbodiimide).

A particularly preferred process for the preparation of compounds of the formula Ia1 is shown by way of example in Scheme 1 and comprises the following steps:

a) reaction of the OH group of 2,3-difluorophenol (1) with a protecting group, for example a trialkylsilyl ether, b) metallation of the product (2) from step a) in the para-position to the protected phenol group and subsequent reaction with a boronic acid or a boronic acid ester, c) coupling of the product (3) from step b) to 4-halo-2,6-difluorophenol (4) in the presence of a transition-metal catalyst and removal of the protecting group to give 2,3,3',5'-tetrafluorobiphenyl-4,4'-diol (5).

Scheme 1

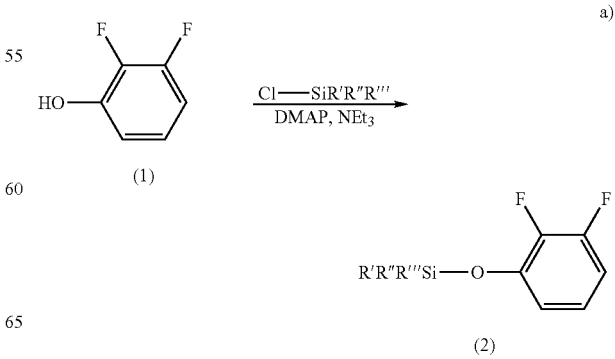

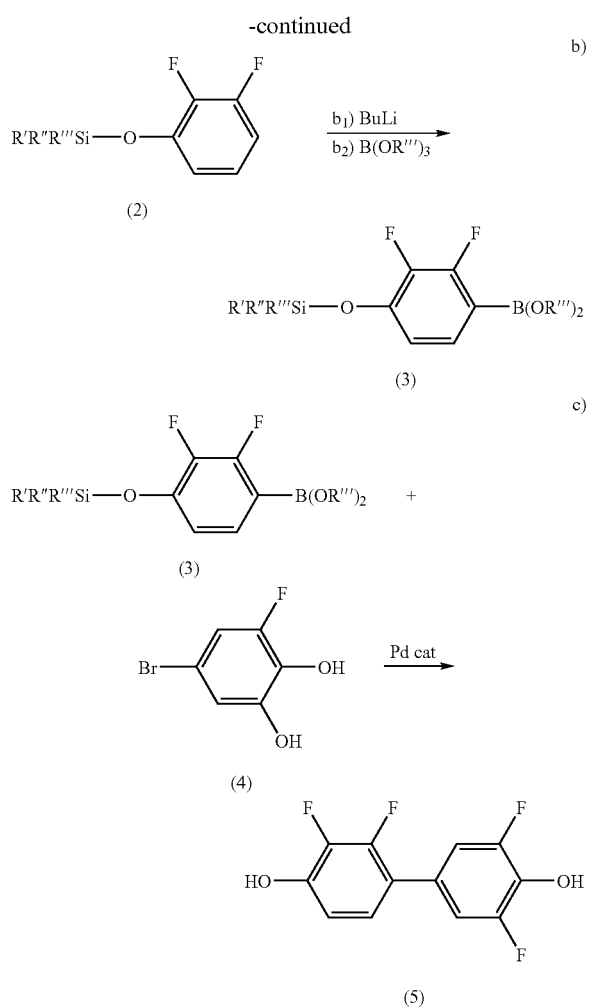

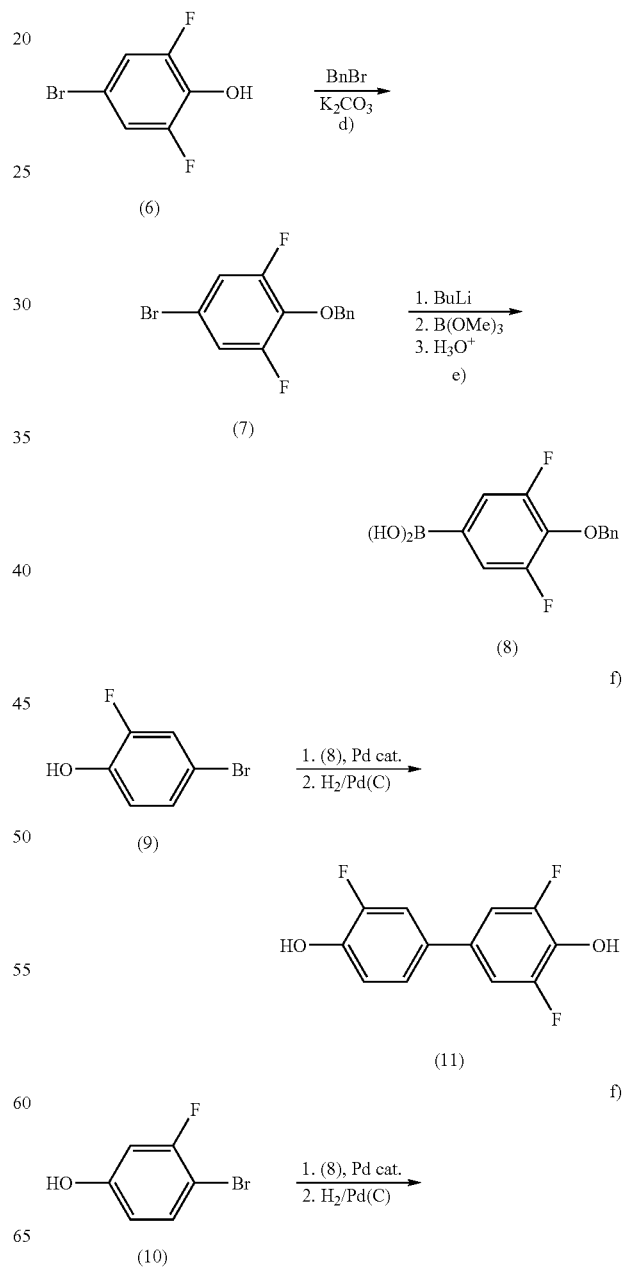

A particularly preferred process for the preparation of the compounds of the formulae Ia2 and Ia3 is shown by way of example in Scheme 2 and comprises the following steps:

d) reaction of the OH group of 4-halo-2,6-difluorophenol (6) with a protecting group, for example a benzyl halide, e) dehalogenation of the product (7) from step d) in the para-position to the protected phenol ether group and subsequent reaction with a boronic acid or a boronic acid ester, f) coupling of the product (8) from step e) to 4-halo-2-fluorophenol (9) or 4-halo-3-fluorophenol (10) in the presence of a transition-metal catalyst and removal of the protecting group to give 2,3',5'-trifluorobiphenyl-4,4'-diol (11) or 3,3', 5'-trifluorobiphenyl-4,4'-diol (12) respectively.

In these formulae, R', R''=alkyl, for example methyl; R'''=alkyl, for example t-butyl; R''''=H or alkyl; two radicals OR'''' may also, together with the boron atom, form a cyclic radical; DMAP=dimethylaminopyridine; NEt₃=triethylamine; BuLi=n-butyllithium; Pd cat=Pd(II) catalyst, for example bis(triphenylphosphino)palladium(II) chloride.

The protection of the phenol group in step a) can be carried out, for example, by etherification using trialkylchlorosilane. In step b), a boronic acid or an open-chain or cyclic boronic acid ester can be used. The halide (4) in step c) is, for example, 4-bromo-2,6-difluorophenol, but it is also possible to use an iodide or another suitable leaving group having comparable reactivity (such as, for example, triflate) instead of the bromide. The transition-metal catalyst employed in step c) is preferably a palladium complex in oxidation state 0, II or IV. The reaction is preferably carried out in the homogeneous phase with a soluble catalyst. A preferred complex is, for example, bis(triphenylphosphine)palladium(II) chloride.

As an alternative to the processes described above and below, the reactive groups of the reactants (3) and (4) (boronic acid derivative and halide) may also be exchanged, or 2,6-difluorophenol is used instead of compound (1) in step a) and 4-bromo (or iodo)-2,3-difluorophenol is used instead of compound (4) in step c).

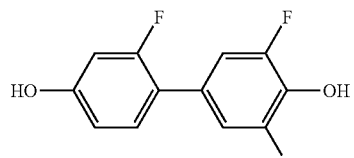

(12)

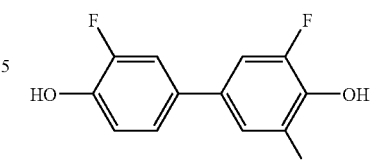

(11)

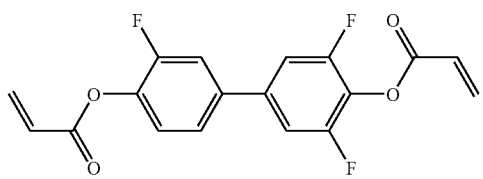

(15)

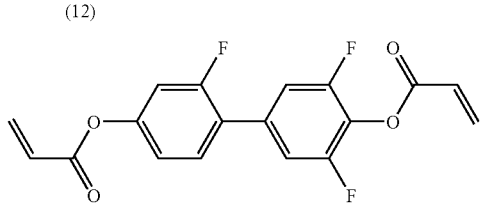

(16)

In these formulae, Bn=benzyl; BuLi=n-butyllithium; Pd cat=Pd(II) catalyst, for example bis(triphenylphosphino)palladium(II) chloride.

In step e), a boronic acid or an open-chain or cyclic boronic acid ester can be used. The halide (4) in step f) is, for example, 4-bromo-2- or -3-fluorophenol, but it is also possible to use an iodide or another suitable leaving group having comparable reactivity (such as, for example, triflate) instead of the bromide. The transition-metal catalyst employed in step f) is preferably a palladium complex in oxidation state 0, II or IV. The reaction is preferably carried out in the homogeneous phase with a soluble catalyst. A preferred complex is, for example, bis(triphenylphosphine)palladium(II)-chloride.

As an alternative to the processes described above and below, the reactive groups of the reactants (8) and (9) or (8) and (10) (boronic acid derivative and halide) may also be exchanged, or 4-Br (or iodo)-2 (or -3)-fluorophenol is used instead of compound (6) in step d), and 4-Br (or iodo)-2,6-difluorophenol is used instead of compound (9) or (10) in step f).

The preparation of compounds of the formula I from compounds of the formula Ia is preferably carried out by a process as shown by way of example in Scheme 3, comprising either step g) or h):

g) reaction of the phenolic OH groups with chloropropionyl chloride and subsequent elimination of HCl, or
h) etherification or esterification of the phenolic OH groups using an acid, an acid derivative or a halogenated compound containing a group P.

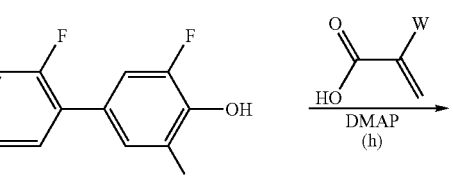

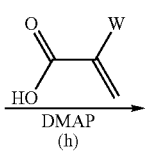

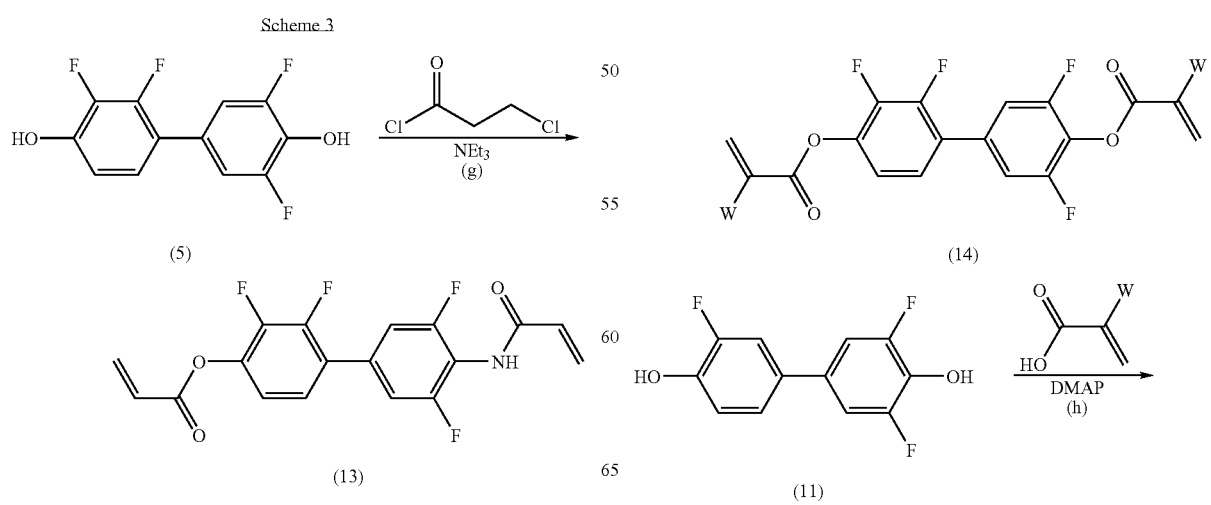

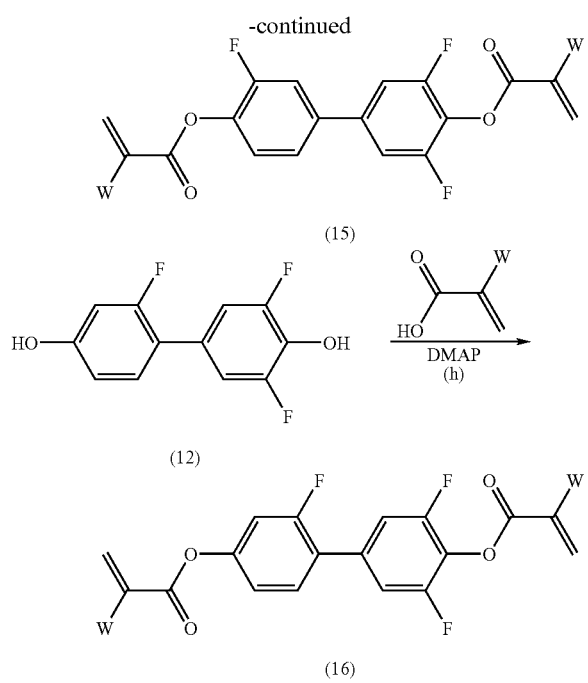

In these formulae, W=H, $CH_3$, F or Cl.

Acids, acid derivatives or halogenated compounds containing a group P which are suitable for step h) are, for example, acrylic acid, methacrylic acid, fluoroacrylic acid or chloroacrylic acid, or corresponding acid derivatives, for example the acid chloride.

For the production of PS(A) displays, the polymerizable compounds are polymerized or crosslinked (if a compound contains two or more polymerizable groups) by in-situ polymerization in the LC medium between the substrates of the LC display with application of a voltage. Suitable and preferred polymerization methods are, for example, thermal or photopolymerization, preferably photopolymerization, in particular UV photopolymerization. If necessary, one or more initiators may also be added here. Suitable conditions for the polymerization, and suitable types and amounts of initiators, are known to the person skilled in the art and are described in the literature. Suitable for free-radical polymerization are, for example, the commercially available photoinitiators Irgacure651®, Irgacure184® or Darocure1173® (Ciba AG). If an initiator is employed, its proportion is preferably 0.001 to 5% by weight, particularly preferably 0.001 to 1% by weight. However, the polymerization can also take place without addition of an initiator. In a further preferred embodiment, the LC medium does not comprise a polymerization initiator.

The polymerizable component A) or the LC medium may also comprise one or more stabilizers in order to prevent undesired spontaneous polymerization of the RMs, for example during storage or transport. Suitable types and amounts of stabilizers are known to the person skilled in the art and are described in the literature. Particularly suitable are, for example, the commercially available stabilizers of the Irganox® series (Ciba AG). If stabilizers are employed, their proportion, based on the total amount of the RMs or the polymerizable component A), is preferably 10-5000 ppm, particularly preferably 50-500 ppm.

The polymerizable compounds according to the invention are also suitable for polymerization without initiator, which is associated with considerable advantages, such as, for example, lower material costs and in particular less contamination of the LC medium by possible residual amounts of the initiator or degradation products thereof.

The LC media according to the invention for use in PSA displays preferably comprise <5% by weight, particularly preferably <1% by weight, very particularly preferably <0.5% by weight, of polymerizable compounds, in particular polymerizable compounds of the above-mentioned formulae.

Particular preference is given to LC media comprising one, two or three polymerizable compounds of the formula I.

Preference is furthermore given to LC media in which the polymerizable component A) consists exclusively of polymerizable compounds of the formula I.

Preference is furthermore given to LC media in which component B) is an LC compound or an LC mixture which has a nematic liquid-crystal phase.

Preference is furthermore given to achiral polymerizable compounds of the formula I and to LC media comprising, preferably consisting exclusively of, achiral compounds.

Preference is furthermore given to LC media in which the polymerizable component or component A) comprises one or more polymerizable compounds containing one polymerizable group (monoreactive) and one or more polymerizable compounds containing two or more, preferably two, polymerizable groups (di- or multireactive).

Preference is furthermore given to PS(A) displays and LC media in which the polymerizable component or component A) consists exclusively of polymerizable compounds containing two polymerizable groups (direactive).

The polymerizable compounds of the formula I can be polymerized individually, but it is also possible to polymerise mixtures which comprise two or more compounds of the formula I, or mixtures comprising one or more compounds of the formula I and one or more further polymerizable compounds (comonomers), which are preferably mesogenic or liquid-crystalline. Polymerization of mixtures of this type gives copolymers. The invention furthermore relates to the polymerizable mixtures mentioned above and below. The polymerizable compounds and comonomers are mesogenic or non-mesogenic, preferably mesogenic or liquid-crystalline.

Suitable and preferred mesogenic comonomers, particularly for use in PS(A) displays, are, for example, selected from the following formulae:

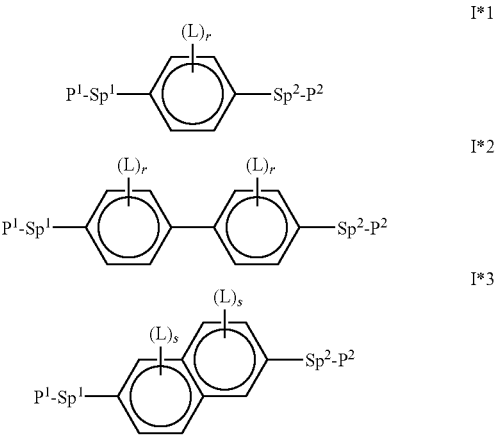

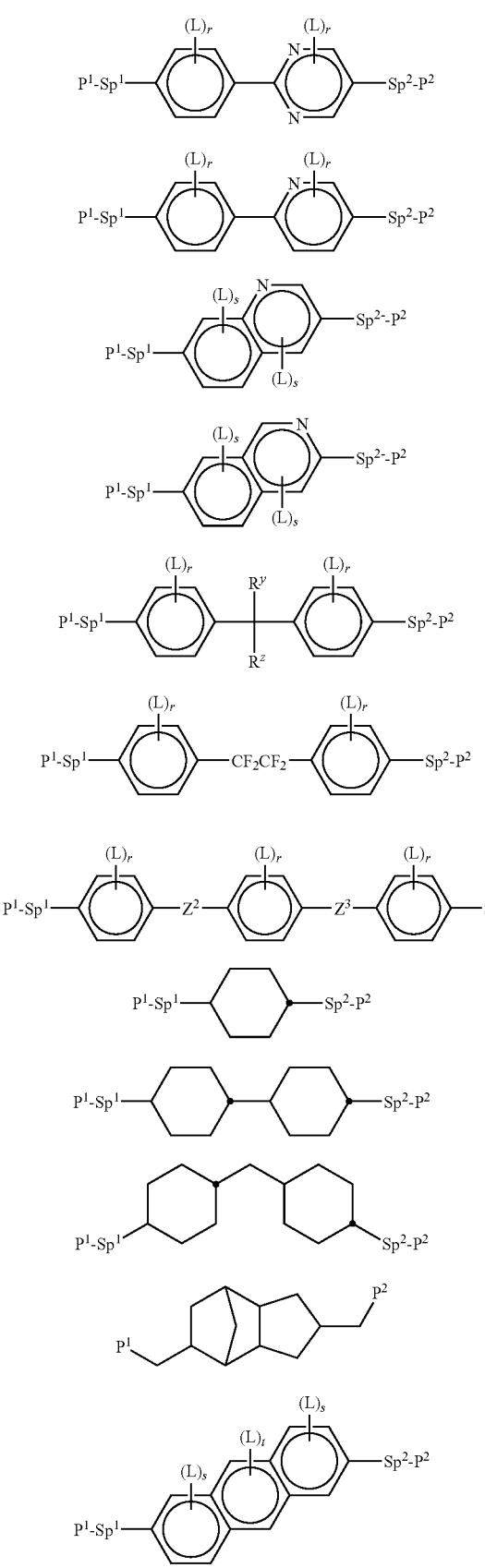

in which
P¹ and P² have one of the meanings indicated for P and preferably denote acrylate or methacrylate,
Sp¹ and Sp² have one of the meanings indicated for Sp or denote a single bond,
$Z^2$ and $Z^3$ each, independently of one another, denote —COO— or —OCO—,
L denotes P-Sp-, F, Cl, Br, I, —CN, —NO$_2$, —NCO, —NCS, —OCN, —SCN, —C(=O)N(R$^{00}$)$_2$, —C(=O)R$^{00}$, —N(R$^{00}$)$_2$, optionally substituted silyl, optionally substituted aryl having 6 to 20 C atoms, or straight-chain or branched alkyl, alkoxy, alkylcarbonyl, alkoxycarbonyl, alkylcarbonyloxy or alkoxycarbonyloxy having up to 25 C atoms, in which, in addition, one or more H atoms may be replaced by F, Cl or P-Sp-,
L' and L" each, independently of one another, denote H, F or Cl,
r denotes 0, 1, 2, 3 or 4,
s denotes 0, 1, 2 or 3,
t denotes 0, 1 or 2,
x denotes 0 or 1, and
$R^y$ and $R^z$ each, independently of one another, denote H or CH$_3$.

A further use relates to polymers obtainable by polymerization of one or more compounds of the formula I or of a polymerizable LC medium according to the invention, in particular polymer films or foils obtainable by polymerization of a layer comprising one or more compounds of the formula I or an LC medium according to the invention, in the uniformly aligned state in the LC phase.

For this use too, the compounds of the formula I can be polymerized individually or in a mixture comprising two or more compounds of the formula I, or one or more compounds of the formula I and one or more further comonomers, preferably mesogenic or liquid-crystalline comonomers (RMs). The compounds of the formula I and/or the comonomers or RMs may be monoreactive, di- or multireactive The polymers and polymer films are particularly suitable for use as optical films, such as polarizers, compensators, beam splitters or reflective polarizers, furthermore as alignment layers, colored filters, holographic elements or heat-sealing films, for the preparation of effect pigments having angle-dependent selective reflection, for decorative elements, or in security elements or security markings for forgery-proof documents, identity cards or securities.

RMs which are suitable as comonomers are known to the person skilled in the art or can be prepared by methods known per se which are described in standard works of organic chemistry, such as, for example, Houben-Weyl, Methoden der organischen Chemie [Methods of Organic Chemistry], Thieme-Verlag, Stuttgart. Typical examples of suitable RMs are disclosed in WO 93/22397, EP 0 261 712, DE 195 04 224, WO 95/22586, WO 97/00600, U.S. Pat. No. 5,518,652, U.S. Pat. No. 5,750,051, U.S. Pat. No. 5,770,107 and U.S. Pat. No. 6,514,578. Further examples of particularly suitable and preferred mono-reactive (MR), direactive (DR) and chiral (CR) RMs are shown in the following list:

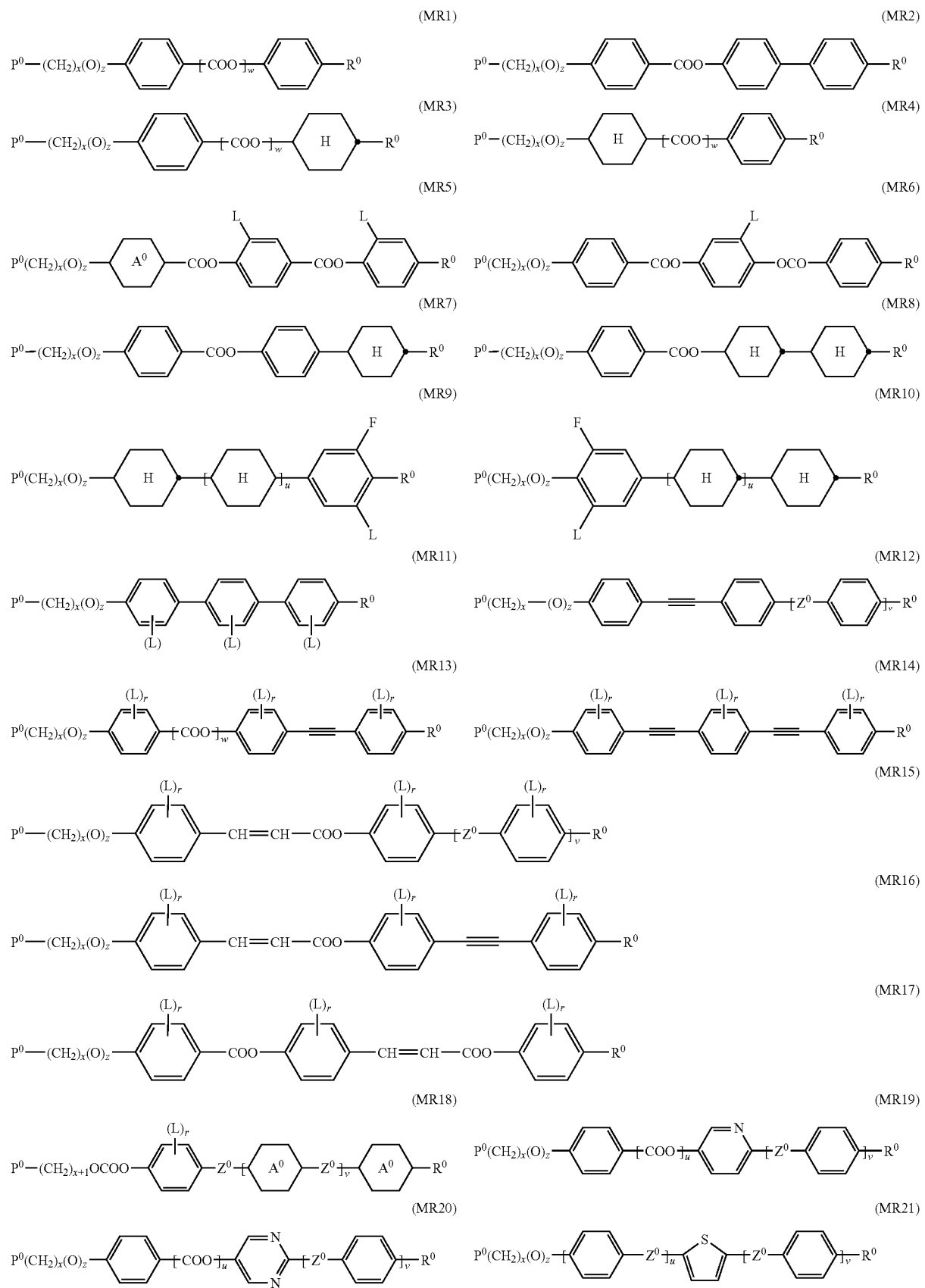

-continued
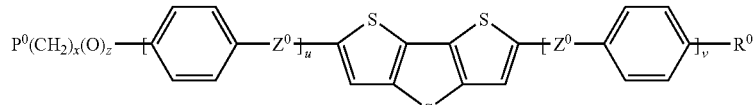
(MR22)
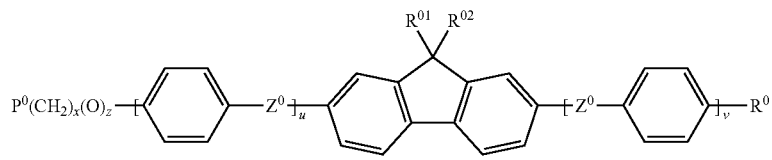
(MR23)
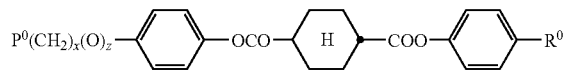
(MR24)
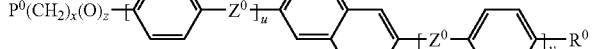
(MR25)
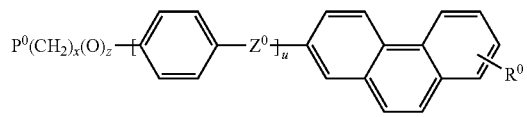
(MR26)
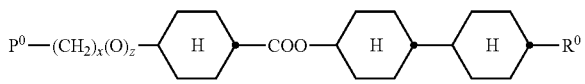
(MR27)
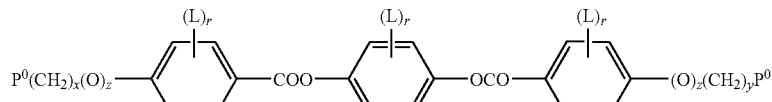
(DR1)
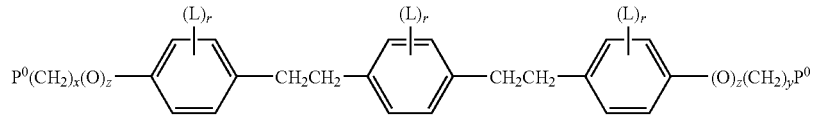
(DR2)
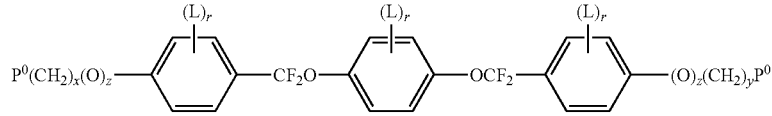
(DR3)
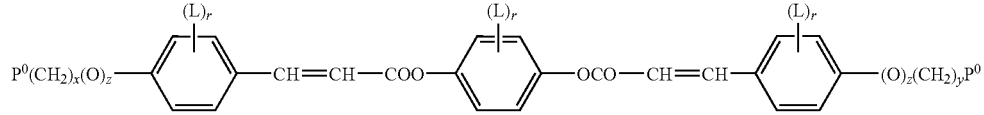
(DR4)
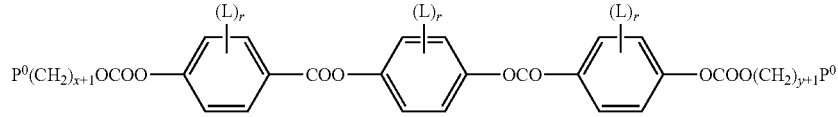
(DR5)
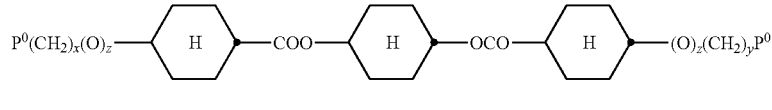
(DR6)
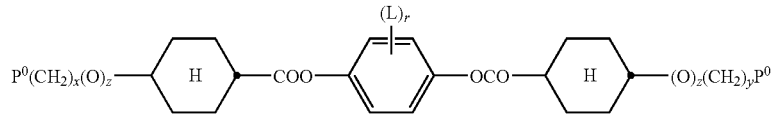
(DR7)
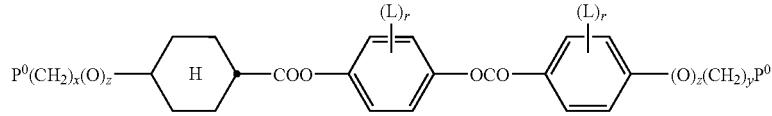
(DR8)

-continued
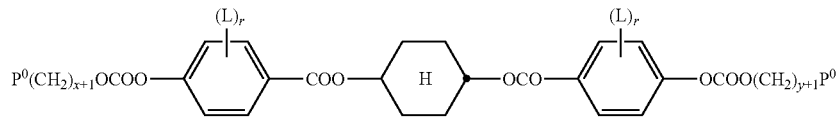 (DR9)
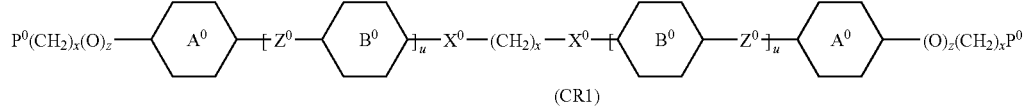 (DR10)
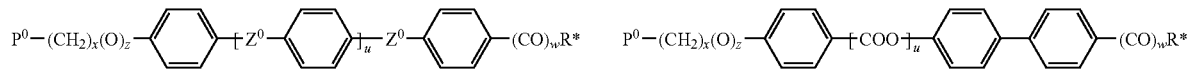
(CR1) (CR2)
(CR3)
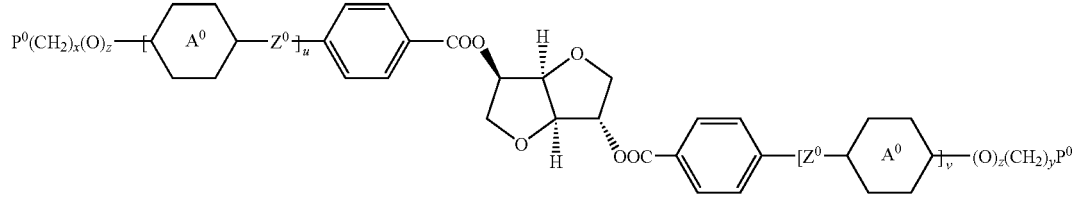 (CR4)
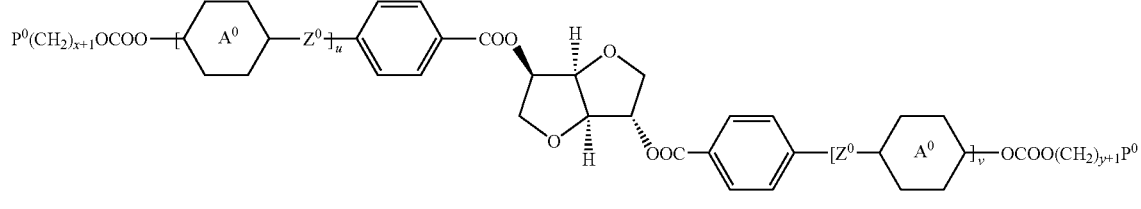 (CR5)
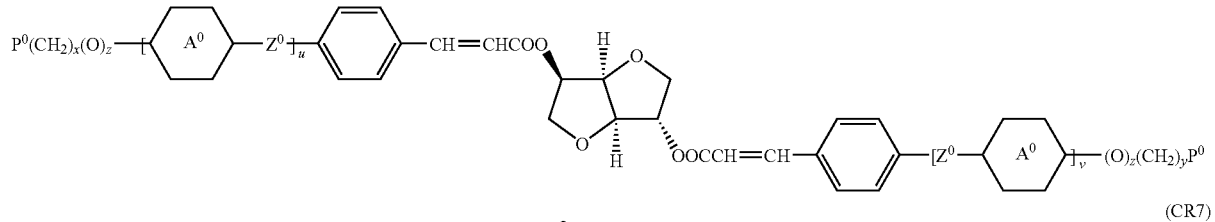 (CR6)
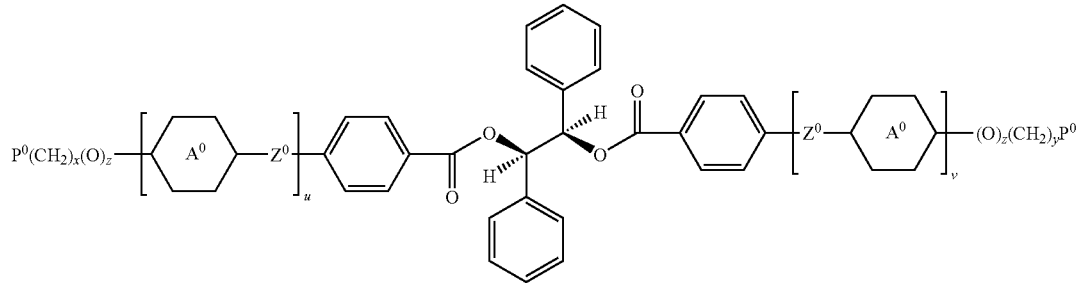 (CR7)
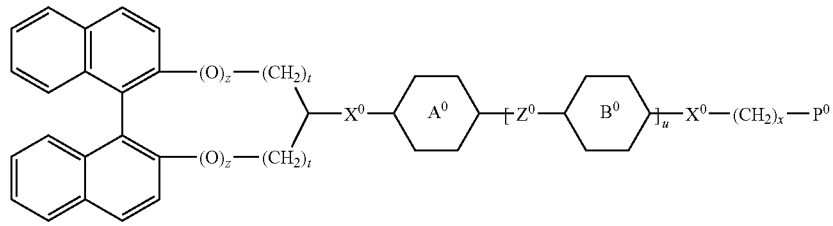 (CR8)

in which the individual radicals, in each case independently of one another and, if they occur more than once, identically or differently, have the following meanings:

$P^o$ denotes a polymerizable group, preferably selected from acryloyl, methacryloyl, oxetane, epoxide, vinyloxy and styryl, $A^o$ and $B^o$ denote 1,4-phenylene, which is optionally substituted by 1, 2, 3 or 4 radicals L, or trans-1,4-cyclohexylene, $Z^o$ denotes —COO—, —OCO—, —CH$_2$CH$_2$—, —C≡C—, —CH=CH—, —CH=CH—COO—, —OCO—CH=CH— or a single bond, $R^o$ denotes alkyl, alkoxy, thioalkyl, alkylcarbonyl, alkoxycarbonyl, alkylcarbonyloxy or alkoxycarbonyloxy having 1 or more, preferably up to 15, C atoms, which is optionally mono- or polyfluorinated, or denotes $Y^o$ or $P^o$—(CH$_2$)$_y$—(O)$_z$—, $Y^o$ denotes F, Cl, CN, NO$_2$, OCH$_3$, OCN, SCN, NCO, NCS, SF$_5$, optionally fluorinated alkylcarbonyl, alkoxycarbonyl, alkylcarbonyloxy or alkoxycarbonyloxy having up to 4 C atoms, or mono-, oligo- or polyfluorinated alkyl or alkoxy having 1 to 4 C atoms, $R^{o1,o2}$ denote H, $R^o$ or $Y^o$, R* denotes chiral alkyl or alkoxy having 4 or more, preferably 4 to 12, C atoms, such as, for example, 2-methylbutyl, 2-methyloctyl, 2-methylbutoxy or 2-methyloctyloxy, Ch denotes a chiral group selected from cholesteryl, oestradiol and terpenoid radicals, such as, for example, menthyl or citronellyl, L denotes H, F, Cl, CN or optionally fluorinated or chlorinated alkyl, alkoxy, alkylcarbonyl, alkoxycarbonyl, alkylcarbonyloxy or alkoxycarbonyloxy having up to 4 C atoms, r denotes 0, 1, 2, 3 or 4, t denotes 0, 1, 2 or 3, u and v denote 0, 1 or 2, w denotes 0 or 1, x and y denote 0 or an integer from 1 to 12, z denotes 0 or 1, where z is 0 if x or y is 0 in the adjacent radical, and in which the benzene and naphthyl rings may also additionally be substituted by one or more identical or different radicals L.

The polymerizable mixtures according to the invention may also comprise one or more chiral compounds or chiral dopants and may also have chirally liquid-crystalline phases, such as, for example, a cholesteric phase. The chiral compounds can be polymerizable and/or mesogenic or liquid-crystalline. Suitable chiral RMs are, for example, those of the formulae CR1-CR8 shown above. Suitable chiral dopants are, for example, selected from the commercially available compounds cholesteryl nonanoate (CN), CB15, R/S-811, RS-1011, RIS-2011, R/S-3011 or R/S-4011 (Merck KGaA, Darmstadt). Particularly suitable dopants are those having a high twisting power, for example chiral sugar derivatives, in particular derivatives of dianhydrohexitols, such as isosorbitol, isomannitol or isoiditol, particularly preferably isosorbitol derivatives, as disclosed, for example, in WO 98/00428. Preference is furthermore given to hydrobenzoin derivatives, as described, for example, in GB 2,328,207, chiral binaphthyls, as described, for example, in WO 02/94805, chiral binaphthols, as described, for example, in WO 02/34739, chiral TADDOLs, as described, for example, in WO 02/06265, and chiral compounds containing a fluorinated bridging group and a terminal or central chiral group, as described, for example, in WO 02/06196 or WO 02/06195.

Suitable processes and aids for the preparation of liquid-crystalline polymers, polymer films or coatings are known to the person skilled in the art and are described in the literature, for example in D. J. Broer, G. Challa, G. N. Mol, Macromol. Chem, 1991, 192, 59. The polymers according to the invention are preferably prepared in the form of thin films. To this end, the polymerizable liquid-crystalline material is firstly, by way of assistance, applied to a substrate, for example by known coating or printing methods, from which the polymer film can then later be detached again if required. A uniform molecular alignment in the LC phase, for example in the nematic, smectic or cholesteric phase, is then induced in the material and fixed in situ by polymerization or crosslinking at a suitable temperature.

Suitable substrates are, for example, films or foils made from plastic, paper, board, leather, cellulose, textiles, glass, ceramic or metal. Suitable plastics are, for example, polyesters, such as polyethylene terephthalate (PET) or polyethylene naphthalate (PEN), polyvinyl alcohol (PVA), polycarbonate (PC), di- or triacetylcellulose (DAC, TAC), in particular PET, TAC, polyimides or polyamides which are employed in LC displays. The polymerizable material may also be covered by a second substrate Suitable coating methods are, for example, rolling, spraying, knife coating, spin coating or dipping, suitable printing methods are, for example, flexographic printing, offset printing, gravure printing, letterpress printing or ink-jet printing.

The polymerizable material can also be applied as a solution or suspension in an organic solvent, and the solvent can subsequently be removed, for example by warming and/or pressure reduction or application of a vacuum. Suitable solvents are, for example, toluene, xylene, MEK (methyl ethyl ketone), acetone, cyclohexanone, isopropyl alcohol, methyl, ethyl, propyl or butyl acetate, PGMEA (propylene glycol monomethyl ether acetate), or mixtures thereof.

A uniform alignment of the liquid-crystalline molecules can be achieved, for example, by applying an alignment layer, such as, for example, a polyimide layer or a layer of photo-aligned and crosslinked LC molecules, to the substrate surface to be coated. Suitable materials and methods for the application of alignment layers are described in the literature, for example in U.S. Pat. Nos. 5,602,661, 5,389,698 or 6,717,644. In addition or as an alternative, the substrate surface to be coated or the alignment layer can be rubbed in a preferential direction before application of the polymerizable material. Gentle shear of the polymerizable material between two substrates is frequently also sufficient for uniform alignment. Further methods for inducing or improving the uniform alignment are conditioning of the polymerizable material or application of an electric or magnetic field to the polymerizable material. In a further preferred embodiment, the polymerizable mixture comprises one or more additives, for example surface-active substances, which induce or improve the uniform alignment of the liquid-crystalline molecules on the substrate. Suitable substances are known to the person skilled in the art and are described in the literature, for example in J. Cognard, Mol.Cryst.Liq.Cryst. 78, Supplement 1, 1-77 (1981) or T. Uchida and H. Seki in "Liquid Crystals—Applications and Uses Vol. 3", B. Bahadur, World Scientific Publishing, Singapore 1992, pages 1-63. Particular preference is given to nonionic compounds, for example nonionic fluorinated hydrocarbons, such as the commercially available Fluorad FC-171® (3M), Zonyl FSN® (DuPont), or compounds as described in GB 2 383 040 A or EP 1 256 617 A1.

The polymerization or crosslinking of the polymerizable material is preferably carried out in situ, after application and alignment and optional conditioning in the LC phase, for example by thermal polymerization or by treatment with actinic radiation, such as, for example, UV light, IR light or visible light, X rays, gamma rays or high-energy particles, such as ions or electrons. Particular preference is given to photopolymerization, in particular polymerization using UV light. The radiation source used can be, for example, a single UV lamp or a series of UV lamps. Other possible radiation sources are, for example, lasers, such as UV lasers, IR lasers or lasers in the visible wavelength region.

The polymerization is preferably carried out in the presence of an initiator which absorbs the actinic radiation. In the case of UV photopolymerization, use is made, for example, of a photoinitiator which decomposes on UV irradiation and in the process liberates free radicals or ions which initiate a polymerization reaction. UV photoinitiators are particularly preferred. Photoinitiators of this type are known to the person skilled in the art and are commercially available, such as, for example, Irgacure® 907, Irgacure® 651, Irgacure® 184, Irgacure907®, Irgacure369®, Darocure® 1173 or Darocure® 4205 (Ciba AG) or UVI 6974 (Union Carbide). Particular preference is given for the preparation of polymers according to the invention to thermally or photochemically induced free-radical polymerization. The polymerizable material preferably comprises one or more initiators. The polymerizable material preferably comprises 0.01 to 10% by weight, particularly preferably 0.05 to 5% by weight, of initiators.

In a further preferred embodiment, the polymerizable material comprises one or more stabilizers in order to prevent undesired spontaneous polymerization, such as, for example, from the commercially available Irganox® series (Ciba Geigy A G, Basel, Switzerland).

In a further preferred embodiment, the polymerizable material comprises one or more chain-transfer reagents, for example thiol compounds, such as dodecanethiol or trimethylpropane tri(3-mercaptopropionate), in particular liquid-crystalline thiol compounds. Particular preference is given to mesogenic or liquid-crystalline thiol compounds, as disclosed, for example, in WO 96/12209 A1, WO 96/25470 A2 or U.S. Pat. No. 6,420,001. The addition of reagents of this type enables, for example, the free chain length of the polymers or the chain length between two crosslinking points to be reduced.

In a further preferred embodiment, the polymerizable material comprises one or more mono-, di- or multireactive polymerizable non-mesogenic compounds, such as, for example, alkyl(meth)acrylates or alkyl di(meth)-acrylates, preferably containing alkyl radicals containing 1 to 20 C atoms. Typical examples of suitable multireactive compounds are trimethylpropane trimethacrylate or pentaerythritol tetraacrylate. The polymerizable material preferably comprises 1 to 50% by weight, particularly preferably 2 to 20% by weight, of non-mesogenic polymerizable compounds of this type.

In a further preferred embodiment, the polymerizable material comprises one or more polymeric or polymerizable binders or dispersion assistants, as described, for example, in WO 96/02597.

In a further preferred embodiment, the polymerizable material comprises one or more components or assistants selected from the group comprising catalysts, sensitisers, stabilizers, chain-transfer reagents, inhibitors, comonomers, surface-active substances, plasticisers, wetting agents, dispersion assistants, flow-control agents, flow agents, viscosity reducers, hydrophobicizing agents, adhesion agents, antifoaming agents, aeration or degassing agents, thinners, reactive thinners, dyes, colorants, pigments and nanoparticles.

The polymer films and foils according to the invention preferably have a thickness of 0.3 to 10 microns, particularly preferably from 0.5 to 5 microns. For use as alignment layer, films having a thickness of 0.05 to 1, in particular 0.1 to 0.5, micron are preferred.

Besides the polymerizable compounds described above, the LC media for use in the LC displays according to the invention comprise an LC mixture ("host mixture") comprising one or more, preferably two or more, low-molecular-weight (i.e. monomeric or unpolymerized) compounds. The latter are stable or unreactive to a polymerization reaction under the conditions used for polymerization of the polymerizable compounds. In principle, a suitable host mixture is any LC mixture which is suitable for use in conventional VA or OCB displays. Suitable LC mixtures are known to the person skilled in the art and are described in the literature, for example mixtures in VA displays in EP 1 378 557 A1, and mixtures for OCB displays in EP 1 306 418 A1 and DE 102 24 046 A1. Particularly preferred host mixtures and LC media are mentioned below:

a) LC medium which comprises one or more compounds selected from the following formulae:

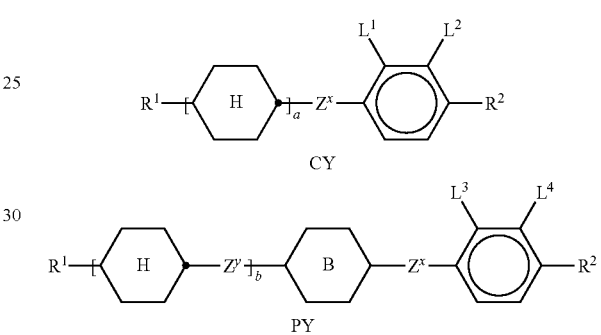

in which the individual radicals have the following meanings:
a denotes 1 or 2,
b denotes 0 or 1,

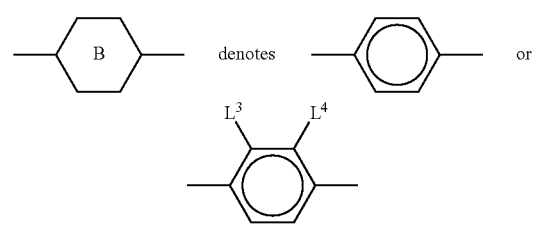

$R^1$ and $R^2$ each, independently of one another, denote alkyl having 1 to 12 C atoms, in which, in addition, one or two non-adjacent $CH_2$ groups may be replaced by —O—, —CH=CH—, —CO—, —OCO— or —COO— in such a way that O atoms are not linked directly to one another, preferably alkyl or alkoxy having 1 to 6 C atoms, $Z^x$ and $Z^y$ each, independently of one another, denote —$CH_2CH_2$—, —CH=CH—, —$CF_2O$—, —$OCF_2$—, —$CH_2O$—, —$OCH_2$—, —COO—, —OCO—, —$C_2F_4$—, —CF=CF—, —CH=CHCH$_2$O—, or a single bond, preferably a single bond, $L^{1-4}$ each, independently of one another, denote F, Cl, $OCF_3$, $CF_3$, $CH_3$, $CH_2F$, or $CHF_2$.

Preferably, both radicals $L^1$ and $L^2$ denote F or one of the radicals $L^1$ and $L^2$ denotes F and the other denotes Cl, or both radicals L³ and L⁴ denote F or one of the radicals L³ and L⁴ denotes F and the other denotes Cl.
The compounds of the formula CY are preferably selected from the following sub-formulae:
CY1
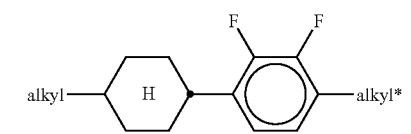
CY2
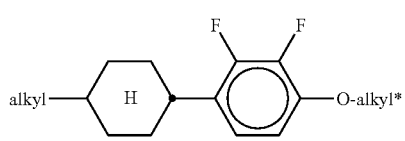
CY3
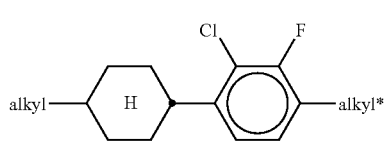
CY4
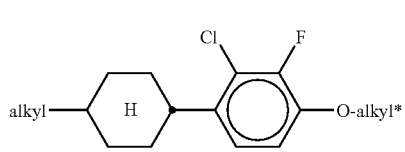
CY5
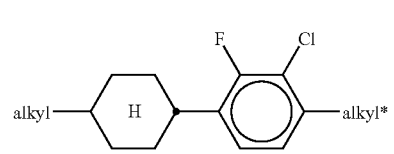
CY6
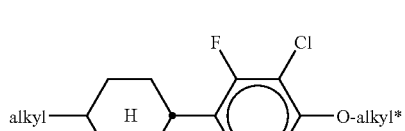
CY7
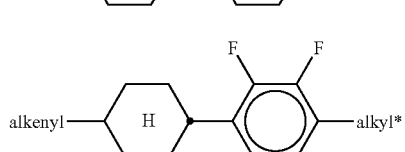
CY8
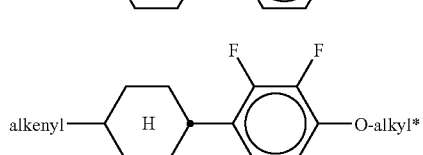
CY9
CY10
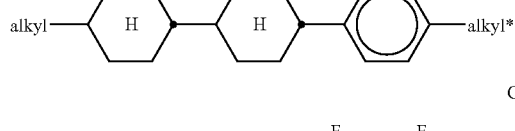
-continued
CY11
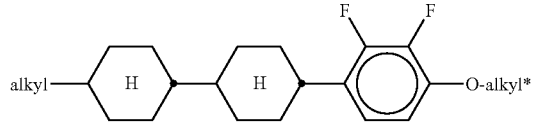
CY11
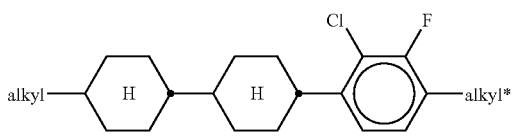
CY12
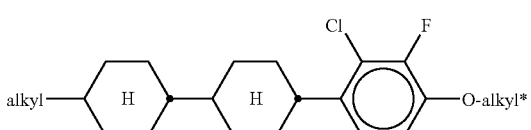
CY13
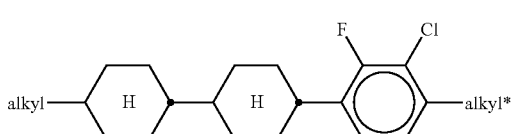
CY14
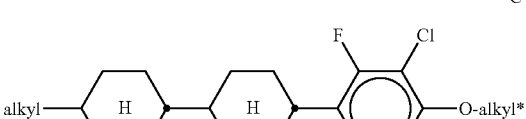
CY15
CY16
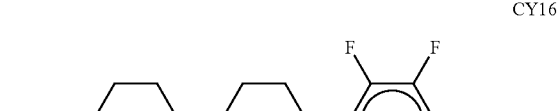
CY17
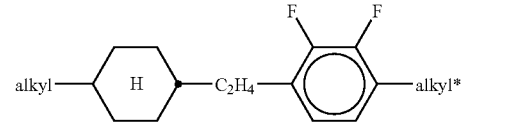
CY18
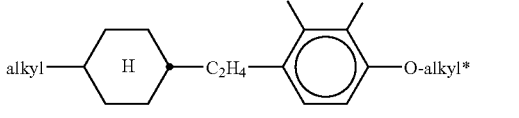
CY19
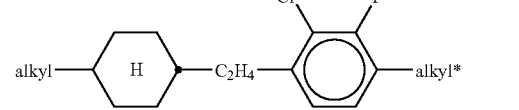
CY20
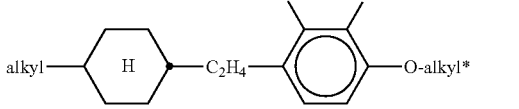

-continued

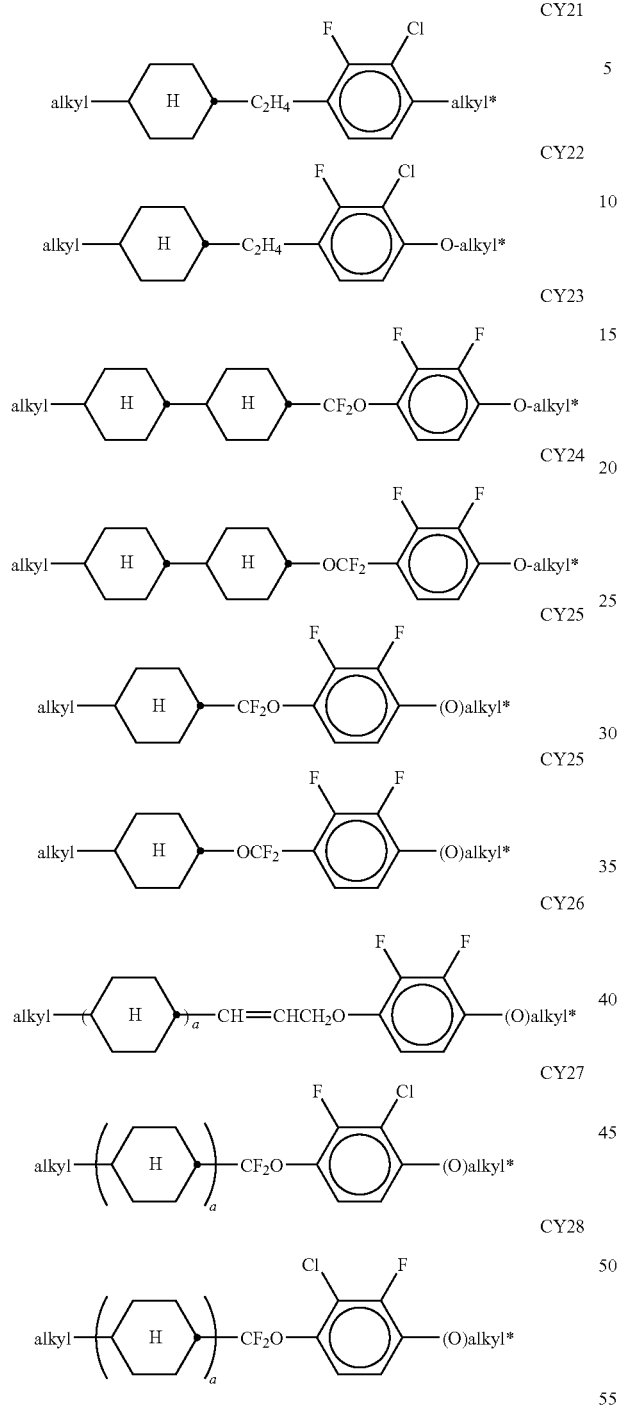

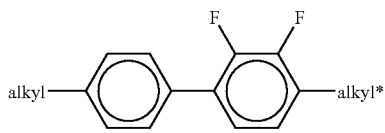
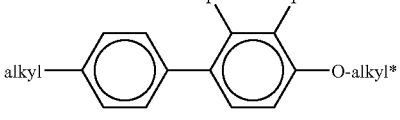
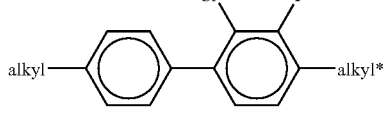
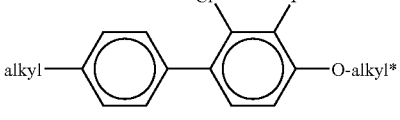
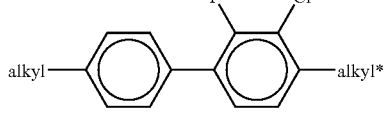
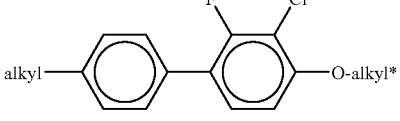
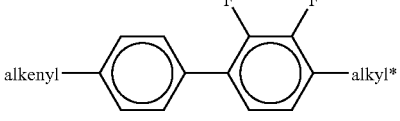
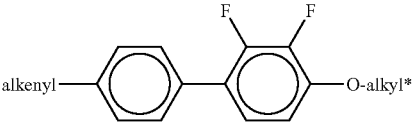
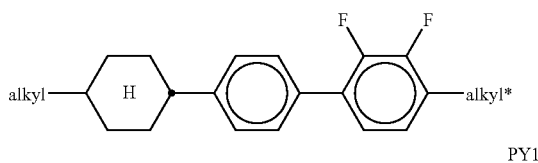
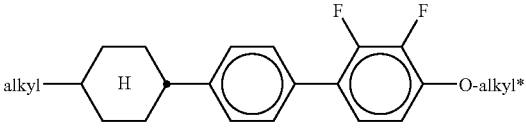
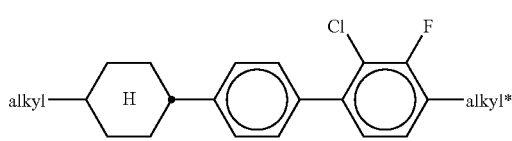

in which a denotes 1 or 2, alkyl and alkyl* each, independently of one another, denote a straight-chain alkyl radical having 1-6 C atoms, and alkenyl denotes a straight-chain alkenyl radical having 2-6 C atoms. Alkenyl preferably denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

The compounds of the formula PY are preferably selected from the following sub-formulae:

-continued

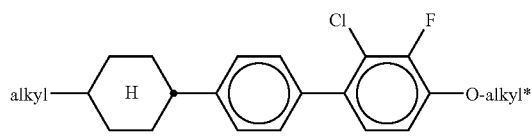
PY12

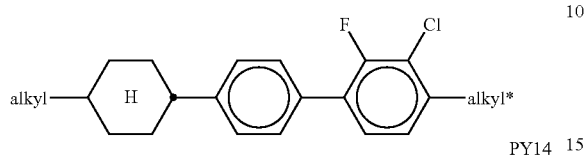
PY13

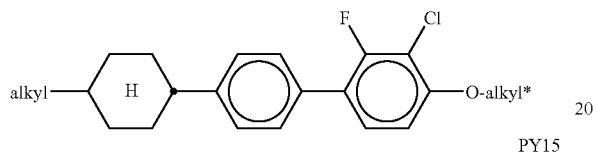
PY14

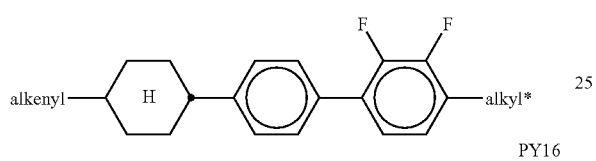
PY15

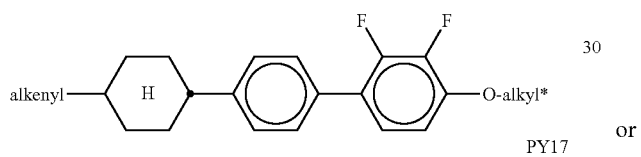
PY16

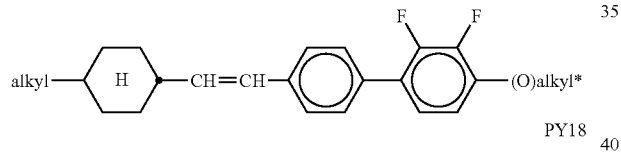
PY17

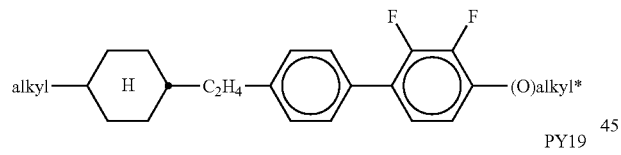
PY18

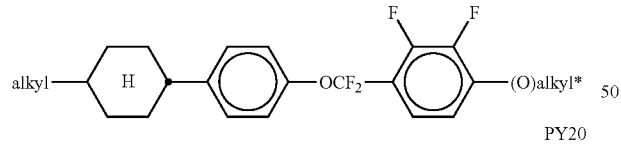
PY19

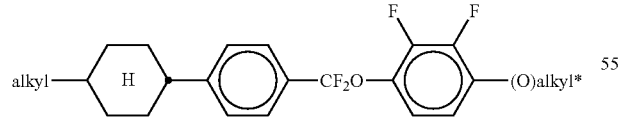
PY20 in which alkyl and alkyl* each, independently of one another, denote a straight-chain alkyl radical having 1-6 C atoms, alkenyl denotes a straight-chain alkenyl radical having 2-6 C atoms, and (O) denotes a single bond or —O—. Alkenyl preferably denotes $CH_2$=CH—, $CH_2$=CHCH$_2$CH$_2$—, $CH_3$—CH=CH—, $CH_3$—CH$_2$—CH=CH—, $CH_3$—$(CH_2)_2$—CH=CH—, $CH_3$—$(CH_2)_3$—CH=CH— or $CH_3$—CH=CH—$(CH_2)_2$—.

b) LC medium which additionally comprises one or more compounds of the following formula:

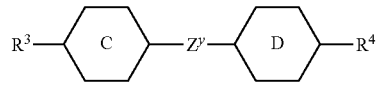
ZK in which the individual radicals have the following meanings:

denotes

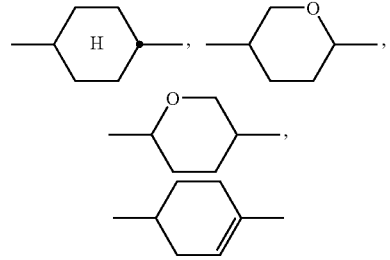

or

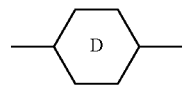
D denotes

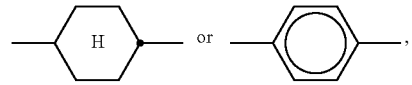

$R^3$ and $R^4$ each, independently of one another, denote alkyl having 1 to 12 C atoms, in which, in addition, one or two non-adjacent $CH_2$ groups may be replaced by —O—, —CH=CH—, —CO—, —OCO— or —COO— in such a way that O atoms are not linked directly to one another, $Z^y$ denotes —$CH_2CH_2$—, —CH=CH—, —$CF_2O$—, —$OCF_2$—, —$CH_2$—, —$OCH_2$—, —COO—, —OCO—, —$C_2F_4$—, —CF=CF—, —CHCH$_2$O—, or a single bond, preferably a single bond.

The compounds of the formula ZK are preferably selected from the following sub-formulae:

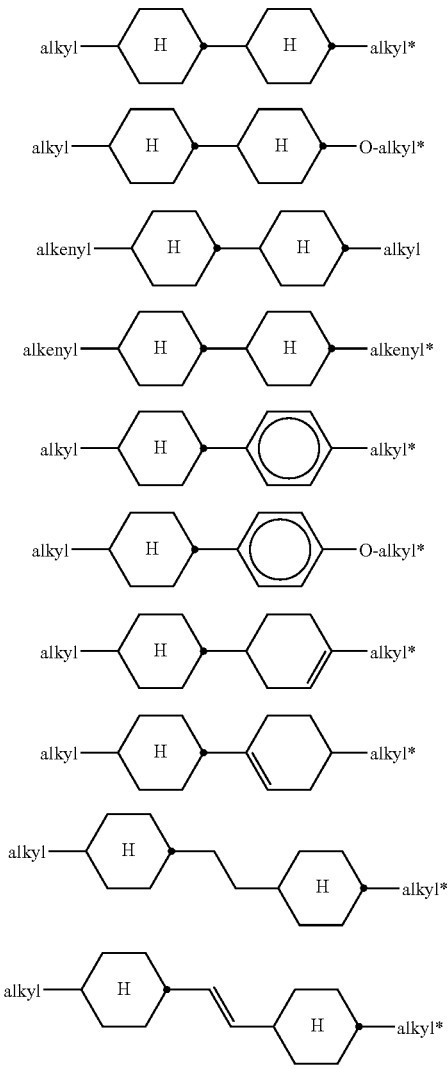

in which alkyl and alkyl* each, independently of one another, denote a straight-chain alkyl radical having 1-6 C atoms, and alkenyl denotes a straight-chain alkenyl radical having 2-6 C atoms. Alkenyl preferably denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

c) LC medium which additionally comprises one or more compounds of the following formula:

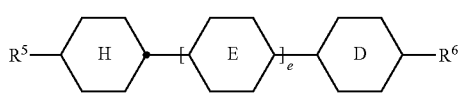

in which the individual radicals on each occurrence, identically or differently, have the following meanings:

R$^5$ and R$^6$ each, independently of one another, have one of the meanings indicated for R$^1$ above,

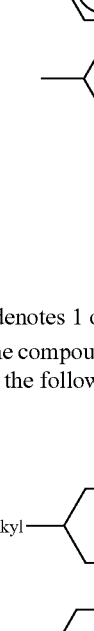

e denotes 1 or 2.

The compounds of the formula DK are preferably selected from the following sub-formulae:

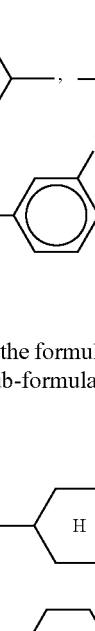

-continued

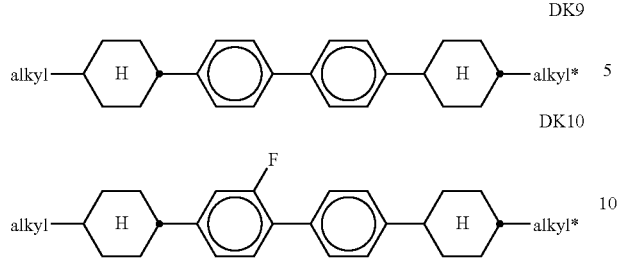

in which alkyl and alkyl* each, independently of one another, denote a straight-chain alkyl radical having 1-6 C atoms, and alkenyl and alkenyl* each, independently of one another, denote a straight-chain alkenyl radical having 2-6 C atoms. Alkenyl and alkenyl* preferably denote $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

d) LC medium which additionally comprises one or more compounds of the following formula:

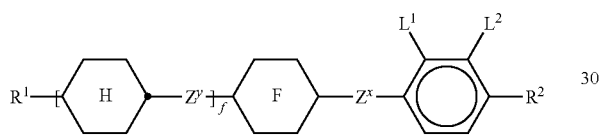

in which the individual radicals have the following meanings:

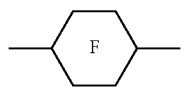

denotes

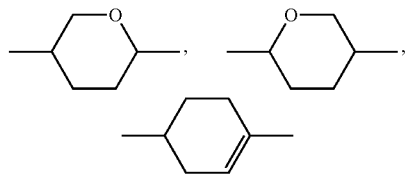

or

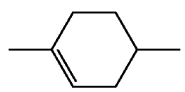

f denotes 0 or 1, $R^1$ and $R^2$ each, independently of one another, denote alkyl having 1 to 12 C atoms, in which, in addition, one or two non-adjacent $CH_2$ groups may be replaced by $-O-$, $-CH=CH-$, $-CO-$, $-OCO-$ or $-COO-$ in such a way that O atoms are not linked directly to one another, $Z^x$ and $Z^y$ each, independently of one another, denote $-CH_2CH_2-$, $-CH=CH-$, $-CF_2O-$, $-OCF_2-$, $-CH_2O-$, $-OCH_2-$, $-COO-$, $-OCO-$, $-C_2F_4-$, $-CF=CF-$, $-CH=CHCH_2O-$, or a single bond, preferably a single bond, $L^1$ and $L^2$ each, independently of one another, denote F, Cl, $OCF_3$, $CF_3$, $CH_3$, $CH_2F$, $CHF_2$.

Preferably, both radicals $L^1$ and $L^2$ denote F or one of the radicals $L^1$ and $L^2$ denotes F and the other denotes Cl.

The compounds of the formula LY are preferably selected from the following sub-formulae:

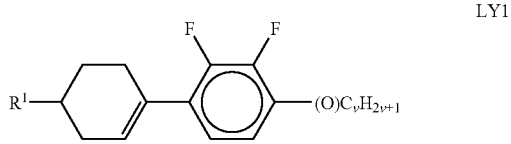

LY1

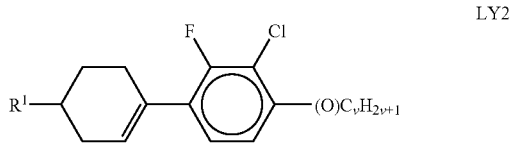

LY2

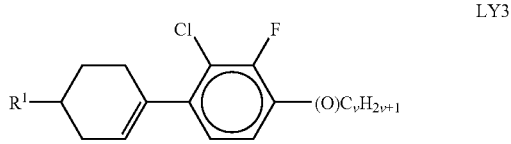

LY3

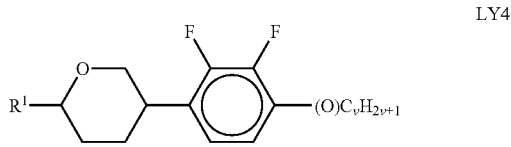

LY4

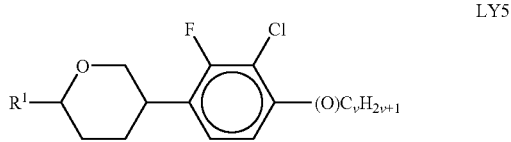

LY5

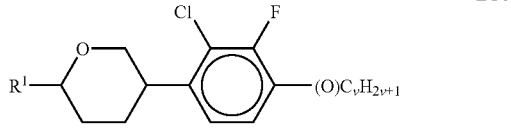

LY6

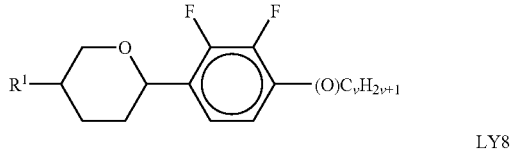

LY7

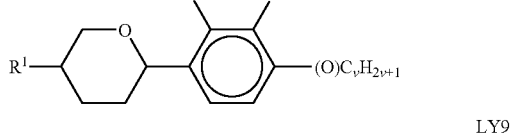

LY8

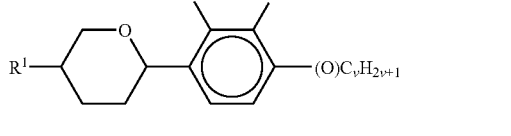

LY9

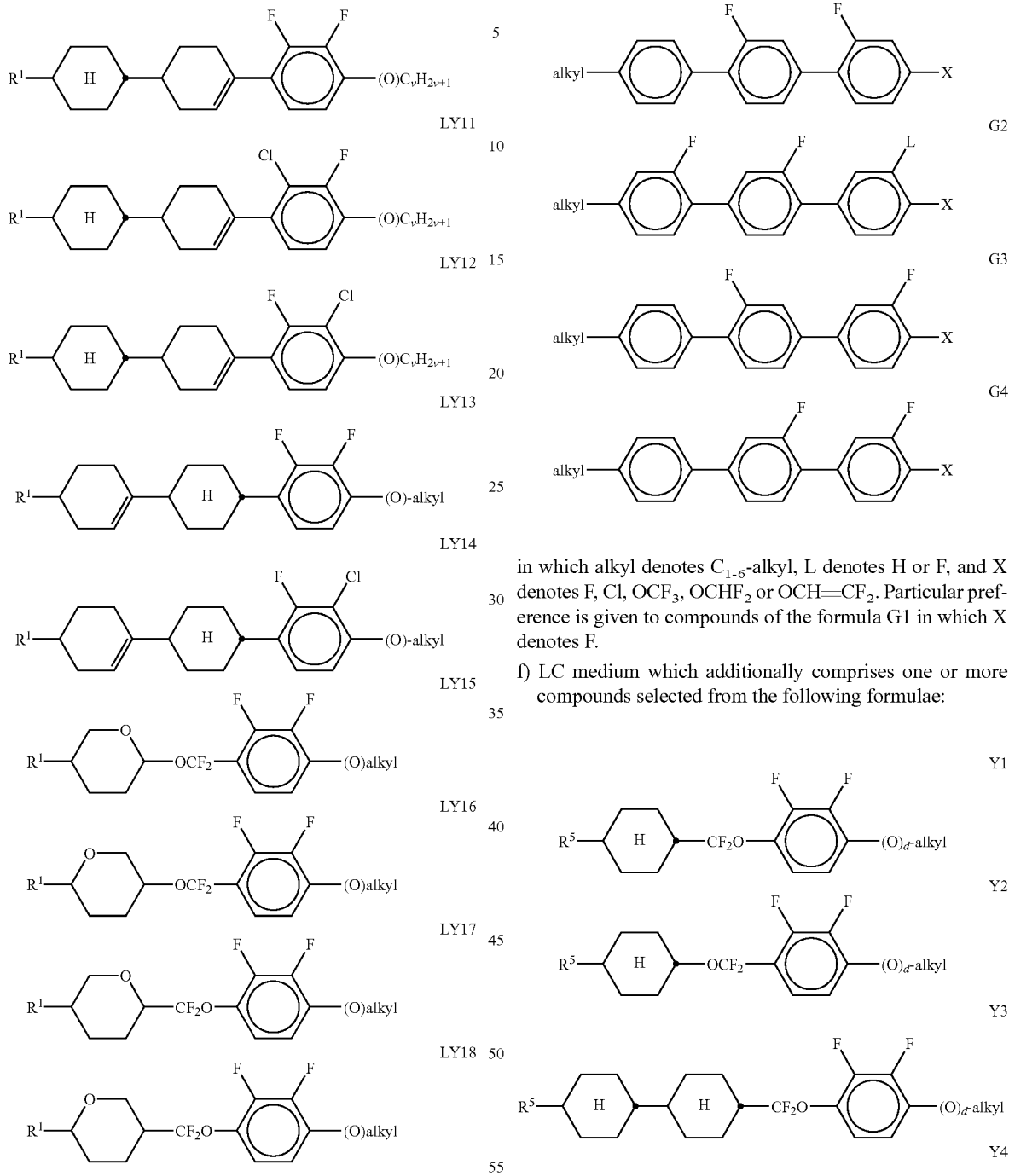

in which alkyl denotes $C_{1-6}$-alkyl, L denotes H or F, and X denotes F, Cl, $OCF_3$, $OCHF_2$ or $OCH{=}CF_2$. Particular preference is given to compounds of the formula G1 in which X denotes F.

f) LC medium which additionally comprises one or more compounds selected from the following formulae:

in which $R^1$ has the meaning indicated above, v denotes an integer from 1 to 6, alkyl denotes a straight chain alkyl radical having 1-6 C atoms, and (O) denotes a single bond or —O—. $R^1$ preferably denotes straight-chain alkyl or alkenyl, in particular $CH_3$, $C_2H_5$, n-$C_3H_7$, n-$C_4H_9$, n-$C_5H_{11}$, $CH_2{=}CH{—}$, $CH_2{=}CHCH2CH_2{—}$, $CH_3{—}CH{=}CH{—}$, $CH_3{—}CH_2{—}CH{=}CH{—}$, $CH_3{—}(CH_2)_2{—}CH{=}CH{—}$, $CH_3{—}(CH_2)_3{—}CH{=}CH{—}$ or $CH_3{—}CH{=}CH{—}(CH_2)_2{—}$.

e) LC medium which additionally comprises one or more compounds selected from the following formulae:

-continued

Y6
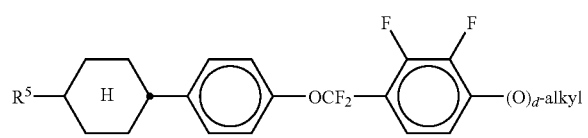

Y7
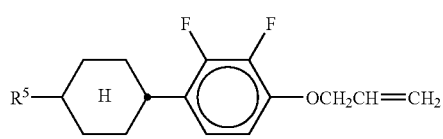

Y8
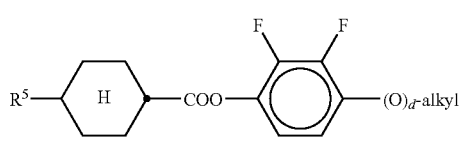

Y9
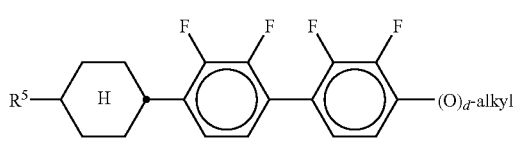

Y10
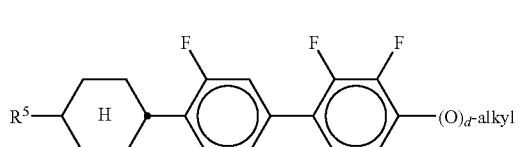

Y11
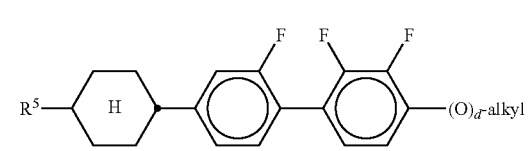

Y12
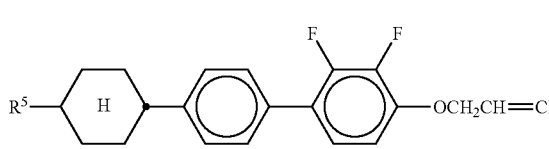

Y13
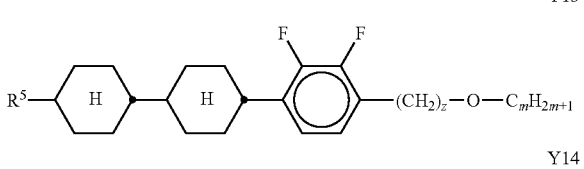

Y14
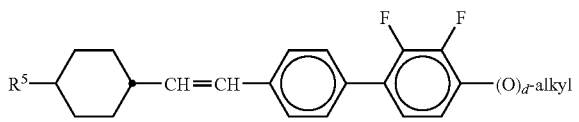

Y15
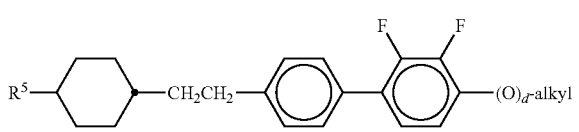

Y16
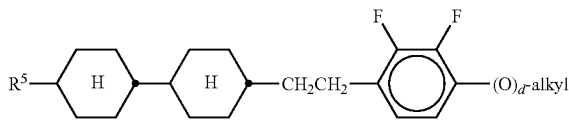

in which $R^5$ has one of the meanings indicated for $R^1$ above, alkyl denotes $C_{1-6}$-alkyl, d denotes 0 or 1, and z and m each, independently of one another, denote an integer from 1 to 6. $R^5$ in these compounds is particularly preferably $C_{1-6}$-alkyl or -alkoxy or $C_{2-6}$-alkenyl, d is preferably 1. The LC medium according to the invention preferably comprises one or more compounds of the above-mentioned formulae in amounts of $\geq 5\%$ by weight.

g) LC medium which additionally comprises one or more biphenyl compounds of the following formulae:

B1
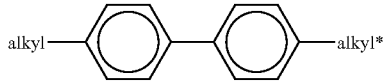

B2
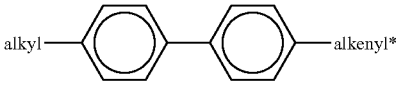

B3
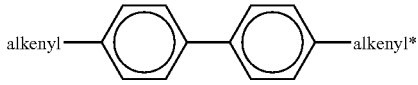

in which alkyl and alkyl* each, independently of one another, denote a straight-chain alkyl radical having 1-6 C atoms, and alkenyl and alkenyl* each, independently of one another, denote a straight-chain alkenyl radical having 2-6 C atoms. Alkenyl and alkenyl* preferably denote $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

The proportion of the biphenyls of the formulae B1 to B3 in the LC mixture is preferably at least 3% by weight, in particular $\geq 5\%$ by weight.

The compounds of the formula B2 are particularly preferred.

The compounds of the formulae B1 to B3 are preferably selected from the following sub-formulae:

B1a
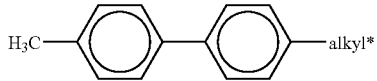

B2a
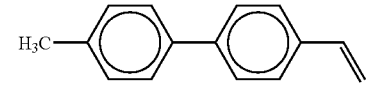

B2b
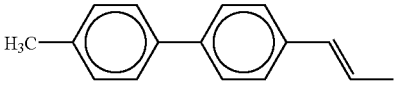

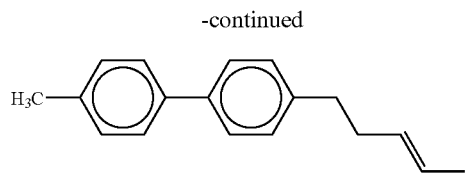
B2c in which alkyl* denotes an alkyl radical having 1-6 C atoms. The medium according to the invention particularly preferably comprises one or more compounds of the formulae B1a and/or B2c.

h) LC medium which additionally comprises one or more terphenyl compounds of the following formula:

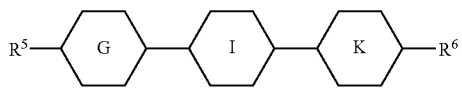
T in which $R^5$ and $R^6$ each, independently of one another, have one of the meanings indicated for $R^1$ above, and

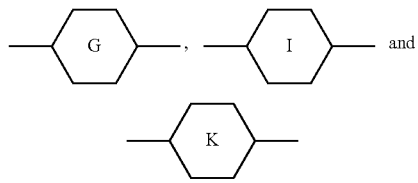

each, independently of one another, denote

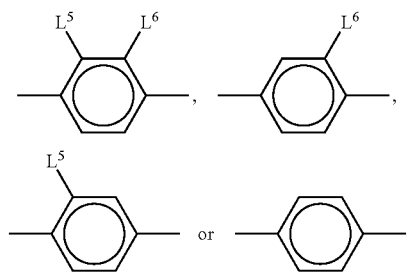

in which $L^5$ denotes F or Cl, preferably F, and $L^6$ denotes F, Cl, OCF$_3$, CF$_3$, CH$_3$ CH$_2$F or CHF$_2$, preferably F.

The compounds of the formula T are preferably selected from the following sub-formulae:

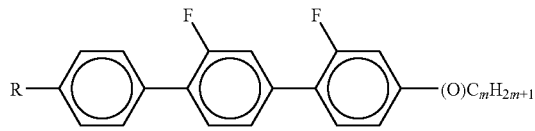
T1

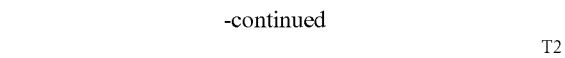
T2

T3

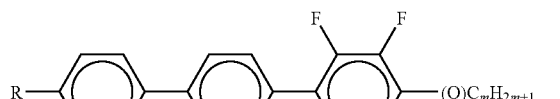
T4

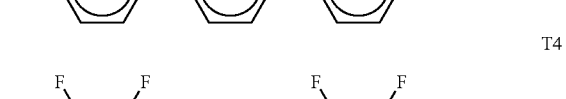
T5

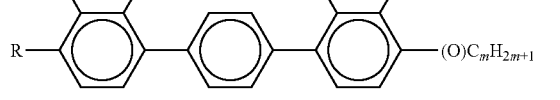
T6

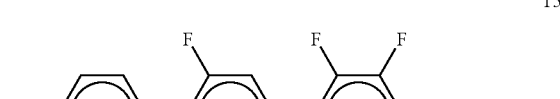
T7

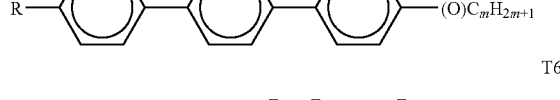
T8

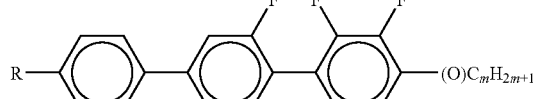
T9

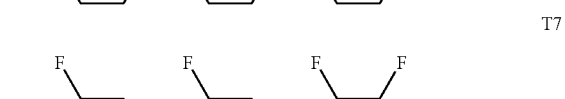
T10

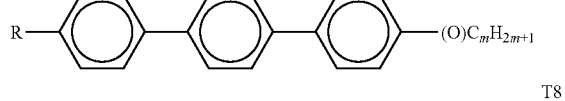
T11

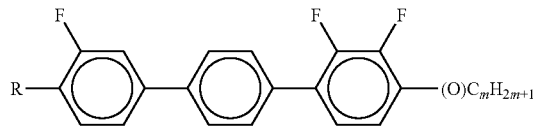

in which R denotes a straight-chain alkyl or alkoxy radical having 1-7 C atoms, R* denotes a straight-chain alkenyl radical having 2-7 C atoms, m denotes an integer from 1 to 6, and (O) denotes a single bond or —O—. R* preferably denotes CH$_2$=CH—, CH$_2$=CHCH$_2$CH$_2$—, CH$_3$—CH=CH—, CH$_3$—CH$_2$—CH=CH—, CH$_3$—(CH$_2$)$_2$—CH=CH—, CH$_3$—(CH$_2$)$_3$—CH=CH— or CH$_3$—CH=CH—(CH$_2$)$_2$—.

R preferably denotes methyl, ethyl, propyl, butyl, pentyl, hexyl, methoxy, ethoxy, propoxy, butoxy or pentoxy.

The LC medium according to the invention preferably comprises the terphenyls of the formula T and preferred sub-formulae thereof in an amount of 2-30% by weight, in particular 5-20% by weight.

Particular preference is given to compounds of the formulae T1, T2, T3 and T21. In these compounds, R preferably denotes alkyl, furthermore alkoxy, each having 1-5 C atoms.

The terphenyls are preferably employed in mixtures according to the invention if the Δn value of the mixture is intended to be ≧0.1. Preferred mixtures comprise 2-20% by weight of one or more terphenyl compounds of the formula T, preferably selected from the group of compounds T1 to T22.

i) LC medium which additionally comprises one or more compounds of the following formulae:

-continued

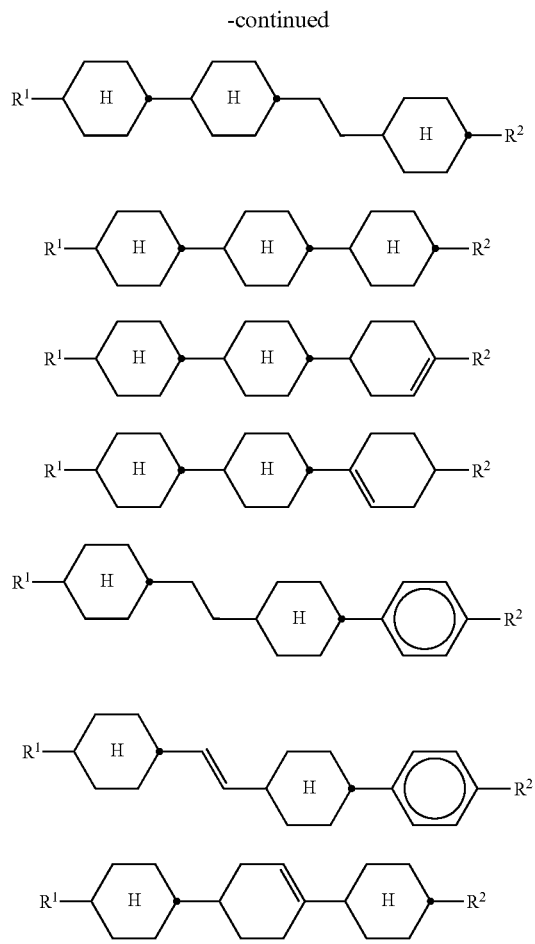

in which R¹ and R² have the meanings indicated above and preferably each, independently of one another, denote straight-chain alkyl or alkenyl having up to 12 C atoms.

Preferred media comprise one or more compounds selected from the formulae O1, O3 and O4.

k) LC medium which additionally comprises one or more compounds of the following formula:

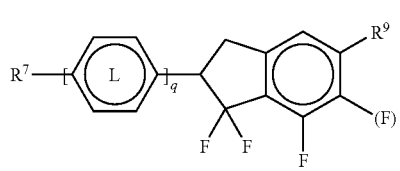

FI in which

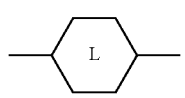

denotes

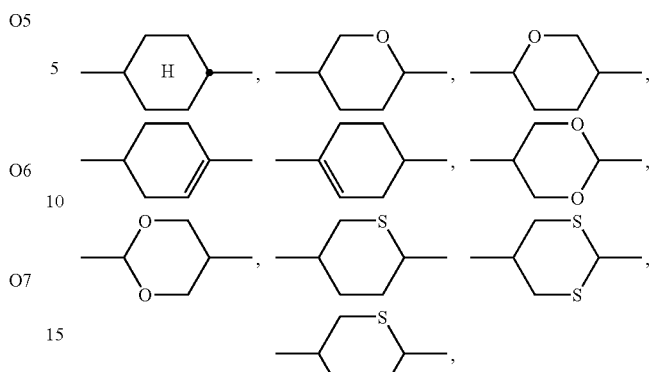

$R^9$ denotes H, $CH_3$, $C_2H_5$ or n-$C_3H_7$, and q denotes 1, 2 or 3, (F) denotes an optional F substituent (the position may or may not be substituted by F), and $R^7$ has one of the meanings indicated for $R^1$, preferably in amounts of >3% by weight, in particular ≧5% by weight and very particularly preferably 5-30% by weight.

Particularly preferred compounds of the formula IF are selected from the following sub-formulae:

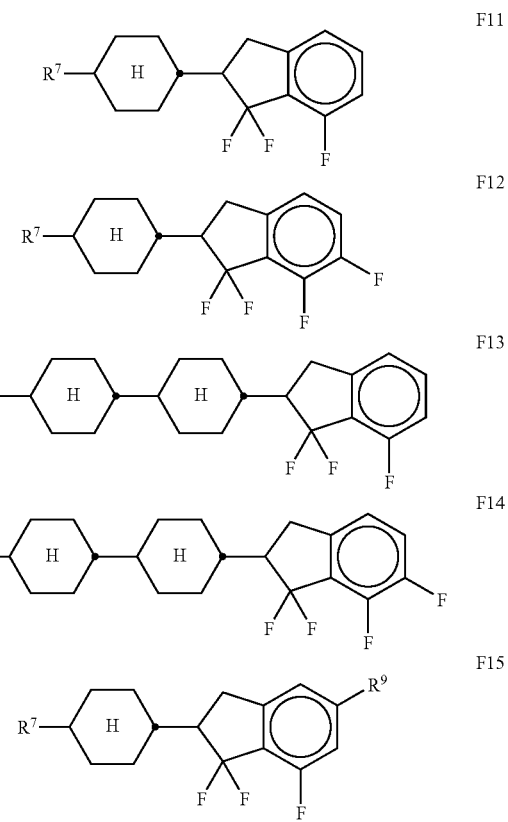

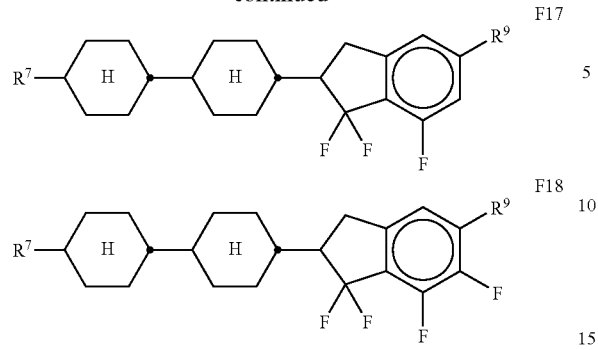

F17

F18 in which R⁷ preferably denotes straight-chain alkyl, and R⁹ denotes $CH_3$, $C_2H_5$ or n-$C_3H_7$. Particular preference is given to the compounds of the formulae FI1, FI2 and FI3.

m) LC medium which additionally comprises one or more compounds of the following formulae:

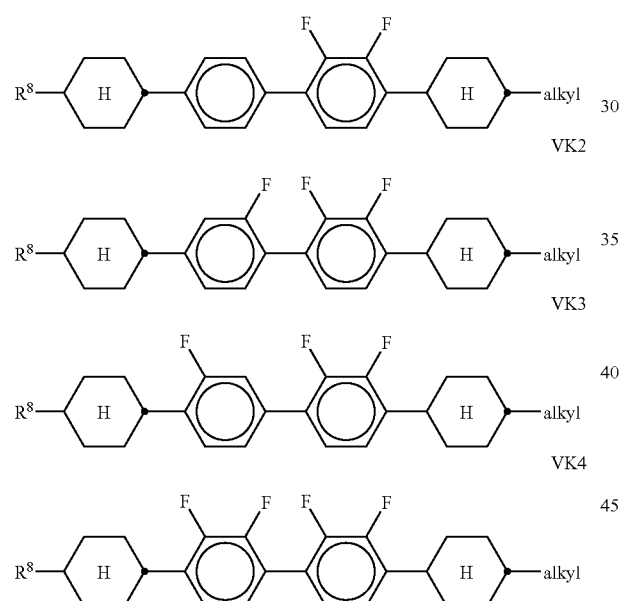

VK1

VK2

VK3

VK4 in which R⁸ has the meaning indicated for R¹, and alkyl denotes a straight-chain alkyl radical having 1-6 C atoms.

n) LC medium which additionally comprises one or more compounds which have a tetrahydronaphthyl or naphthyl unit, such as, for example, the compounds selected from the following formulae:

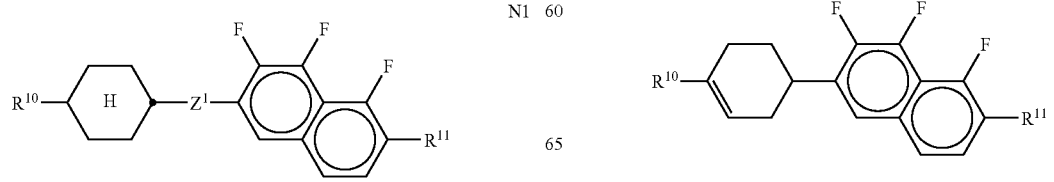

N1

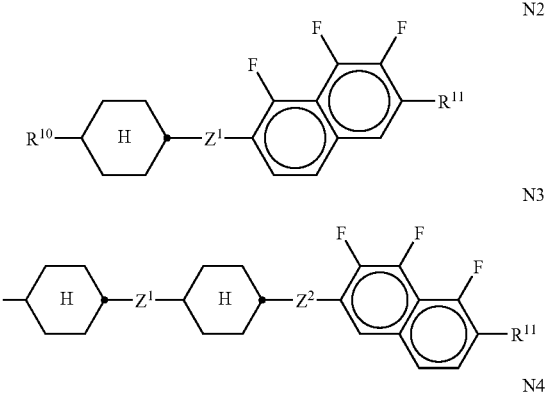

N2

N3

N4

N5

N6

N7

N8

N9

N10 in which $R^{10}$ and $R^{11}$ each, independently of one another, have one of the meanings indicated for $R^1$, preferably denote straight-chain alkyl, straight-chain alkoxy or straight-chain alkenyl, and $Z^1$ and $Z^2$ each, independently of one another, denote —$C_2H_4$—, —CH=CH—, —$(CH_2)_4$—, —$(CH_2)_3$O—, —$O(CH_2)_3$—, —CH=CHCH$_2$CH$_2$—, —CH$_2$CH$_2$CH=CH—, —CH$_2$O—, —OCH$_2$—, —COO—, —OCO—, —$C_2F_4$—, —CF=CF—, —CF=CH—, —CH=CF—, —CH$_2$— or a single bond.

o) LC medium which additionally comprises one or more difluoro-dibenzochromans and/or chromans of the following formulae:

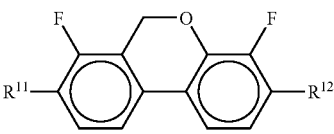
BC

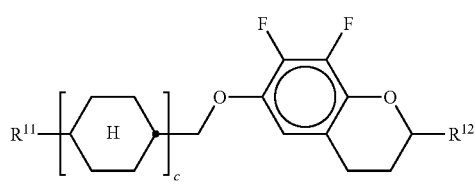
CR in which $R^{11}$ and $R^{12}$ each, independently of one another, have the meaning indicated above, and c denotes 0 or 1, preferably in amounts of 3 to 20% by weight, in particular in amounts of 3 to 15% by weight.

Particularly preferred compounds of the formulae BC and CR are selected from the following sub-formulae:

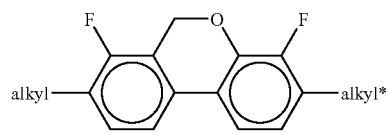
BC1

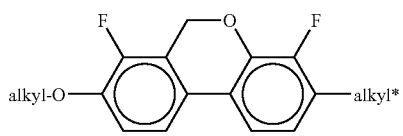
BC2

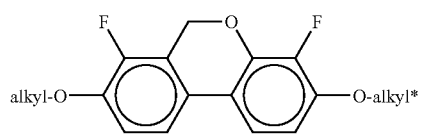
BC3

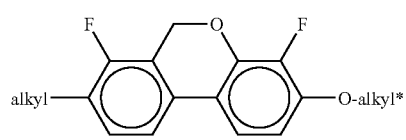
BC4

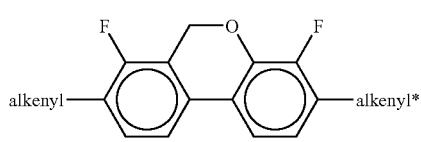
BC5

-continued

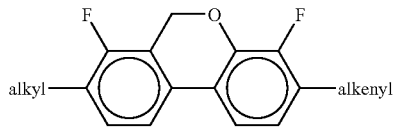
BC6

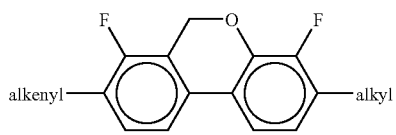
BC7

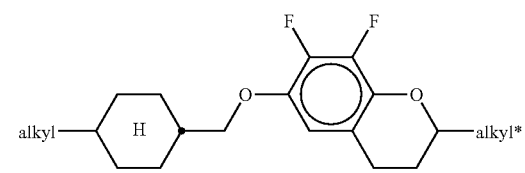
CR1

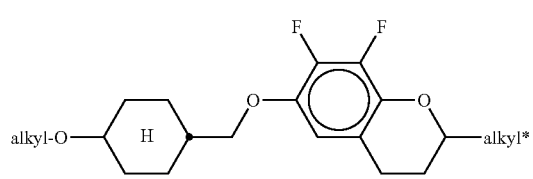
CR2

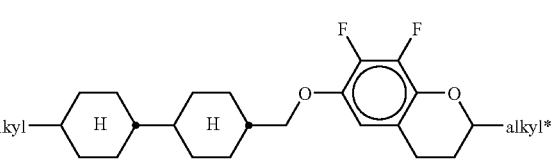
CR3

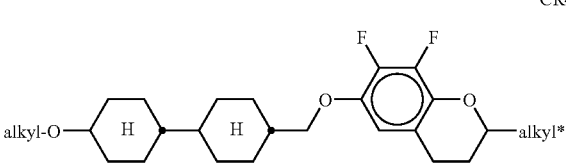
CR4

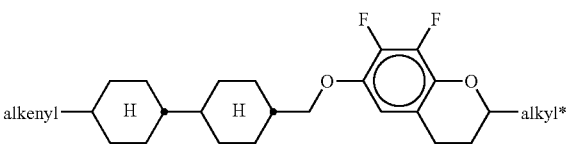
CR5

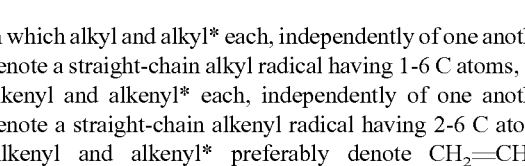

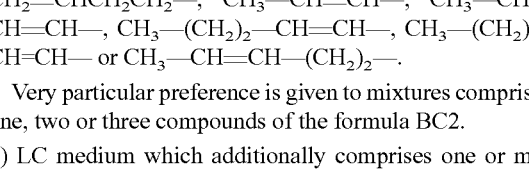

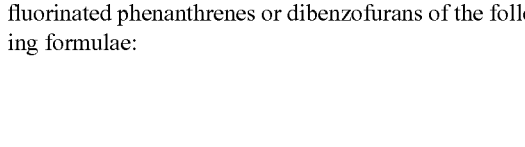

in which alkyl and alkyl* each, independently of one another, denote a straight-chain alkyl radical having 1-6 C atoms, and alkenyl and alkenyl* each, independently of one another, denote a straight-chain alkenyl radical having 2-6 C atoms. Alkenyl and alkenyl* preferably denote CH$_2$=CH—, CH$_2$=CHCH$_2$CH$_2$—, CH$_3$—CH=CH—, CH$_3$—CH$_2$—CH=CH—, CH$_3$—(CH$_2$)$_2$—CH=CH—, CH$_3$—(CH$_2$)$_3$—CH=CH— or CH$_3$—CH=CH—(CH$_2$)$_2$—.

Very particular preference is given to mixtures comprising one, two or three compounds of the formula BC2.

p) LC medium which additionally comprises one or more fluorinated phenanthrenes or dibenzofurans of the following formulae:

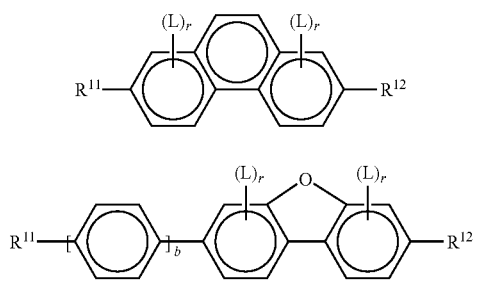

PH

BF in which R[11] and R[12] each, independently of one another, have the meanings indicated above, b denotes 0 or 1, L denotes F, and r denotes 1, 2 or 3.

Particularly preferred compounds of the formulae PH and BF are selected from the following sub-formulae:

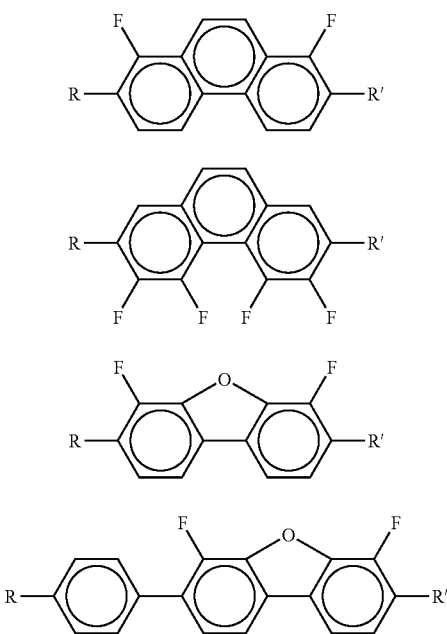

PH1

PH2

BF1

BF2 in which R and R' each, independently of one another, denote a straight-chain alkyl or alkoxy radical having 1-7 C atoms.

q) LC medium, preferably for use in PSA-OCB displays, which comprises one or more compounds of the following formulae:

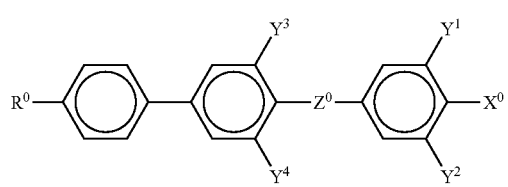

AA

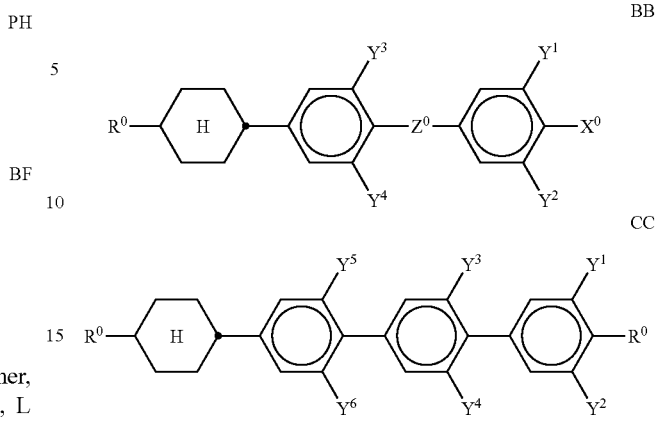

BB

CC in which

R$^0$ on each occurrence, identically or differently, denotes n-alkyl, alkoxy, oxaalkyl, fluoroalkyl or alkenyl, each having up to 9 C atoms, X$^0$ denotes F, Cl or in each case halogenated alkyl, alkenyl, alkenyloxy or alkoxy, each having up to 6 C atoms, Z$^0$ denotes —CF$_2$O— or a single bond, Y$^{1-6}$ each, independently of one another, denote H or F.

X$^0$ is preferably F, Cl, CF$_3$, CHF$_2$, OCF$_3$, OCHF$_2$, OCF-HCF$_3$, OCFHCHF$_2$, OCFHCHF$_2$, OCF$_2$CH$_3$, OCF$_2$CHF$_2$, OCF$_2$CHF$_2$, OCF$_2$CF$_2$CHF$_2$, OCF$_2$CF$_2$CHF$_2$, OCFHCF$_2$CF$_3$, OCFHCF$_2$CHF$_2$, OCF$_2$CF$_2$CF$_3$, OCF$_2$CF$_2$CClF$_2$, OCClFCF$_2$CF$_3$ or CH=CF$_2$, particularly preferably F or OCF$_3$.

The compounds of the formula AA are preferably selected from the following formulae:

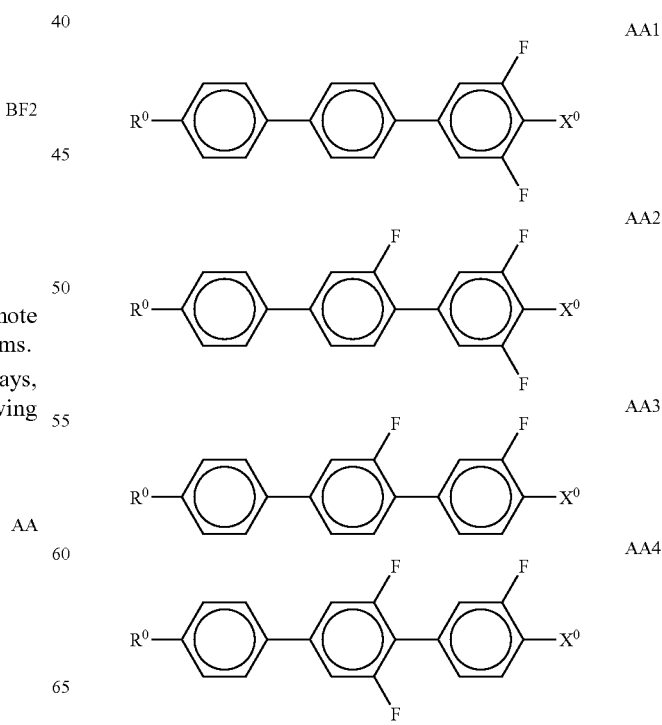

AA1

AA2

AA3

AA4

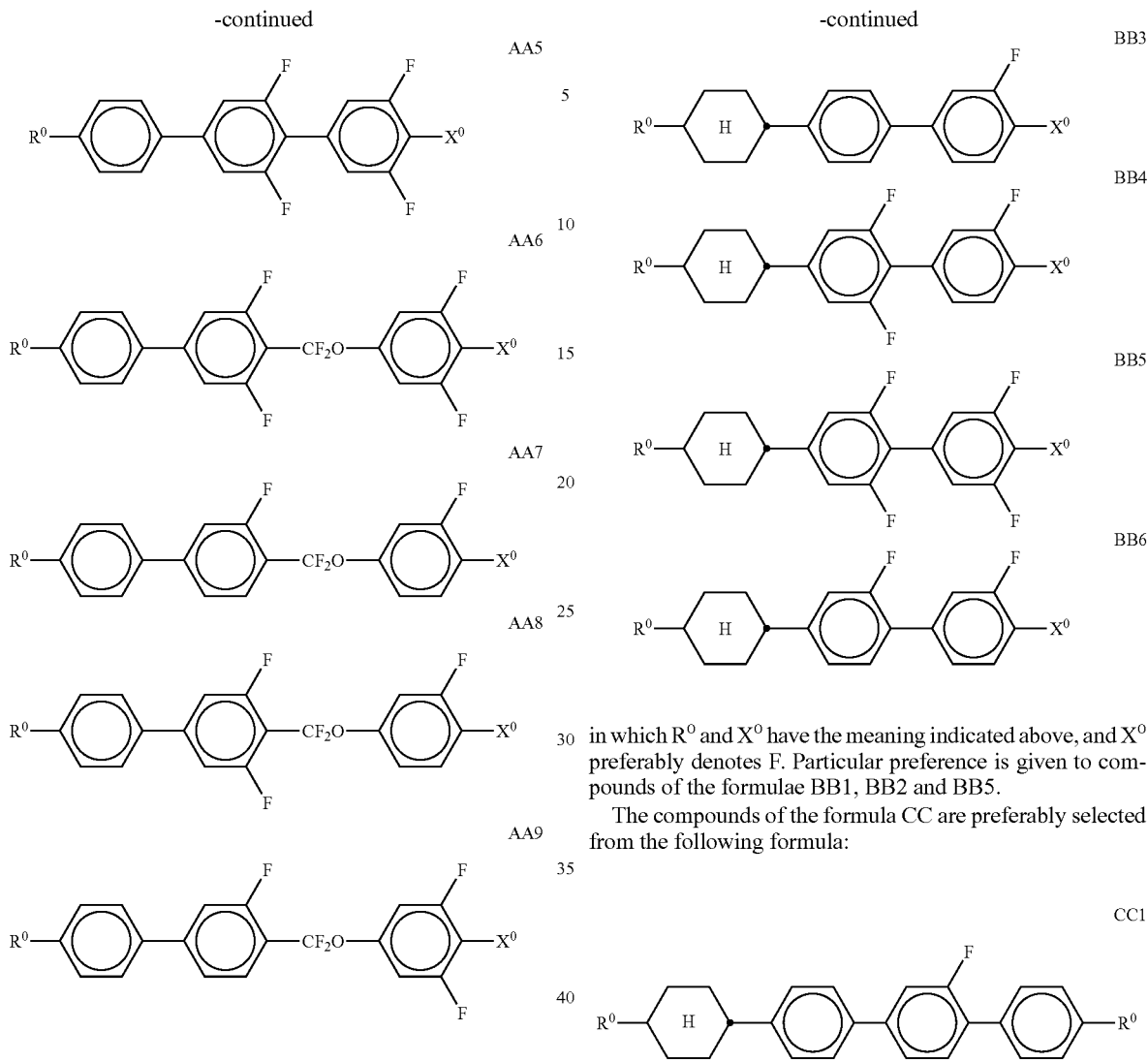

in which R⁰ and X⁰ have the meaning indicated above, and X⁰ preferably denotes F. Particular preference is given to compounds of the formulae AA2 and AA6.

The compounds of the formula BB are preferably selected from the following formulae:

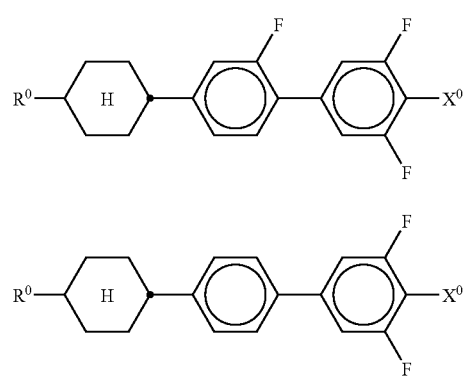

in which R⁰ and X⁰ have the meaning indicated above, and X⁰ preferably denotes F. Particular preference is given to compounds of the formulae BB1, BB2 and BB5.

The compounds of the formula CC are preferably selected from the following formula:

in which R⁰ on each occurrence, identically or differently, has the meaning indicated above and preferably denotes alkyl having 1 to 6 C atoms.

r) LC medium which, apart from the polymerizable compounds of the formula I or sub-formulae thereof and the comonomers, comprises no compounds which have a terminal vinyloxy group (—O—CH—CH₂).

s) LC medium which comprises 1 to 5, preferably 1, 2 or 3, polymerizable compounds.

t) LC medium in which the proportion of polymerizable compounds in the mixture as a whole is 0.05 to 5%, preferably 0.1 to 1%.

u) LC medium which comprises 1 to 8, preferably 1 to 5, compounds of the formulae CY1, CY2, PY1 and/or PY2. The proportion of these compounds in the mixture as a whole is preferably 5 to 60%, particularly preferably 10 to 35%. The content of these individual compounds is preferably in each case 2 to 20%.

v) LC medium which comprises 1 to 8, preferably 1 to 5, compounds of the formulae CY9, CY10, PY9 and/or PY10. The proportion of these compounds in the mixture as a whole is preferably 5 to 60%, particularly preferably 10 to 35%. The content of these individual compounds is preferably in each case 2 to 20%.

w) LC medium which comprises 1 to 10, preferably 1 to 8, compounds of the formula ZK, in particular compounds of the formulae ZK1, ZK2 and/or ZK1. The proportion of these compounds in the mixture as a whole is preferably 3 to 25%, particularly preferably 5 to 45%. The content of these individual compounds is preferably in each case 2 to 20%.

x) LC medium in which the proportion of compounds of the formulae CY, PY and ZK in the mixture as a whole is greater than 70%, preferably greater than 80%.

y) LC medium which additionally comprises one or more, preferably low-molecular-weight and/or unpolymerizable, chiral dopants, particularly preferably selected from Table B below and in the concentration ranges indicated therein.

The combination of compounds of the preferred embodiments a)-y) indicated above with the polymerized compounds described above effects low threshold voltages, low rotational viscosities and very good low-temperature stabilities in the LC media according to the invention at the same time as constantly high clearing points and high HR values and allows a pretilt angle to be established in PSA displays. In particular, the LC media in PSA displays exhibit significantly shortened response times, in particular also the grey-shade response times, compared with the media from the prior art.

The liquid-crystal mixture preferably has a nematic phase range of at least 80 K, particularly preferably at least 100 K, and a rotational viscosity of not greater than 250, preferably not greater than 200 mPa·s, at 20° C.

LC media according to the invention for use in displays of the VA type have a negative dielectric anisotropy $\Delta\epsilon$, preferably of about –0.5 to –7.5, in particular about –2.5 to –5.5, at 20° C. and 1 kHz.

LC media according to the invention for use in displays of the OCB type have a positive dielectric anisotropy $\Delta\epsilon$, preferably of about +7 to +17 at 20° C. and 1 kHz.

The birefringence $\Delta n$ in LC media according to the invention for use in displays of the VA type is preferably below 0.16, particularly preferably between 0.06 and 0.14, in particular between 0.07 and 0.12.

The birefringence $\Delta n$ in LC media according to the invention for use in displays of the OCB type is preferably between 0.14 and 0.22, in particular between 0.16 and 0.22.

The dielectrics may also comprise further additives known to the person skilled in the art and described in the literature. For example, 0 to 15% by weight of pleochroic dyes may be added, furthermore nanoparticles, conductive salts, preferably ethyidimethyidodecylammonium 4-hexoxybenzoate, tetrabutylammonium tetraphenylborate or complex salts of crown ethers (cf., for example, Haller et al., Mol. Cryst. Liq. Cryst. 24, 249-258 (1973)), for improving the conductivity, or substances may be added for modifying the dielectric anisotropy, the viscosity and/or the alignment of the nematic phases. Substances of this type are described, for example, in DE-A 22 09 127, 22 40 864, 23 21 632, 23 38 281, 24 50 088, 26 37 430 and 28 53 728.

The individual components of the preferred embodiments a)-y) of the LC media according to the invention are either known or their preparation processes can readily be derived from the prior art by the person skilled in the relevant art, since they are based on standard methods described in the literature. Corresponding compounds of the formula CY are described, for example, in EP-A-0 364 538. Corresponding compounds of the formula ZK are described, for example, in DE-A-26 36 684 and DE-A-33 21 373.

The LC media which can be used in accordance with the invention are prepared in a manner conventional per se, for example by mixing one or more of the above-mentioned compounds with one or more polymerizable compounds as defined above, and optionally with further liquid-crystalline compounds and/or additives. In general, the desired amount of the components used in the smaller amount is dissolved in the components making up the principal constituent, advantageously at elevated temperature. It is also possible to mix solutions of the components in an organic solvent, for example in acetone, chloroform or methanol, and to remove the solvent again, for example by distillation, after thorough mixing. The invention furthermore relates to the process for the preparation of the LC media according to the invention.

It goes without saying to the person skilled in the art that the LC media according to the invention may also comprise compounds in which, for example, H, N, O, Cl, F have been replaced by the corresponding isotopes.

The construction of the LC displays according to the invention corresponds to the usual geometry for PSA displays, as described in the prior art cited at the outset. Geometries without protrusions are preferred, in particular those in which, in addition, the electrode is unstructured on the color filter side, and only the electrode on the TFT side has slots. Particularly suitable and preferred electrode structures for PSA-VA displays are described, for example, in US 2006/0066793 A1.

The following examples explain the present invention without limiting it. However, they show the person skilled in the art preferred mixture concepts with compounds preferably to be employed and the respective concentrations thereof and combinations thereof with one another. In addition, the examples illustrate what properties and property combinations are accessible.

The following abbreviations are used:
(n, m, z: in each case, independently of one another, 1, 2, 3, 4, 5 or 6)

TABLE A

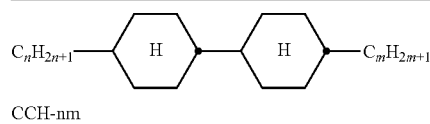

CCH-nm

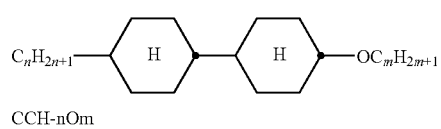

CCH-nOm

TABLE A-continued
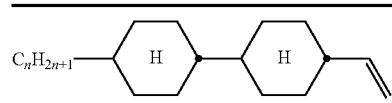
CC-n-V
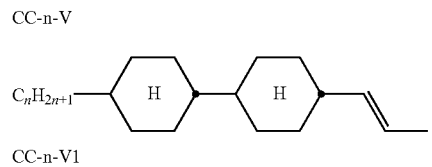
CC-n-V1
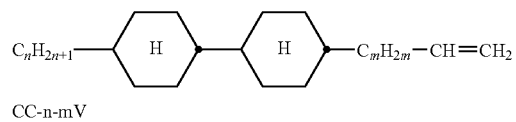
CC-n-mV
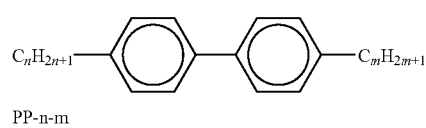
PP-n-m
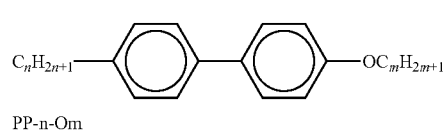
PP-n-Om
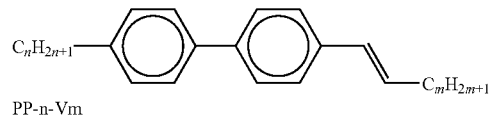
PP-n-Vm
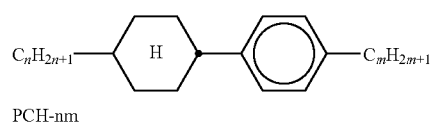
PCH-nm
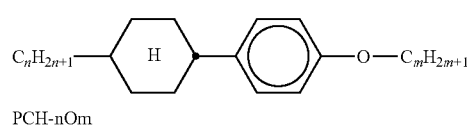
PCH-nOm
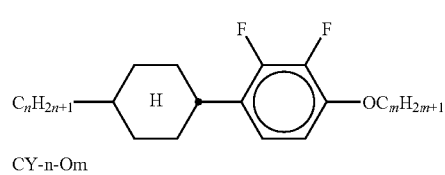
CY-n-Om
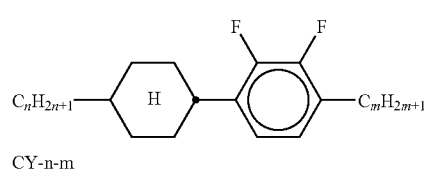
CY-n-m
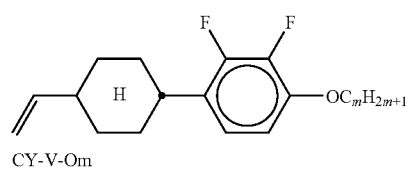
CY-V-Om TABLE A-continued
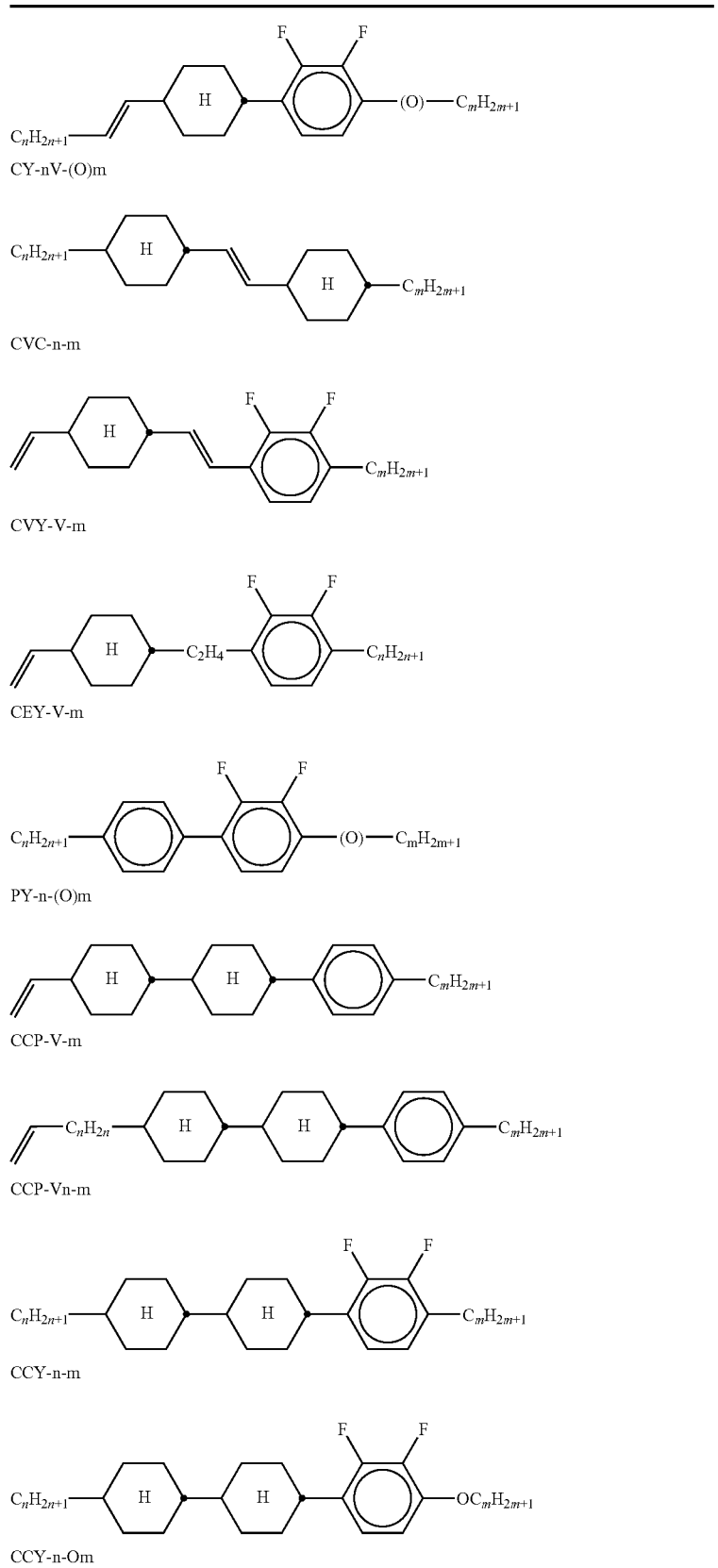
CY-nV-(O)m
CVC-n-m
CVY-V-m
CEY-V-m
PY-n-(O)m
CCP-V-m
CCP-Vn-m
CCY-n-m
CCY-n-Om TABLE A-continued
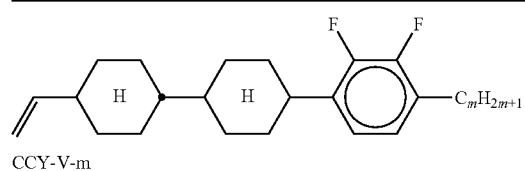
CCY-V-m
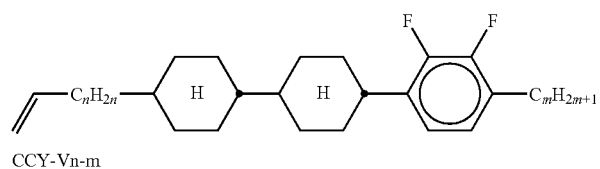
CCY-Vn-m
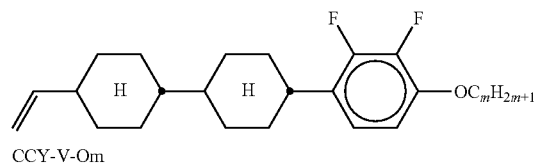
CCY-V-Om
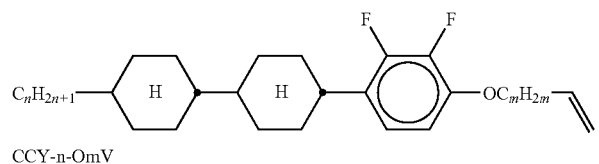
CCY-n-OmV
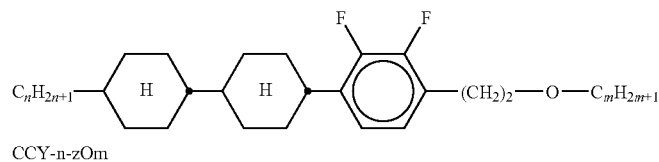
CCY-n-zOm
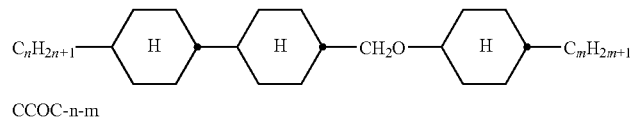
CCOC-n-m
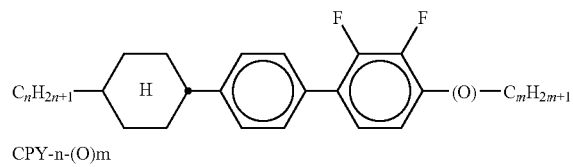
CPY-n-(O)m
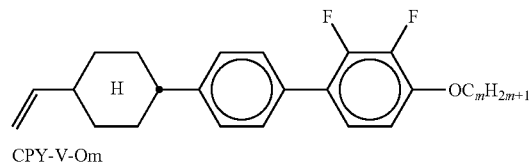
CPY-V-Om
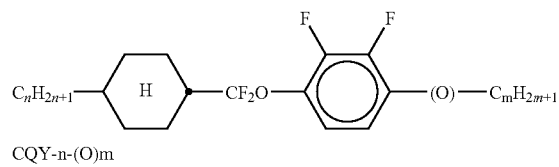
CQY-n-(O)m TABLE A-continued
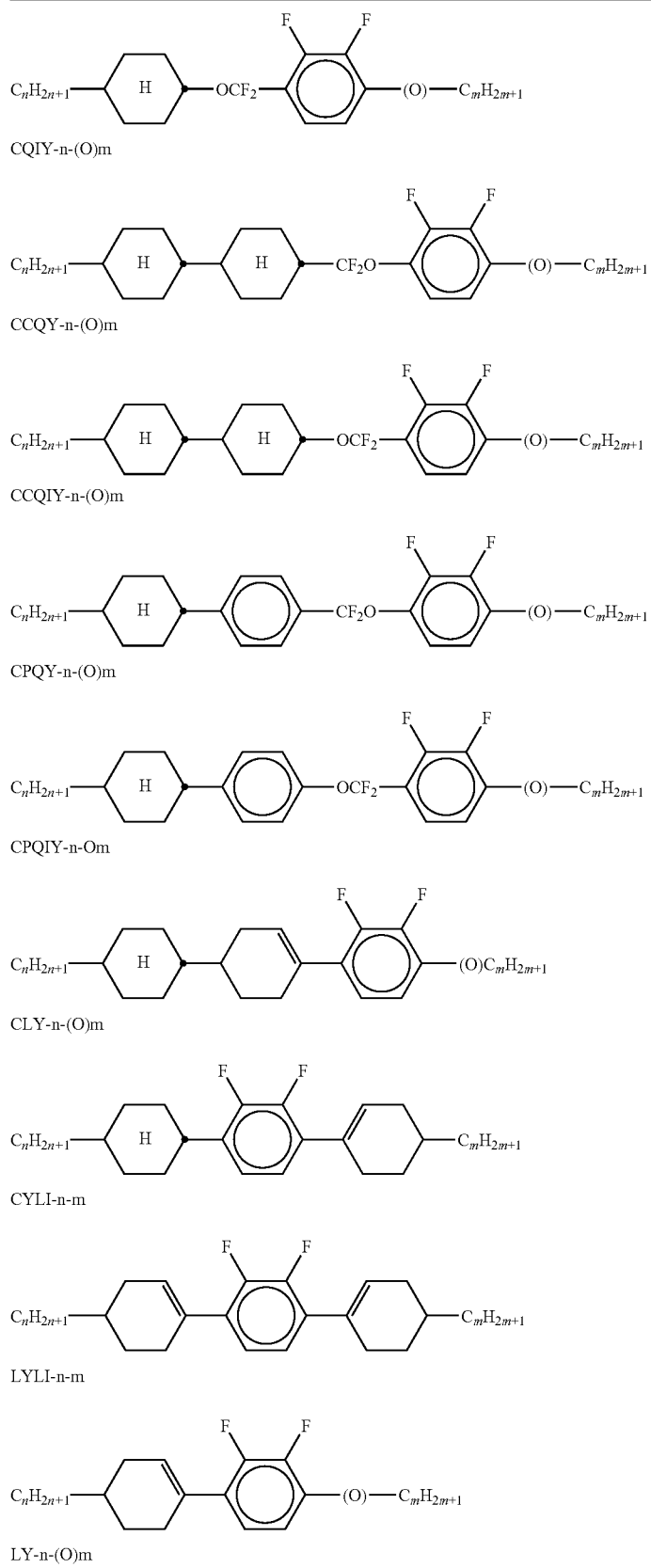
CQIY-n-(O)m
CCQY-n-(O)m
CCQIY-n-(O)m
CPQY-n-(O)m
CPQIY-n-Om
CLY-n-(O)m
CYLI-n-m
LYLI-n-m
LY-n-(O)m TABLE A-continued
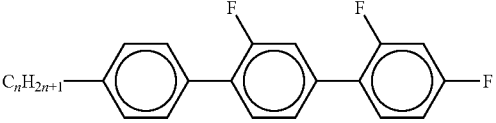
PGIGI-n-F
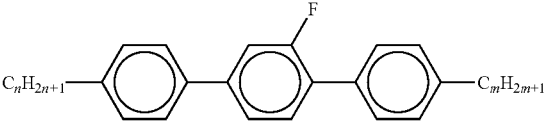
PGP-n-m
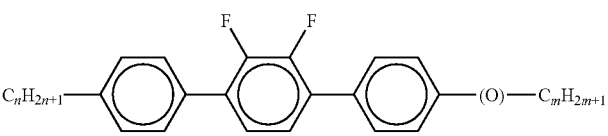
PYP-n-(O)m
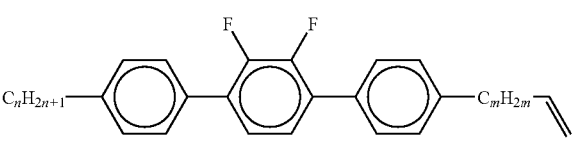
PYP-n-mV
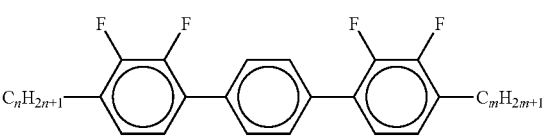
YPY-n-m
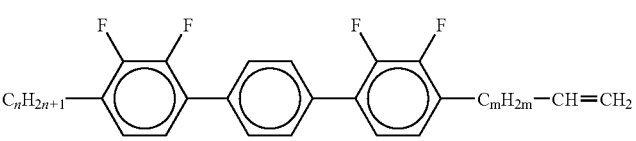
YPY-n-mV
BCH-nm
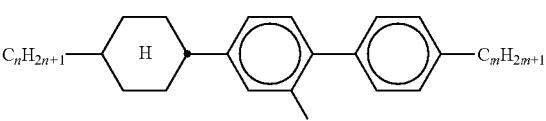
BCH-nmF
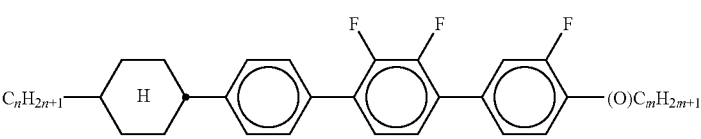
CPYP-n-(O)m TABLE A-continued CPGP-n-m CPYC-n-m CYYC-n-m CCYY-n-m CPYG-n-(O)m CBC-nm CBC-nmF CNap-n-Om CCNap-n-Om

TABLE A-continued

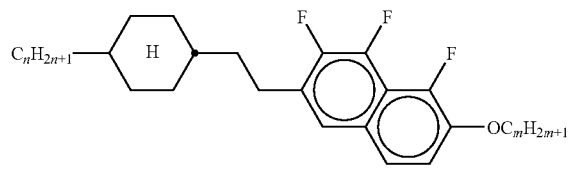

CENap-n-Om

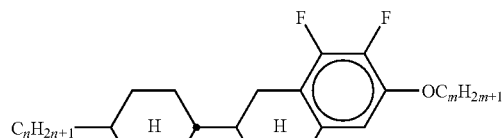

CTNap-n-Om

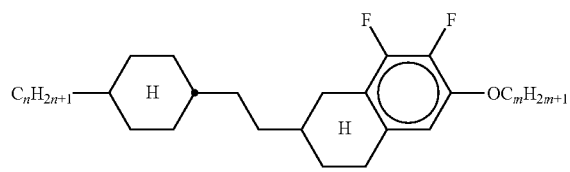

CETNap-n-Om

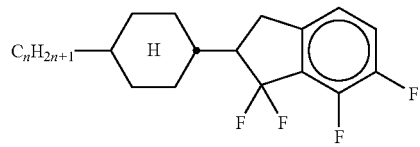

CK-n-F

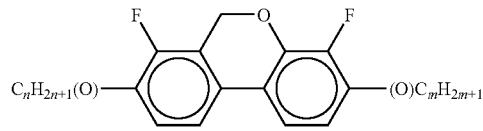

DFDBC-n(O)-(O)m

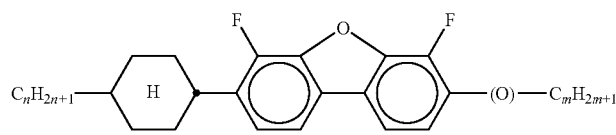

C-DFDBF-n-(O)m

In a preferred embodiment of the present invention, the LC media according to the invention comprise one or more compounds selected from the group consisting of compounds from Table A.

TABLE B

Table B indicates possible dopants which can be added to the LC media according to the invention.

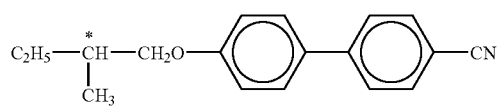

C 15

TABLE B-continued
Table B indicates possible dopants which can be added to the LC media according to the invention.
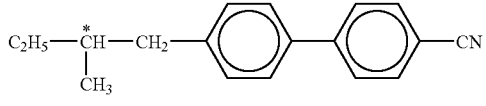
CB 15
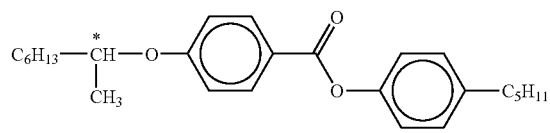
CM 21
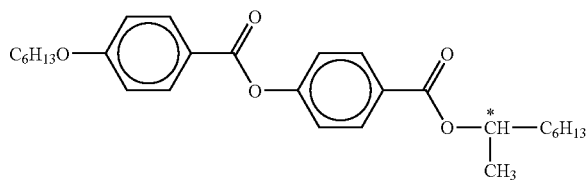
R/S-811
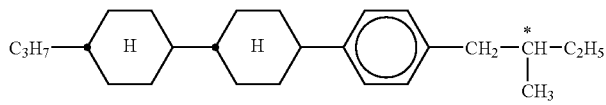
CM 44
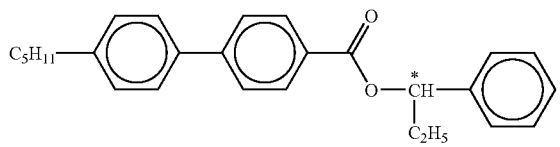
CM 45
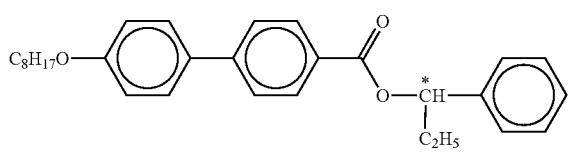
CM 47
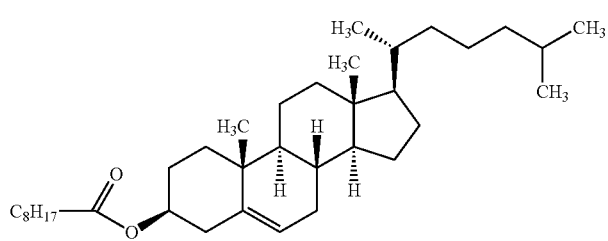
CN
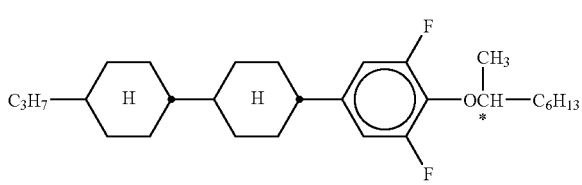
R/S-2011

TABLE B-continued

Table B indicates possible dopants which can be added to the LC media according to the invention.

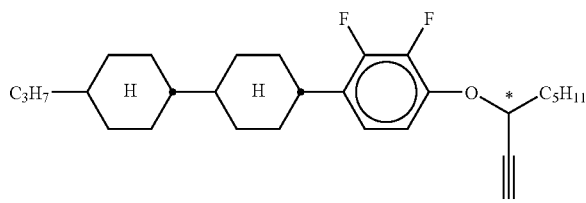

R/S-3011

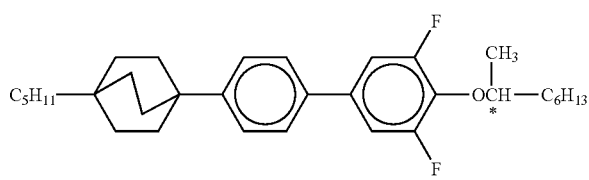

R/S-4011

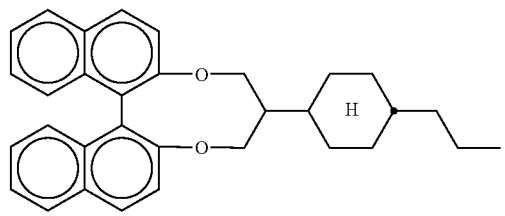

R/S-5011

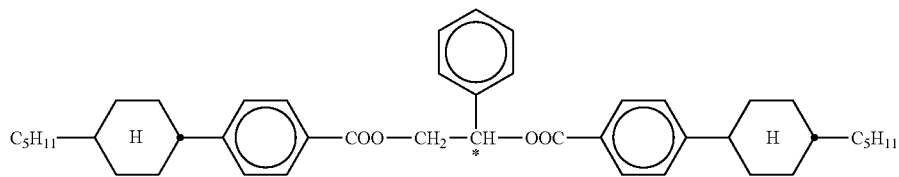

R/S-1011

The LC media preferably comprise 0 to 10% by weight, in particular 0.01 to 5% by weight and particularly preferably 0.1 to 3% by weight, of dopants. The LC media preferably comprise one or more dopants selected from the group consisting of compounds from Table B.

TABLE C

Table C indicates possible stabilizers which can be added to the LC media according to the invention.

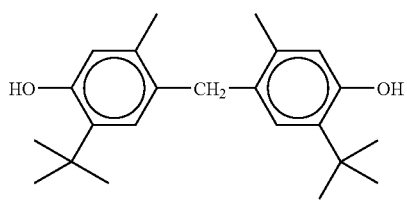

TABLE C-continued
Table C indicates possible stabilizers which can be added to the LC media according to the invention.
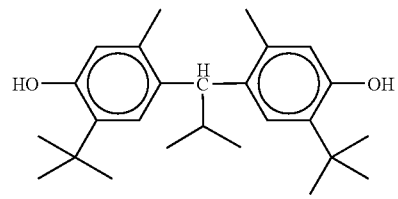
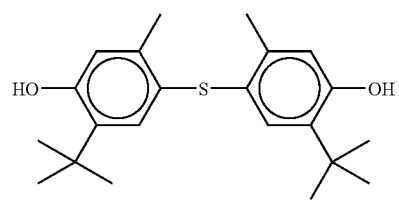
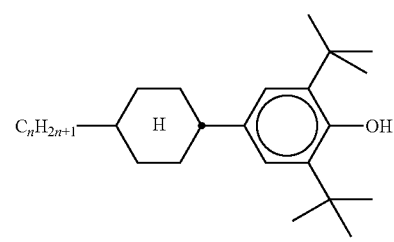
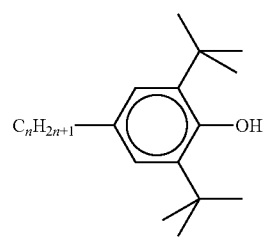
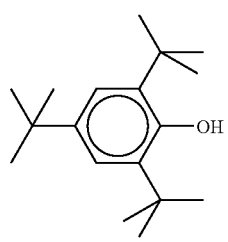
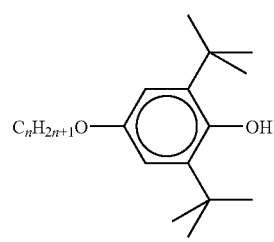

TABLE C-continued
Table C indicates possible stabilizers which can be added to the LC media according to the invention.
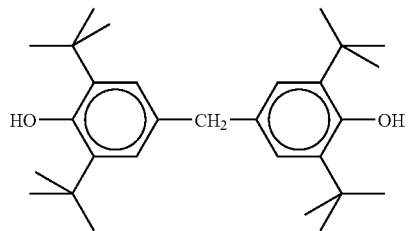
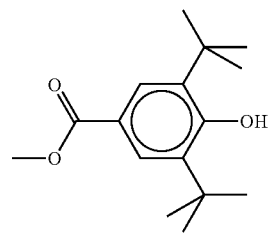
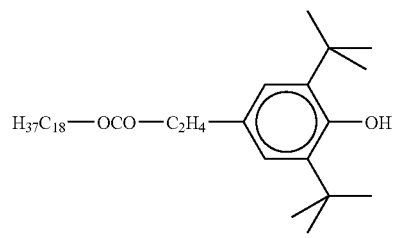
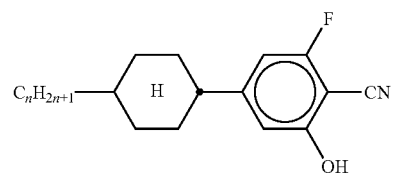
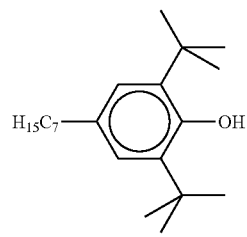
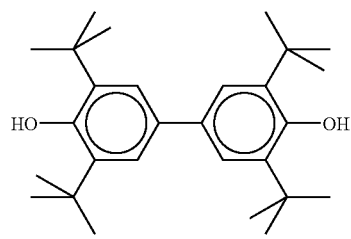

TABLE C-continued
Table C indicates possible stabilizers which can be added to the LC media according to the invention.
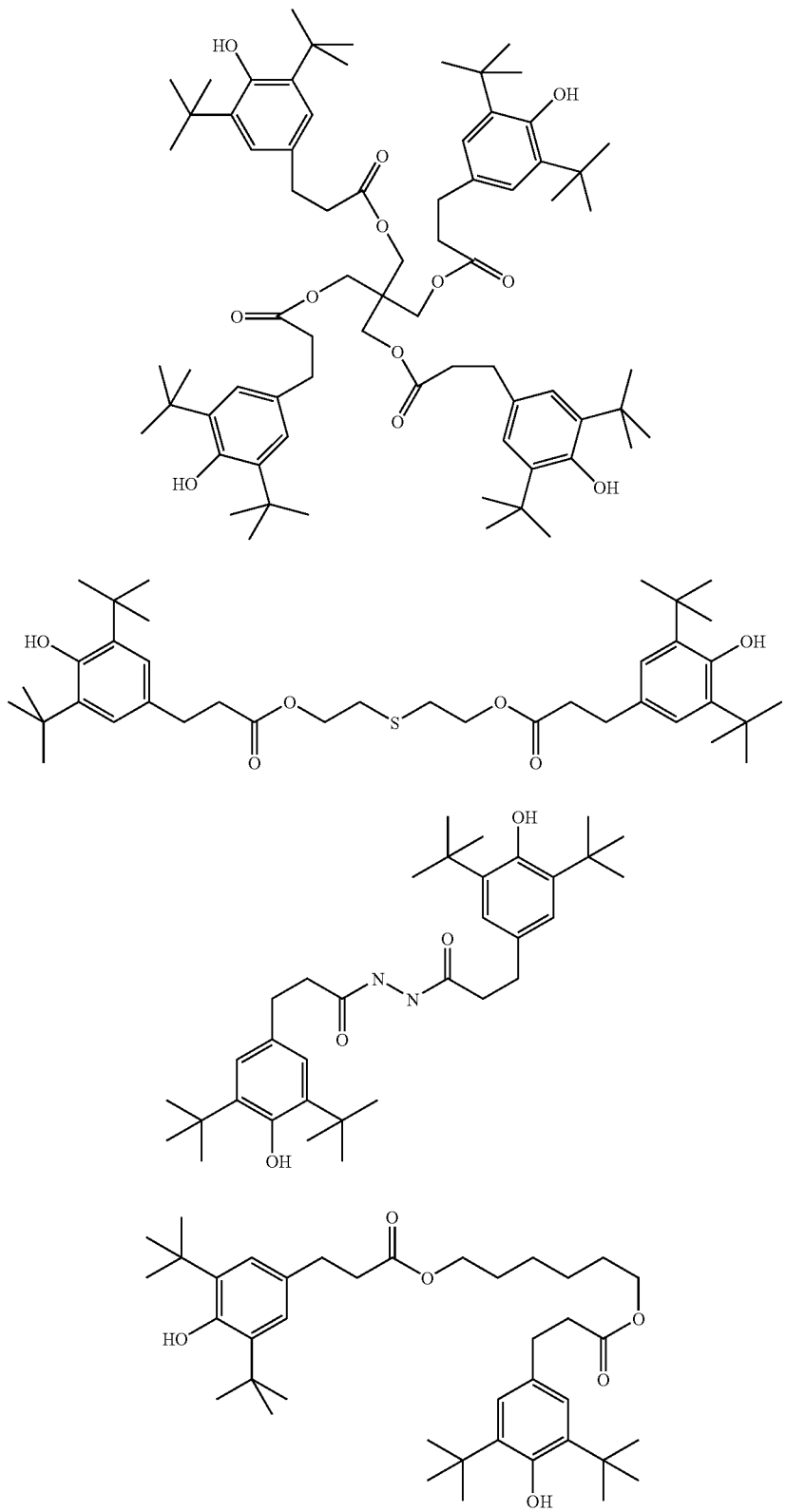

TABLE C-continued
Table C indicates possible stabilizers which can be added to the LC media according to the invention.
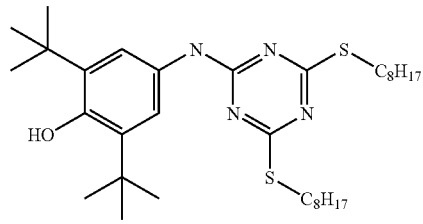
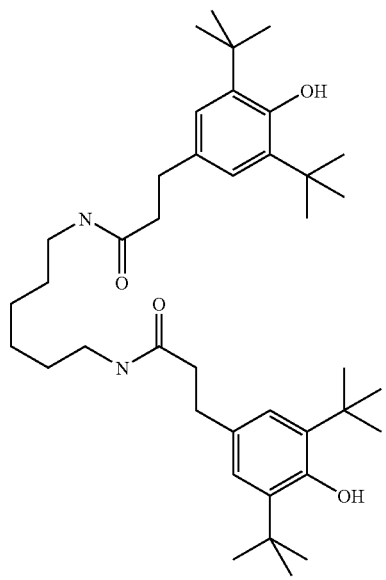
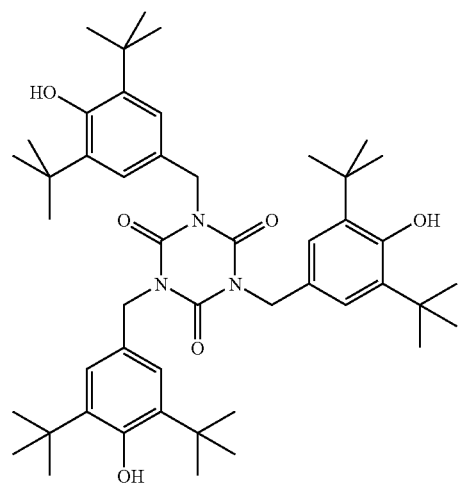

TABLE C-continued
Table C indicates possible stabilizers which can be added to the LC media according to the invention.
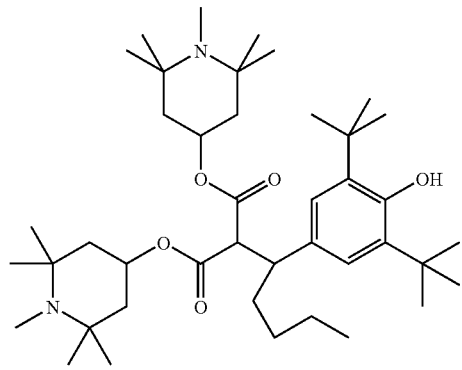
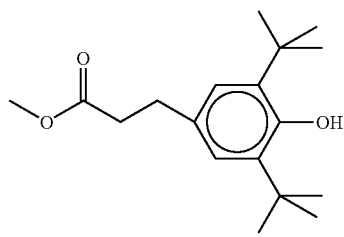
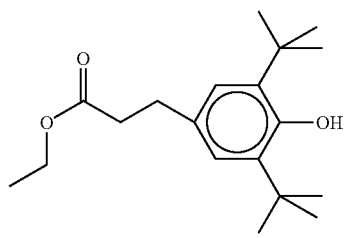
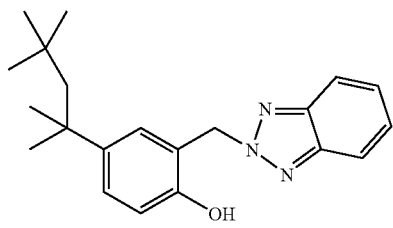
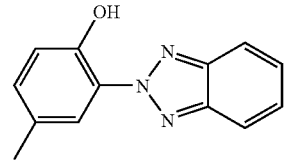
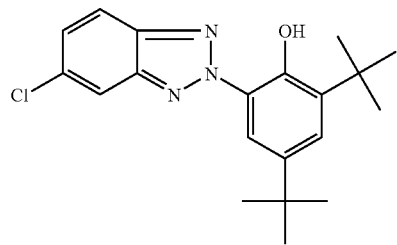

TABLE C-continued
Table C indicates possible stabilizers which can be added to the LC media according to the invention.
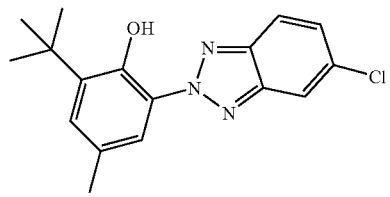
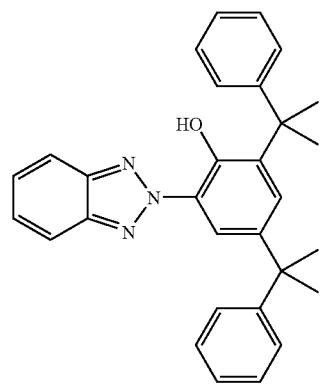
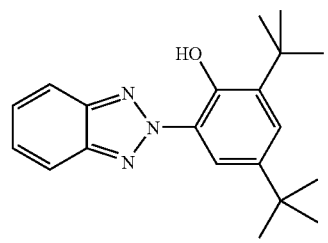
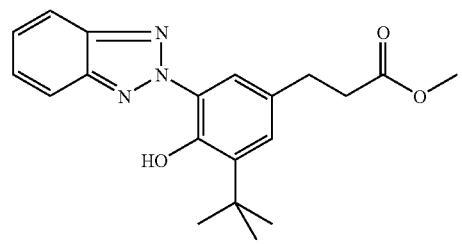
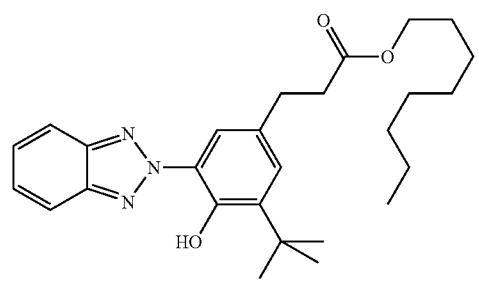

TABLE C-continued
Table C indicates possible stabilizers which can be added to the LC media according to the invention.
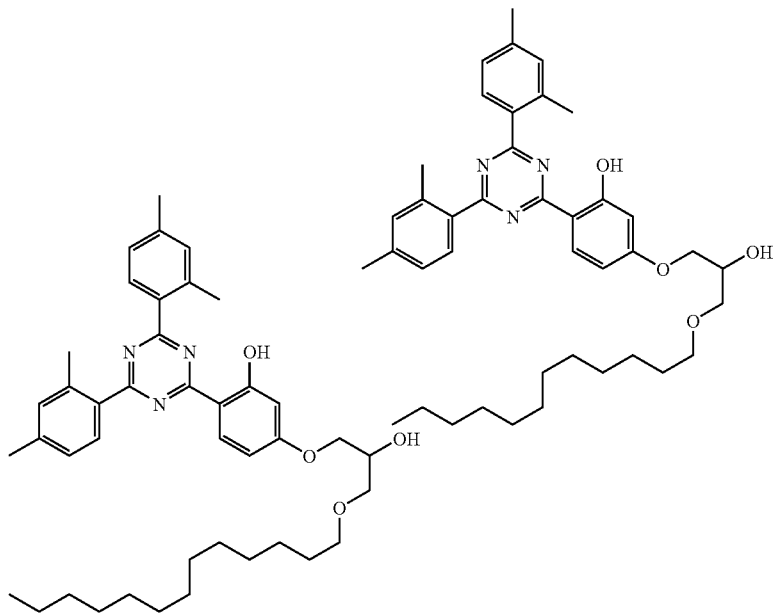
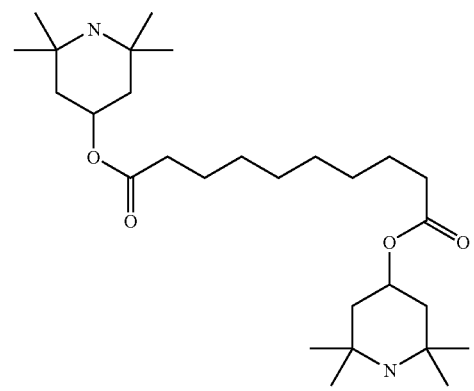
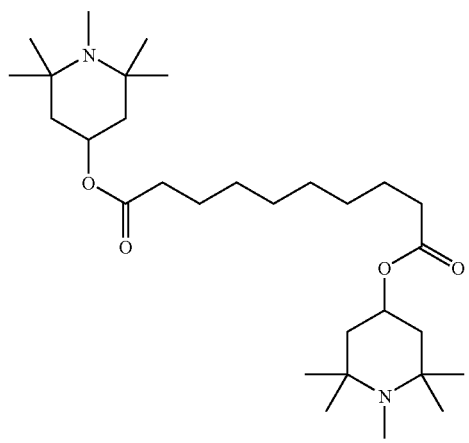
(n here denotes an integer from 1 to 12).

The LC media preferably comprise 0 to 10% by weight, in particular 0.01 to 5% by weight and particularly preferably 0.1 to 3% by weight, of stabilizers. The LC media preferably comprise one or more stabilizers selected from the group consisting of compounds from Table C.

In addition, the following abbreviations and symbols are used:
$V_o$ threshold voltage, capacitive [V] at 20° C.,
$n_e$ extraordinary refractive index at 20° C. and 589 nm,
$n_o$ ordinary refractive index at 20° C. and 589 nm,
$\Delta n$ optical anisotropy at 20° C. and 589 nm,
$\in_\perp$ dielectric susceptibility perpendicular to the director at 20° C. and 1 kHz,
$\in_\parallel$ dielectric susceptibility parallel to the director at 20° C. and 1 kHz,
$\Delta \in$ dielectric anisotropy at 20° C. and 1 kHz,
cl.p., T(N,I) clearing point [° C.],
$\gamma_1$ rotational viscosity at 20° C. [mPa·s],
$K_1$ elastic constant, "splay" deformation at 20° C. [pN],
$K_2$ elastic constant, "twist" deformation at 20° C. [pN],
$K_3$ elastic constant, "bend" deformation at 20° C. [pN],
LTS low-temperature stability (phase), determined in test cells,
$HR_{20}$ voltage holding ratio at 20° C/ [%] and
$HR_{100}$ voltage holding ratio at 100° C. [%].

Unless explicitly noted otherwise, all concentrations in the present application are indicated in per cent by weight and relate to the corresponding mixture as a whole without solvents.

Unless explicitly noted otherwise, all temperature values indicated in the present application, such as, for example, the melting point T(C,N), the transition from the smectic (S) to the nematic (N) phase T(S,N) and the clearing point T(N,I), are indicated in degrees Celsius (° C.). M.p. denotes melting point, Cl.p.=clearing point. Furthermore, C=crystalline state, N=nematic phase, S=smectic phase and I=isotropic phase. The data between these symbols represent the transition temperatures.

All physical properties are and have been determined in accordance with "Merck Liquid Crystals, Physical Properties of Liquid Crystals", Status November 1997, Merck KGaA, Germany, and apply to a temperature of 20° C., and $\Delta n$ is determined at 589 nm and $\Delta \in$ at 1 kHz, unless explicitly indicated otherwise in each case.

The term "threshold voltage" for the present invention relates to the capacitive threshold ($V_0$), also called the Freedericksz threshold, unless explicitly indicated otherwise. In the examples, as generally usual, the optical threshold for 10% relative contrast ($V_{10}$) may also be indicated.

The display used for measurement of the capacitive threshold voltage has two plane-parallel outer plates at a separation of 4 µm and electrode layers with rubbed polyimide alignment layers on top on the insides of the outer plates, which effect a homeotropic edge alignment of the liquid-crystal molecules.

The polymerizable compounds are polymerized in the display in a pre-specified time by UV irradiation, with a voltage simultaneously being applied to the display (usually 10 V to 30 V alternating current, 1 kHz). In the examples, unless indicated otherwise, a 28 mW/cm² mercury vapour lamp is used, the intensity is measured using a standard UV meter (Ushio UNI meter) fitted with a 365 nm band-pass filter.

The tilt angle is determined by rotational crystal experiment (Autronic-Melchers TBA-105). A small value (i.e. a large deviation from 90° angle) corresponds to a large tilt here.

The HR value is measured as follows: 0.3% of a polymerizable mono-meric compound is added to the LC host mixture, and the resultant mixture is introduced into TN-VHR test cells (rubbed at 90°, TN-polyimide alignment layer, layer thickness d≈4 µm). The HR value is determined after 5 min at 100° C. before and after UV exposure for 2 h (sun test) at 1 V, 60 Hz, 64 µs pulse (measuring instrument: Autronic-Melchers VHRM-105).

EXAMPLE 1

Compound (A) is prepared in accordance with Schemes 1 and 3.

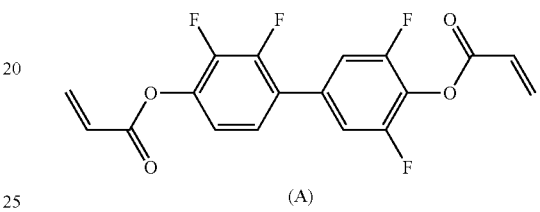

(A)

Step a):

76 g of 2,3-difluorophenol (1) are initially introduced in 400 ml of dichloromethane at room temperature (RT) with stirring and under an $N_2$ atmosphere, 99 ml of triethylamine and 3.5 g of 4-dimethylaminopyridine are added, and the reaction mixture is cooled to −15° C. using a dry-ice/alcohol bath. A solution of 100 g of dimethyl-tert-butylchlorosilane in 100 ml of dichloromethane is added dropwise at this temperature at such a rate that the temperature does not rise above 0° C. (a suspension forms). The cold bath is subsequently removed, and stirring is continued overnight. The precipitated ammonium chloride is filtered off with suction, 500 ml of water are added to the reaction mixture, which is transferred into a separating funnel and shaken, the aqueous phase is let out, and the mixture is extracted 2× with methyl tert-butyl (MTB) ether. The combined organic phases are washed 2× with water and 1× with sodium chloride solution, dried over sodium sulfate, filtered and evaporated, giving 147.1 g of a yellow liquid (2).

Step b):

142.5 g of tert-butyl-(2,3-difluorophenoxy)dimethylsilane (2) are initially introduced in 800 ml of THF in a 4 liter four-necked apparatus and cooled to −70° C. under nitrogen. 320.8 ml of 1.6 M BuLi in hexane are then added dropwise at −70° C., stirring is continued for 45 minutes, and finally 57 ml of trimethyl borate are added dropwise at −70° C., during which a white precipitate deposits. When the dropwise addition is complete, stirring is continued at −70° C. for a further 30 minutes, and the batch is then allowed to cool to RT, during which the white precipitate completely dissolves at about 10° C., and a virtually colorless clear solution is formed. The mixture is hydrolysed using 120 ml of deionised water and adjusted to pH 6 using 240 ml of semi-conc. HCl. The organic phase is separated off, washed by shaking with water, dried and evaporated in a rotary evaporator. The brown mass obtained is extracted by stirring 1:2 from hexane at 0° C., filtered off with suction and dried, giving 60.3 g of beige powder (3).

Step c):

20.2 g of 2,3-difluoro-4-tert-butyldimethylsiloxyphenyl-boronic acid (3), 21.2 g of 4-bromo-2,6-difluorophenol (4), 21.5 ml of sodium metaborate octahydrate, 2.2 g of bis(triphenylphosphino)palladium(II) chloride, 0.13 g of hydrazinium hydroxide and 200 ml of THF are combined at RT, heated to reflux and stirred under reflux overnight. Deionised water is subsequently added to the reaction mixture, which is allowed to cool to RT. MTB ether is added, the aqueous phase is extracted with MTB ether, and the combined organic phases are dried over $Na_2SO_4$, filtered and evaporated in a rotary evaporator. The brown mass is filtered through a frit with heptane:ethyl acetate 1:1, and the corresponding fractions are evaporated in a rotary evaporator, giving 27.1 g of white crystals (5).

Step g):

13.5 g of 2,3,3',5'-tetrafluoro-4,4'-dihydroxybiphenyl (5) and 8.75 ml of chloropropionyl chloride are initially introduced in 70 ml of dichloromethane, 30 ml of triethylamine are added dropwise at 20° C. (ice-cooling), and stirring is continued overnight at RT. The reaction mixture is poured into 300 ml of water, the mixture is adjusted to pH 2 using hydrochloric acid, and the phases are then separated. The mixture is subsequently extracted 2× with $CH_2Cl_2$, and the organic phase is extracted 2× with water, dried over $Na_2SO_4$, filtered and evaporated in a rotary evaporator. Chromatography in n-heptane:ethyl acetate 3:1 and recrystallisation from ethyl acetate gives 2.1 g of white crystals.

EXAMPLE 2

Compound (B) is prepared in accordance with Scheme 3 from the diol (5) obtained in accordance with Example 1, steps a)-c).

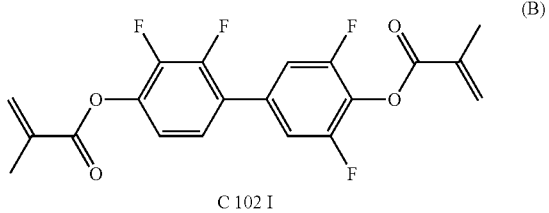

(B)

C 102 I

Step h):

13.5 g of 2,3,3',5'-tetrafluoro-4,4'-dihydroxybiphenyl (5), 9.1 ml of methacrylic acid and 0.42 g of dimethylaminopyridine are initially introduced in 350 ml of toluene. A solution of 23.1 g of DCC in 100 ml of THF is added dropwise at a maximum of 10° C., and the mixture is stirred overnight. Next day, 0.65 g of oxalic acid dihydrate is added, and stirring is continued at RT for 1 hour. The mixture is filtered with suction, washed with toluene and evaporated in a rotary evaporator. The pale-yellow crystals obtained are passed through a silica-gel column with n-heptane: ethyl acetate 2:1. The white crystals then obtained are filtered through a 250 ml Seitz filter from 200 ml of hot heptane+Celite, recrystallised at room temperature, filtered off with suction and dried in a vacuum drying cabinet. Repeated recrystallisation from methanol gives 6.4 g of white crystals.

EXAMPLE 3

Mixture Example

The nematic LC host mixture N1 is formulated as follows:

| CCH-501 | 9.00% | Cl.p. | +70.0 |
| CCH-35 | 14.00% | Δn | 0.0825 |
| PCH-53 | 8.00% | Δε | −3.5 |
| CY-3-O4 | 14.00% | $\epsilon_\parallel$ | 3.5 |
| CY-5-O4 | 13.00% | $K_3/K_1$ | 1.00 |
| CCY-3-O2 | 8.00% | $\gamma_1$ | 141 |
| CCY-5-O2 | 8.00% | $V_0$ | 2.06 |
| CCY-2-1 | 9.00% | | |
| CCY-3-1 | 9.00% | | |
| CPY-2-O2 | 8.00% | | |

0.3% of the polymerizable monomeric compound B from Example 2 is added to LC mixture N1, and the resultant mixture is introduced into VA e/o test cells (rubbed at 90°, VA-polyimide alignment layer, layer thickness d≈4 μm). With application of a voltage of 10 V (alternating current), the cell is irradiated for 20 minutes with UV light having an intensity of 28 mW/cm², causing the polymerization of the monomeric compound.

In a second experiment, 0.006% of the photoinitiator Irgacure-651 is additionally added to the LC/monomer mixture, and the exposure time is shortened to 2 minutes. Before and after the UV irradiation, the tilt angle is determined by rotational crystal experiment (Autronic-Melchers TBA-105). The results are shown in Table 1.

TABLE 1

| Monomer | Initiator | Tilt before UV | Tilt after UV |
|---|---|---|---|
| (B) | no | 89.9° | 86.9° |
| (B) | yes | 89.9° | 86.0° |

As is evident from Table 1, a sufficiently large tilt (i.e. small tilt angle) can be achieved after polymerization with compound B according to the invention.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding German application No. 10 2007 057 680.5, filed Nov. 30, 2007, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof can make various changes and modifications of the invention to adapt it to various usages and conditions.

The invention claimed is:

1. A compound of formula I

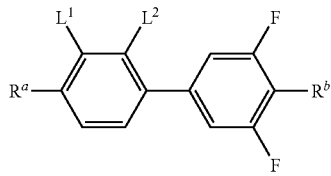

I wherein:
- $R^a$ and $R^b$ are each, independently, P-Sp-, H, F, Cl, Br, I, —CN, —NCO, —NCS, —OCN, —SCN, $SF_5$, or straight-chain or branched alkyl having 1 to 25 C atoms wherein one or more non-adjacent $CH_2$ groups are each optionally replaced, independently of one another, by -C($R^{00}$)=C($R^{000}$)—, —C≡C—, —N($R^{00}$)—, —O—, —S—, —CO—, —CO—O—, —O—CO—, —O—CO—O— in such a way that O and/or S atoms are not linked directly to one another, and wherein one or more H atoms are each optionally replaced by F, Cl, Br, I, CN or P-Sp-, and at least one of $R^a$ and $R^b$ is or contains a group P-Sp-;
- P is, in each case independently, a polymerizable group;
- Sp is, in each case independently, a spacer group or a single bond;
- $R^{00}$ and $R^{000}$ are each, independently of one another, H or alkyl having 1 to 12 C atoms; and
- $L^1$ and $L^2$ are each, independently of one another, H or F.

2. A compound according to claim 1, wherein:
P is, in each case independently, $CH_2$=$CW^1$—COO—, $CH_2$=$CW^1$—CO—,

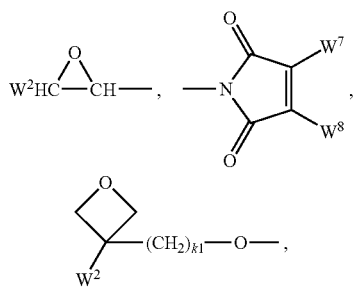

$CH_2$=$CW^2$—(O)$_{k3}$—, $CH_3$—CH=CH—O—, ($CH_2$=CH)$_2$CH—OCO—, ($CH_2$=CH—$CH_2$)$_2$CH—OCO—, ($CH_2$=CH)$_2$CH—O—, ($CH_2$=CH—$CH_2$)$_2$N—, ($CH_2$=CH—$CH_2$)$_2$N—CO—, HO—$CW^2W^3$—, HS—$CW^2W^3$—, HW$^2$N—, HO—$CW^2W^3$—NH—, $CH_2$=$CW^1$—CO—NH—, $CH_2$=CH—(COO)$_{k1}$—Phe-(O)$_{k2}$—, $CH_2$=CH—(CO)$_{k1}$—Phe-(O)$_{k2}$—, Phe-CH=CH—, HOOC—, OCN— or $W^4W^5W^6$Si—;
$W^1$ is H, F, Cl, CN, $CF_3$, phenyl or alkyl having 1 to 5 C atoms;
$W^2$ and $W^3$ are each, independently of one another, H or alkyl having 1 to 5 C atoms;
$W^4$, $W^5$ and $W^6$ are each, independently of one another, Cl, oxaalkyl having up to 5 C atoms, or oxacarbonylalkyl having up to 5 C atoms;
$W^7$ and $W^8$ are each, independently of one another, is H, Cl or alkyl having 1 to 5 C atoms;
Phe is 1,4-phenylene, which is optionally one or more by L;
$k_1$, $k_2$ and $k_3$ are each, independently of one another, 0 or 1;
L is F, Cl, Br, I, —CN, —$NO_2$, —NCO, —NCS, —OCN, —SCN, —C(=O)N($R^{00}$)$_2$, —C(=O)$R^{00}$, —N($R^{00}$)$_2$, optionally substituted silyl, optionally substituted aryl having 6 to 20 C atoms, or straight-chain or branched alkyl, alkoxy, alkylcarbonyl, alkoxycarbonyl, alkylcarbonyloxy or alkoxycarbonyloxy having up to 25 C atoms, in which, in addition, one or more H atoms may be replaced by F or Cl;
Sp are each independently Sp'-X';
Sp' is alkylene having 1 to 20 which is optionally mono- or polysubstituted by F, Cl, Br, I or CN and in which, in addition, one or more non-adjacent $CH_2$ groups are each optionally replaced by, independently of one another, —O—, —S—, —NH—, —$NR^{00}$—, —$SiR^{00}R^{000}$—, —CO—, —COO—, —OCO—, —OCO—O—, —S—CO—, —CO—S—, —$NR^{00}$—CO—O—, —O—CO—$NR^{00}$—, —$NR^{00}$—CO—$NR^{00}$—, —CH=CH— or —C≡C— in such a way that O and/or S atoms are not linked directly to one another;
X' is —O—, —S—, —CO—, —COO—, —OCO—, —O—COO—, —CO—$NR^{00}$—, —$NR^{00}$—CO—, —$NR^{00}$—CO—$NR^{00}$—, —$OCH_2$—, —$CH_2O$—, —$SCH_2$—, —$CH_2S$—, —$CF_2O$—, —$OCF_2$—, —$CF_2S$—, —$SCF_2$—, —$CF_2CH_2$—, —$CH_2CF_2$—, —$CF_2CF_2$—, —CH=N—, —N=CH—, —N=N—, —CH=$CR^{00}$—, —$CY^2$=$CY^3$—, —C≡C—, —CH=CH—COO—, —OCO—CH=CH— or a single bond;
$R^{00}$ and $R^{000}$ are each, independently of one another, H or alkyl having 1 to 12 C atoms,
$Y^2$ and $Y^3$ are each, independently of one another, H, F, Cl or CN.

3. A compound according to claim 2, wherein:
P is $CH_2$=$CW^1$—COO—, $CH_2$=CH—O—, ($CH_2$=CH)$_2$CH—OCO—, ($CH_2$=CH)$_2$CH—O—,

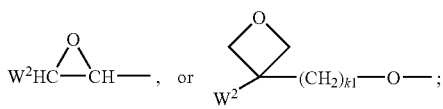

Sp' is —($CH_2$)$_{p1}$—, —($CH_2CH_2O$)$_{q1}$—$CH_2CH_2$—, —$CH_2CH_2$—S—$CH_2CH_2$—, —$CH_2CH_2$—NH—$CH_2CH_2$— or —($SiR^{00}R^{000}$—O)$_{p1}$—;
p1 is an integer from 1 to 12;
q1 is an integer from 1 to 3: and
X' is —O—, —S—, —CO—, —COO—, —OCO—, —O—COO—, —CO—$NR^{00}$—, —$NR^{00}$—CO—, —$NR^{00}$—CO—$NR^{00}$—, or a single bond.

4. A compound according to claim 1, wherein one or both of $L^1$ and $L^2$ are F.

5. A compound according to claim 1, wherein $R^a$ and $R^b$ are each, identical or different, P-Sp- in which one or both Sp groups is a single bond.

6. A compound according to claim 1, selected from formulae I1 to I4:

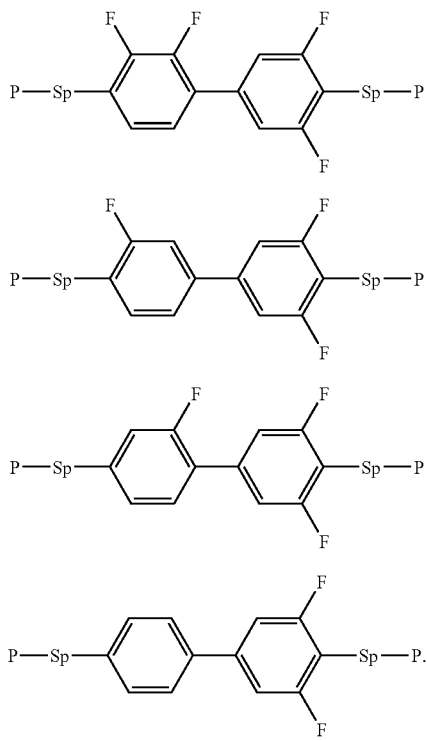

7. A process for preparing a compound according to claim 1, comprising:
   a) reacting of the OH group of 2,3-difluorophenol with a protecting group;
   b) metallating the resultant product from a) in the para-position to form the protected phenol group, and then subsequently reacting the resultant compound with a boronic acid or a boronic acid ester;
   c) coupling the resultant product from b) to 4-halo-2,6-difluorophenol in the presence of a transition-metal catalyst and removing the protecting group to give 2,3,3',5'-tetrafluorobiphenyl-4,4'-diol; and
   g) reacting the phenolic OH groups with chloropropionyl chloride and subsequently eliminating HCl, or
   h) etherifying or esterifying the phenolic OH groups using an acid, an acid derivative or a halogenated compound containing a group P.

8. A process for preparing a compound according to claim 1, comprising:
   d) reacting the OH group of 4-halo-2,6-difluorophenol with a protecting group;
   e) dehalogenating the product from d) in the para-position to form the protected phenol ether group, and subsequently reacting the resultant compound with a boronic acid or a boronic acid ester;
   f) coupling the product from e) to 4-halo-2-fluorophenol or 4-halo-3-fluorophenol in the presence of a transition-metal catalyst, and removing the protecting group to give 2,3',5'-trifluorobiphenyl-4,4'-diol or 3,3',5'-trifluorobiphenyl-4,4'-diol, respectively; and
   g) reacting the phenolic OH groups with chloropropionyl chloride and subsequently eliminating HCl, or
   h) etherifying or esterifying the phenolic OH groups using an acid, an acid derivative or a halogenated compound containing a group P.

9. A compound of formula Ia

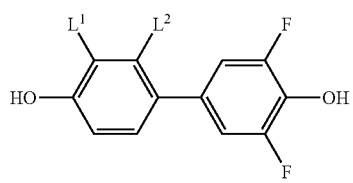

wherein $L^1$ and $L^2$ are each, independently of one another, H or F.

10. A compound according to claim 9, wherein said compound is selected from formulae Ia1-Ia4:

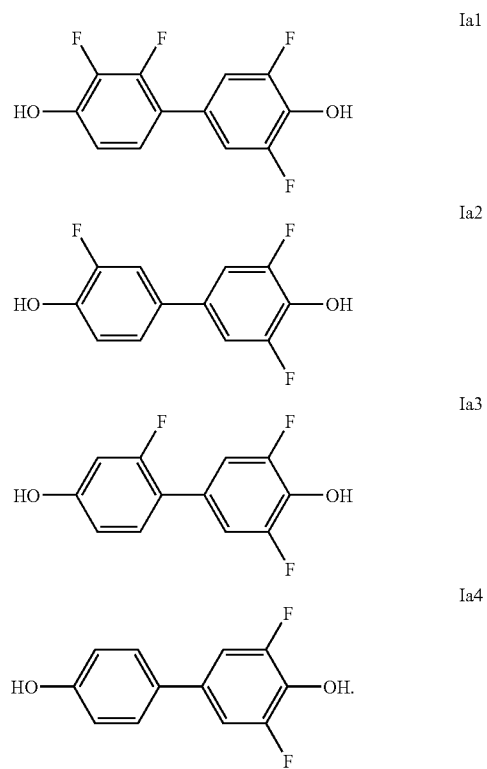

11. A liquid-crystal medium comprising one or more compounds according to claim 1, and one or more additional compounds, wherein said one or more additional compounds is mesogenic, liquid-crystalline, and/or polymerizable.

12. A liquid-crystal medium comprising:
   a polymerizable component A) comprising one or more compounds according to claim 1; and
   a liquid-crystalline component B) comprising one or more low-molecular-weight compounds.

13. A liquid-crystal medium according to claim 11, wherein said medium comprises one or more compounds of formulae CY and PY:

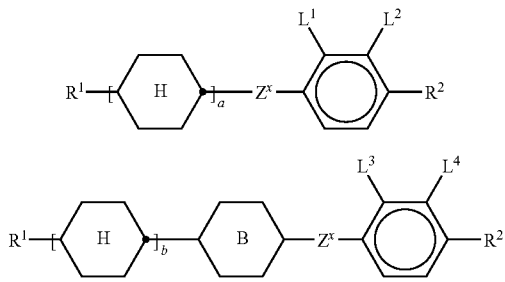
CY

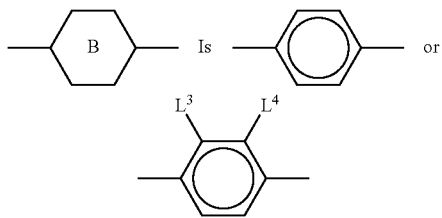
PY wherein:
a is 1 or 2;
b is 0 or 1;

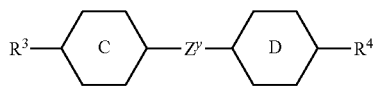

R¹ and R² are each, independently of one another, alkyl having 1 to 12 C atoms, in which, in addition, one or two non-adjacent $CH_2$ groups are each optionally replaced by —O—, —CH=CH—, —CO—, —OCO— or —COO— in such a way that O atoms are not linked directly to one another;

$Z^x$ is —CH=CH—, —$CH_2$O—, —O$CH_2$—, —$CF_2$O—, —OC$F_2$—, —O—, —$CH_2$—, —$CH_2CH_2$—, or a single bond, and $L^{1-4}$ are each, independently of one another, F, Cl, OC$F_3$, C$F_3$, $CH_3$, $CH_2$F, CH$F_2$.

14. A liquid-crystal medium according to claim 11, wherein said medium comprises one or more compounds of formula ZK:

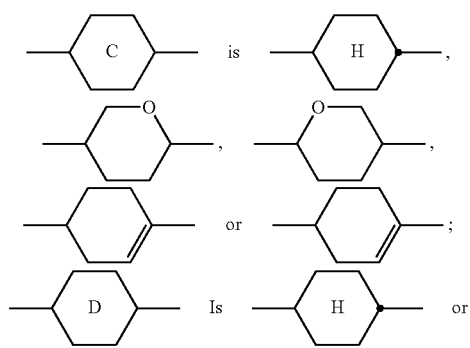
ZK wherein:

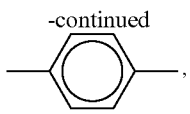

R³ and R⁴ are each, independently of one another, alkyl having 1 to 12 C atoms wherein one or two non-adjacent $CH_2$ groups are each optionally replaced by —O—, —CH=CH—, —CO—, —OCO— or —COO— in such a way that O atoms are not linked directly to one another; and $Z^y$ is —$CH_2CH_2$—, —CH=CH—, —$CF_2$O—, —OC$F_2$—, —$CH_2$O—, —OC$H_2$—, —COO—, —OCO—, —$C_2F_4$—, —CF=CF— or a single bond.

15. A polymer obtainable by polymerization of one or more compounds according to claim 1 or of an LC medium.

16. A polymer film obtainable by polymerization of a layer comprising one or more compounds according to claim 1 or an LC medium in the uniformly aligned state in the LC phase.

17. In electro-optical displays, liquid-crystal (LC) displays, optical films, polarizers, compensators, beam splitters, reflective polarizers, alignment layers, colored filters, holographic elements, heat-sealing films, adhesion films, optical data storage media, in nonlinear optics, effect pigments, decorative elements, security elements, security markings, electrical semiconductors, organic field-effect transistors (OFETs), integrated circuits (ICs), thin-film transistors (TFTs), radio frequency identification elements (RFIDs), organic light-emitting diodes (OLEDs), electroluminescent displays, illumination elements, photovoltaic devices, optical sensors, photoconductors, or cosmetic formulations, containing a liquid crystalline medium or a polymer film obtainable by polymerization of a liquid crystalline medium, the improvement wherein said medium contains a compound according to claim 1.

18. A liquid crystal display comprising one or more compounds, an LC medium, a polymer or a polymer film according to claim 1.

19. A PS (polymer-stabilized) or PSA (polymer-sustained alignment) liquid crystal display comprising:
a liquid crystal cell comprising two substrates, where at least one of said substrates transmits light and at least one of said substrates has an electrode layer, and
a layer of liquid crystal medium located between said substrates comprising a polymerized component and a low-molecular-weight component, wherein said polymerized component is obtainable by polymerization of one or more polymerizable compounds between the substrates of the liquid crystal cell in the liquid crystal medium by application of an electrical voltage,
wherein said liquid crystal display contains one or more compounds according to claim 1.

20. A liquid crystal display according to claim 18, wherein said display is a PSA-VA, PSA-OCB, PS-IPS, PS-FFS or PS-TN display.

21. A compound according to claim 1, wherein $R^a$ and $R^b$ are each, identical or different, P-Sp-.

22. A compound according to claim 1, wherein one of $L^1$ and $L^2$ is F and the other is H.

23. A compound according to claim 1, wherein both $L^1$ and $L^2$ are F.

24. A compound according to claim 2, wherein -Sp'-X'- is —$(CH_2)_{p1}$—, —O—$(CH_2)_{p1}$—, —OCO—$(CH_2)_{p1}$—, or —OCOO—$(CH_2)_{p1}$—.

25. A compound according to claim 2, wherein -Sp'-X'- is straight-chain ethylene, propylene, butylene, pentylene, hexylene, heptylene, octylene, nonylene, decylene, undecylene, dodecylene, octadecylene, ethyleneoxyethylene, methyleneoxybutylene, ethylenethioethylene, ethylene-N-methyliminoethylene, 1-methylalkylene, ethenylene, propenyl-ene, or butenylene.

26. A compound according to claim 1, wherein $R^a$ and/or $R^b$ in formula I are selected from the following formulae:

| | |
|---|---|
| —X-alkyl-CHP$^1$—CH$_2$—CH$_2$P$^2$ | I*a |
| —X-alkyl-C(CH$_2$P$^1$)(CH$_2$P$^2$)—CH$_2$P$^3$ | I*b |
| —X-alkyl-CHP$^1$CHP$^2$—CH$_2$P$^3$ | I*c |
| —X-alkyl-C(CH$_2$P$^1$)(CH$_2$P$^2$)—C$_{aa}$H$_{2aa+1}$ | I*d |
| —X-alkyl-CHP$^1$—CH$_2$P$^{29}$ | I*e |
| —X-alkyl-CHP$^1$P$^2$ | I*f |
| —X-alkyl-CP$^1$P$^2$—C$_{aa}$H$_{2aa+1}$ | I*g |
| —X-alkyl-C(CH$_2$P$^1$)(CH$_2$P$^2$)—CH$_2$OCH$_2$—C(CH$_2$P$^3$)(CH$_2$P$^4$)CH$_2$P$^5$ | I*h |
| —X-alkyl-CH((CH$_2$)$_{aa}$P$^1$)((CH$_2$)$_{bb}$P$^2$) | I*i |
| —X-alkyl-CHP$^1$CHP$^2$—C$_{aa}$H$_{2aa+1}$ | I*k |
| —X'-alkyl-C(CH$_3$)(CH$_2$P$^1$)(CH$_2$P$^2$) | I*m | wherein
alkyl is a single bond or straight-chain or branched alkylene having 1 to 12 C atoms, in which one or more non-adjacent CH$_2$ groups are each, independently of one another, optionally replaced by —C(R$^{00}$)=C(R$^{000}$)—, —C≡C—, —N(R$^{00}$)—, —O—, —S—, —CO—, —CO—O—, —O—CO—, —O—CO—O— in such a way that O and/or S atoms are not linked directly to one another, and in which, in addition, one or more H atoms may be replaced by F, Cl or CN, where R$^{00}$ and R$^{000}$ have the meaning indicated above;
aa and bb each, independently of one another, denote 0, 1, 2, 3, 4, 5 or 6;
X is —O—, —S—, —CO—, —COO—, —OCO—, —O—COO—, —CO—NR$^{00}$—, —NR$^{00}$—CO—, —NR$^{00}$—CO—NR$^{00}$—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH=N—, —N=CH—, —N=N—, —CH=CR$^{00}$—, —CY$^2$=CY$^3$—, —C≡C—, —CH=CH—COO—, —OCO—CH=CH— or a single bond;
P$^{1-5}$ each, independently of one another, CH$_2$=CW$^1$—COO—, CH$_2$=CW$^1$—CO—,

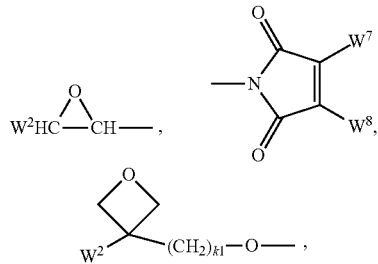

CH$_2$=CW$^2$—(O)$_{k3}$—, CH$_3$-CH=CH—O—, (CH$_2$=CH)$_2$CH—OCO—, (CH$_2$=CH—CH$_2$)$_2$CH—OCO—, (CH$_2$=CH)$_2$CH—O—, (CH$_2$=CH—CH$_2$)$_2$N—, (CH$_2$=CH—CH$_2$)$_2$N—CO—, HO—CW$^2$W$^3$—, HS—CW$^2$W$^3$—, HW$^2$N—, HO—CW$^2$W$^3$—NH—, CH$_2$=CW$^1$—CO—NH—, CH$_2$=CH—(COO)$_{k1}$—Phe-(O)$_{k2}$—, CH$_2$=CH—(CO)$_{k1}$—Phe-(O)$_{k2}$—,Phe-CH=CH—, HOOC—, OCN— or W$^4$W$^5$W$^6$Si—;
W$^1$ is H, F, Cl, CN, CF$_3$, phenyl or alkyl having 1 to 5 C atoms;
W$^2$ and W$^3$ are each, independently of one another, H or alkyl having 1 to 5 C atoms;
W$^4$, W$^5$ and W$^6$ are each, independently of one another, Cl, oxaalkyl having up to 5 C atoms, or oxacarbonylalkyl having up to 5 C atoms;
W$^7$ and W$^8$ are each, independently of one another, is H, Cl or alkyl having 1 to 5 C atoms;
Phe is 1,4-phenylene, which is optionally one or more by L;
k$_1$, k$_2$ and k$_3$ are each, independently of one another, 0 or 1; and
L is F, Cl, Br, I, —CN, —NO$_2$, —NCO, —NCS, —OCN, —SCN, —C(=O)N(R$^{00}$)$_2$, —C(=O)R$^{00}$, —N(R$^{00}$)$_2$, optionally substituted silyl, optionally substituted aryl having 6 to 20 C atoms, or straight-chain or branched alkyl, alkoxy, alkylcarbonyl, alkoxycarbonyl, alkylcarbonyloxy or alkoxycarbonyloxy having up to 25 C atoms, in which, in addition, one or more H atoms may be replaced by F or Cl.

* * * * *

UNITED STATES PATENT AND TRADEMARK OFFICE
CERTIFICATE OF CORRECTION

PATENT NO. : 7,807,068 B2  Page 1 of 1
APPLICATION NO. : 12/275652
DATED : October 5, 2010
INVENTOR(S) : Bremer et al.

It is certified that error appears in the above-identified patent and that said Letters Patent is hereby corrected as shown below:

Column 99, line 63 reads

"  "

Should read:

-- 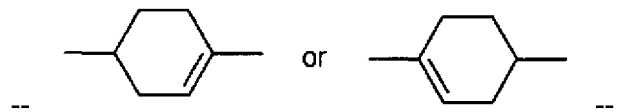 --

Column 101, line 7 reads "nyl-ene, or butenylene." should read -- nylene, or butenylene. --

Column 101, line 18 reads "-X-alkyl-CHP$^1$-CH$_2$P$^{29}$" should read -- -X-alkyl-CHP$^1$-CH$_2$P$^2$ --

Signed and Sealed this
Eighteenth Day of December, 2012

David J. Kappos
*Director of the United States Patent and Trademark Office*